(12) United States Patent
Glass et al.

(10) Patent No.: US 9,212,204 B2
(45) Date of Patent: Dec. 15, 2015

(54) TREATMENT OF RETT SYNDROME USING GLYCYL-L-2-METHYLPROLYL-L-GLUTAMIC ACID

(71) Applicant: Neuren Pharmaceuticals Limited, Auckland (NZ)

(72) Inventors: Lawrence Irwin Glass, Takoma Park, MD (US); Michael John Bickerdike, Auckland (NZ); Michael Frederick Snape, Surrey (GB)

(73) Assignee: Neuren Pharmaceuticals Limited, Auckland (NZ)

( * ) Notice: Subject to any disclaimer, the term of this patent is extended or adjusted under 35 U.S.C. 154(b) by 0 days.

(21) Appl. No.: 14/605,420

(22) Filed: Jan. 26, 2015

(65) Prior Publication Data

US 2015/0197543 A1    Jul. 16, 2015

Related U.S. Application Data

(63) Continuation of application No. 13/699,087, filed as application No. PCT/US2012/000047 on Jan. 27, 2012.

(60) Provisional application No. 61/462,141, filed on Jan. 27, 2011, provisional application No. 61/492,248, filed on Jun. 1, 2011.

(51) Int. Cl.

| A61K 31/401 | (2006.01) |
|---|---|
| A61K 9/00 | (2006.01) |
| C07K 5/062 | (2006.01) |
| A61K 45/06 | (2006.01) |
| A61K 38/06 | (2006.01) |
| A61K 9/127 | (2006.01) |
| A61K 38/05 | (2006.01) |
| A61K 9/06 | (2006.01) |
| A61K 9/107 | (2006.01) |

(52) U.S. Cl.
CPC .............. *C07K 5/06026* (2013.01); *A61K 9/127* (2013.01); *A61K 31/401* (2013.01); *A61K 38/05* (2013.01); *A61K 38/06* (2013.01); *A61K 45/06* (2013.01); *A61K 9/0019* (2013.01); *A61K 9/0085* (2013.01); *A61K 9/06* (2013.01); *A61K 9/107* (2013.01)

(58) Field of Classification Search
CPC ............................ A61K 9/0085; A61K 31/401
See application file for complete search history.

(56) References Cited

U.S. PATENT DOCUMENTS

| 7,041,314 | B2 | 5/2006 | Abood |
|---|---|---|---|
| 7,605,177 | B2 | 10/2009 | Gluckman |
| 7,714,020 | B2 | 5/2010 | Gluckman |
| 7,863,304 | B2 | 1/2011 | Brimble |
| 7,887,839 | B2 | 2/2011 | Wen |
| 7,994,127 | B2 | 8/2011 | Sur et al. |
| 8,178,125 | B2 | 5/2012 | Wen |
| 8,496,963 | B2 | 7/2013 | Wen |
| 8,637,567 | B2 | 1/2014 | Gluckman |
| 8,691,762 | B2 | 4/2014 | Buxbaum |
| 2007/0004641 | A1 | 1/2007 | Gluckman |
| 2007/0298009 | A1* | 12/2007 | Gluckman et al. ........... 424/85.2 |
| 2008/0249082 | A1 | 10/2008 | Hollander |
| 2009/0099077 | A1 | 4/2009 | Sur |
| 2010/0298304 | A1 | 11/2010 | Page |
| 2011/0112033 | A1 | 5/2011 | Gluckman |
| 2012/0177630 | A1 | 7/2012 | Mriganka |
| 2012/0216302 | A1 | 8/2012 | Buxbaum |
| 2014/0147491 | A1 | 5/2014 | Glass |

FOREIGN PATENT DOCUMENTS

| WO | WO2007/106555 | 9/2007 |
|---|---|---|
| WO | WO2008/153929 | 12/2008 |
| WO | WO2011/146109 | 11/2011 |

OTHER PUBLICATIONS

Written Opinion, May 23, 2012, Neuren Pharmaceuticals.
Michael J. Bickerdike, NNZ-2566: A Gly-Pro-Glu analogue with neuroprotective efficacy in a rat model of acute focal stroke, Journal of Neurological Sciences 278 (2009) 85-90.
Ozlem Bozdagi, Haploinsufficiency of the autism-associated Shank3 gene leads to deficits in synaptic function, social interaction, and social communication, Molecular Autism 2010, 1:15.
Ozlem Bozdagi, Insulin-like growth factor-1 rescues synaptic and motor deficits in a mouse model of autism and developmental delay, Molecular Autism 2013, 4:9.
Clara M. Cheng, Insulin-like growth factor 1 Is Essential for Normal Dendritic Growth, Journal of Neuroscience Research 73:1-9 (2003).
Philippe Couvert, MECP2 is highly mutated in X-linked mental retardation, Human Molecular Genetics, 2001, vol. 10, No. 9. 941-946.
Mark R. Etherton, Mouse neurexin-1 deletion causes correlated electrophysiological and behavioral changes consistent with cognitive impairments, Howard Hughes Medical Insitute, 17998-18003, Oct. 20, 2009, vol. 106, No. 42.

(Continued)

*Primary Examiner* — Dennis J Parad
(74) *Attorney, Agent, or Firm* — D. Benjamin Borson; Borson Law Group, PC

(57) ABSTRACT

This invention provides compounds, compositions and methods for treating Autism Spectrum Disorders (ASD) using glycyl-2-methylprolyl-glutamic acid (G-2-MePE) and analogs thereof. Autism Spectrum Disorders include Autism, Autistic Disorder, Asperger Syndrome, Childhood Disintegrative Disorder, Pervasive Developmental Disorder—Not Otherwise Specified (PDD-NOS), Fragile X Syndrome, and Rett Syndrome. Compositions containing compounds include water-soluble formulations, water-in-oil micro-emulsions, water-in-oil coarse emulsions, water-in-oil liquid crystals, nanocapsules, tablets, and orally administered gels. The compounds and compositions of this invention can be administered intravenously, intraventricularly, parenterally, or orally, and can be effective in treating neurodegeneration, promoting neurological function, treating seizure activity and other symptoms of ASD, and can prolong life in animals including human beings having Autism Spectrum Disorders.

7 Claims, 26 Drawing Sheets
(2 of 26 Drawing Sheet(s) Filed in Color)

(56) References Cited

OTHER PUBLICATIONS

Stephanie Jamain, Reduced social interaction and ultrasonic communication in a mouse model of monogenic heritable autism, 1710-1715, PNAS, Feb. 5, 2008, vol. 105, No. 5.

Xi-Chun M. Lu, NNZ-2566, a glypromate analog, annténuates brain ischemia-induced nonconvulsive seizures in rats, Journal of Cerebral Blood Flow & Metabolism (2009) 1-9.

Marla C. N. Marchetto, A model for neural development and treatment of Rett Syndrome using human induced pluripotent stem cells, NIH Public Access, Cell, Nov. 12, 2010, 143(4): 527-529.

Neuren Pharmaceuticals, Annual General Meeting May 2011.

Neuren Pharmaceuticals. Limited, Interim Report 2010.

Daniela Tropea, Partial reversal of Rett Syndrome-like symptoms in MeCP2 mutant mice, Massachusetts Institute of Technology, PNAS, Feb. 10, 2009, vol. 106, No. 6.

Hans H. Wei, NNZ-2566 treatment inhibits neuroinflammationa nd pro-inflammatory cytokine expression induced by experimental penetrating ballistic-like brain injury in rats, Journal of Neuroinflammation 6:19, BioMed Central, Aug. 5, 2009.

\* cited by examiner

I. MODIFY GLYCINE RESIDUE

II. MODIFY GLUTAMIC ACID RESIDUE i. α-carboxylic acid residue
ii. γ-carboxylic acid residue
iii. GPE diesters

III. MODIFY PEPTIDE LINKAGES i. modify Pro - α-methylproline
ii. modify Glu - N-Methylglutamic acid
   α-Methylglutamic acid

TREATMENT OF RETT SYNDROME USING GLYCYL-L-2-METHYLPROLYL-L-GLUTAMIC ACID

CLAIM OF PRIORITY

This application is a Continuation filed under 35 U.S.C. 120 of U.S. application Ser. No. 13/699,087, filed Jun. 5, 2013, which is a United States 371 National Phase application of PCT/US2012/000047, entitled "Treatment of Autism Spectrum Disorders Using Glycyl-L-2-Methylprolyl-L-Glutamic Acid," filed 27 Jan. 2012, which claims priority to U.S. Provisional Patent Application No. 61/462,141 entitled "Rett Syndrome Therapy Using Glycyl-2-Methylprolyl-L-Glutamate," Larry Glass et al., inventors, filed 27 Jan. 2011, and to U.S. Provisional Patent Application No. 61/492,248 entitled "Treatment of Autism Spectrum Disorders Using Glycyl-2-L-Methylprolyl-L-Glutamate," Michael John Bickerdike et al. inventors, filed 1 Jun. 2011. Each of these applications is incorporated herein fully by reference as if separately so incorporated.

FIELD OF THE INVENTION

This invention relates generally to therapy of Autism Spectrum Disorders (ASD), including autism, Fragile X Syndrome, Rett Syndrome (RTT), Autistic Disorder, Asperger Syndrome, Childhood Disintegrative Disorder and Pervasive Developmental Disorder Not Otherwise Specified (PDD-NOS), and Pathological Demand Avoidance (PDA). In particular, this invention relates to treatment of ASD using Glycyl-2-methyl-Prolyl-Glutamate (G-2-MePE).

BACKGROUND

Description of Related Art

Autism Spectrum Disorders are becoming increasingly diagnosed. Autism spectrum disorders (ASD) are a collection of linked developmental disorders, characterized by abnormalities in social interaction and communication, restricted interests and repetitive behaviours. Current classification of ASD recognises five distinct forms: classical autism or Autistic Disorder, Asperger syndrome, Rett syndrome, childhood disintegrative disorder and pervasive developmental disorder not otherwise specified (PDD-NOS). A sixth syndrome, pathological demand avoidance (PDA), is a further specific pervasive developmental disorder.

EP 0 366 638 discloses GPE (a tri-peptide consisting of the amino acids Gly-Pro-Glu) and its di-peptide derivatives Gly-Pro and Pro-Glu. EP 0 366 638 discloses that GPE is effective as a neuromodulator and is able to affect the electrical properties of neurons.

WO95/172904 discloses that GPE has neuroprotective properties and that administration of GPE can reduce damage to the central nervous system (CNS) by the prevention or inhibition of neuronal and glial cell death.

WO 98/14202 discloses that administration of GPE can increase the effective amount of choline acetyltransferase (ChAT), glutamic acid decarboxylase (GAD), and nitric oxide synthase (NOS) in the central nervous system (CNS).

WO99/65509 discloses that increasing the effective amount of GPE in the CNS, such as by administration of GPE, can increase the effective amount of tyrosine hydroxylase (TH) in the CNS to increase TH-mediated dopamine production in the treatment of diseases such as Parkinson's disease.

WO02/16408 discloses certain GPE analogs having amino acid substitutions and certain other modification that are capable of inducing a physiological effect equivalent to GPE within a patient. The applications of the GPE analogs include the treatment of acute brain injury and neurodegenerative diseases, including injury or disease in the CNS.

SUMMARY

There is no current, effective, treatment of ASD and patient care is limited to management of the symptoms.

This invention relates to synthetic analogs and peptidomimetics of glycyl-L-prolyl-L-glutamic acid (GPE). In particular, this invention relates to GPE analogs and peptidomimetics that are anti-apoptotic and anti-necrotic, to methods of making them, to pharmaceutical compositions containing them, and to their use to enhance cognitive function and/or treat memory disorders and to improve neuronal connectivity in animals. More specifically, this application relates to the methods of use of the GPE analog, G-2Methyl-Prolyl-Glutamic acid (G-2-MePE) in the treatment of ASD.

The U.S. Pat. No. 7,041,314 discloses compositions of matter and methods of use of G-2-MePE In one aspect, this invention provides compounds of Formula 1 and Formula 2:

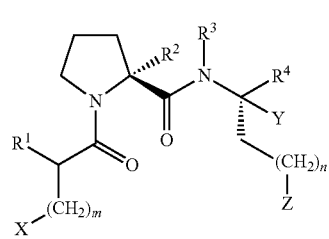

Formula 1

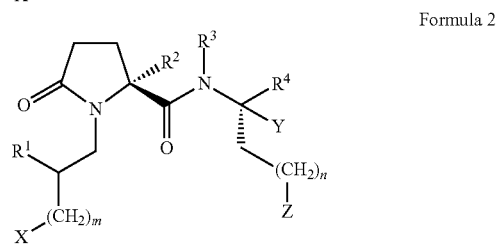

Formula 2 where m is 0 or 1;
n is 0 or 1;
X is H or —NR⁶R⁷;
Y is H, alkyl, —CO₂R⁵, or —CONR⁶R⁷;
Z is H, alkyl, —CO₂R⁵ or —CONR⁶R⁷;
R¹ is H, alkyl, or aralkyl;
R², R³, and R⁴ are independently H or alkyl;
each R⁵ is independently H, alkyl, or a fatty alcohol residue;
each R⁶ and R⁷ is independently H, alkyl, or aralkyl, or
—NR⁶R⁷ is pyrrolidino, piperidino, or morpholino;
or a lactone formed when a compound where Y is —CO₂(alkyl) and Z is —CO₂H or where Y is —CO₂H and Z is —CO₂(alkyl) is lactonized;
and the pharmaceutically acceptable salts thereof,
provided that the compound is not GPE, N-Me-GPE, GPE amide, APE, GPQ or a salt thereof.

Another aspect the invention provides methods for treatment of an animal having a Autism Spectrum Disorder comprising administration of an effective amount of Glycyl-L-2-Methylprolyl-L-Glutamic Acid (G-2-MePE) to the animal.

BRIEF DESCRIPTION OF THE DRAWINGS

Color Drawings

The patent or application file contains at least one drawing executed in color. Copies of this patent or patent application publication with color drawing(s) will be provided by the Office upon request and payment of the necessary fee.

Figure 1:
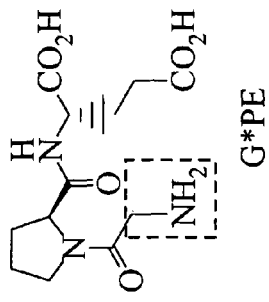
Figure 1:
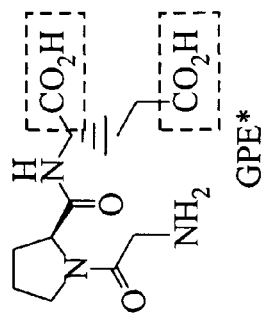
Figure 1:
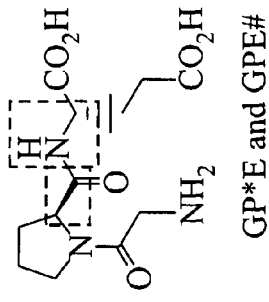

This invention is described with reference to specific embodiments thereof. Other aspects and features of this invention can be understood with reference to the Figures, in which:

FIG. 1 is a general scheme for preparation of synthetic analogs of GPE of the invention.

Figure 2:
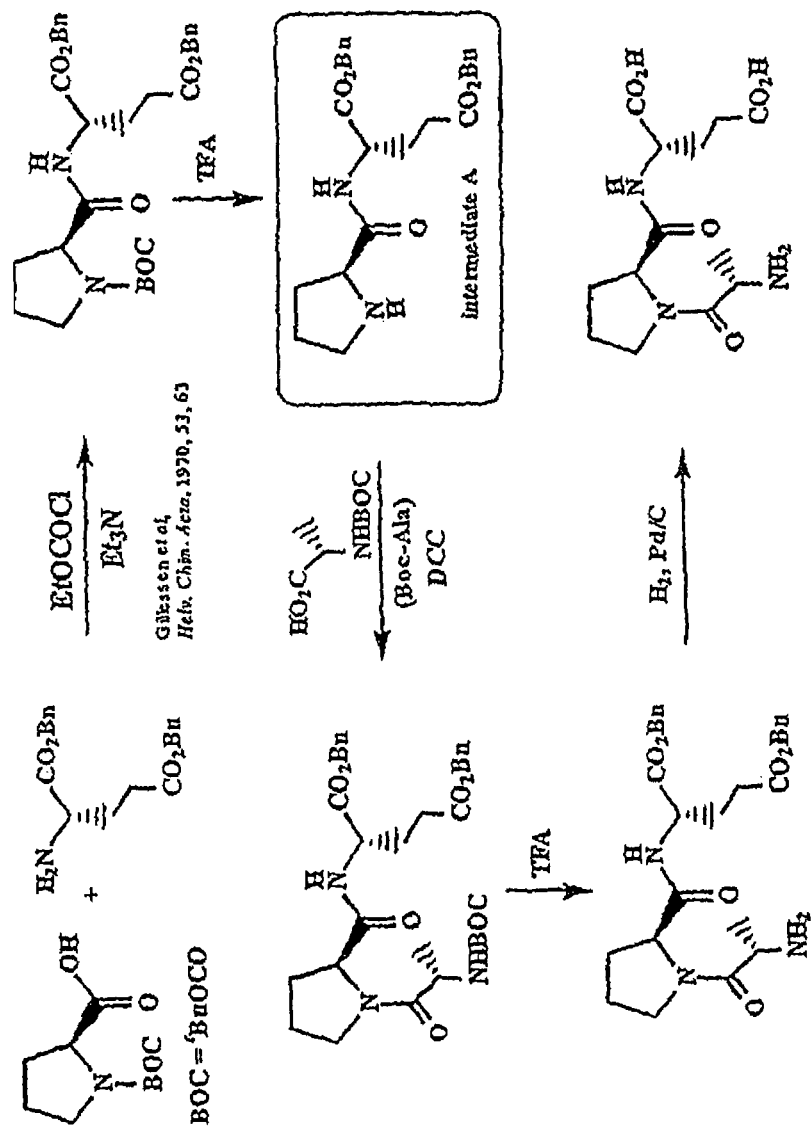
Figure 3:
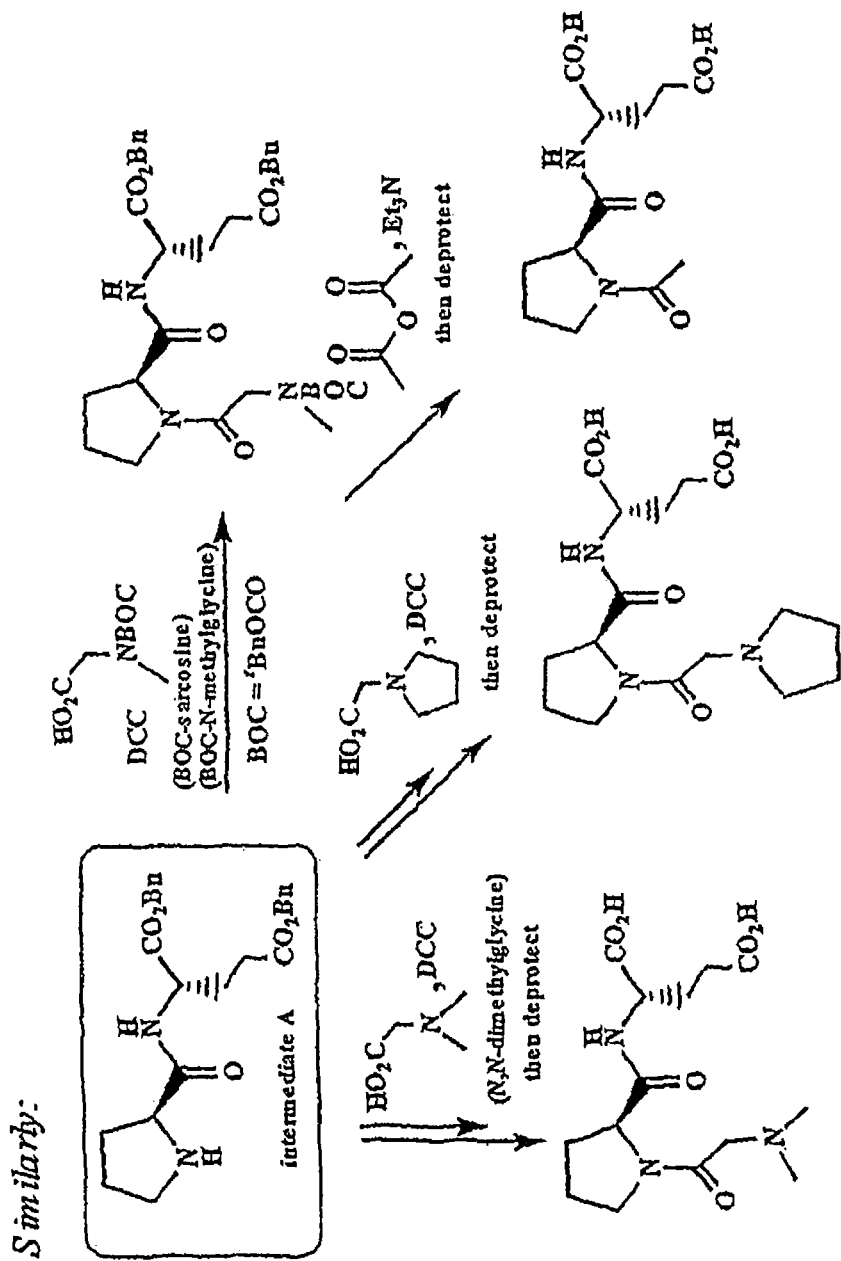
Figure 4:
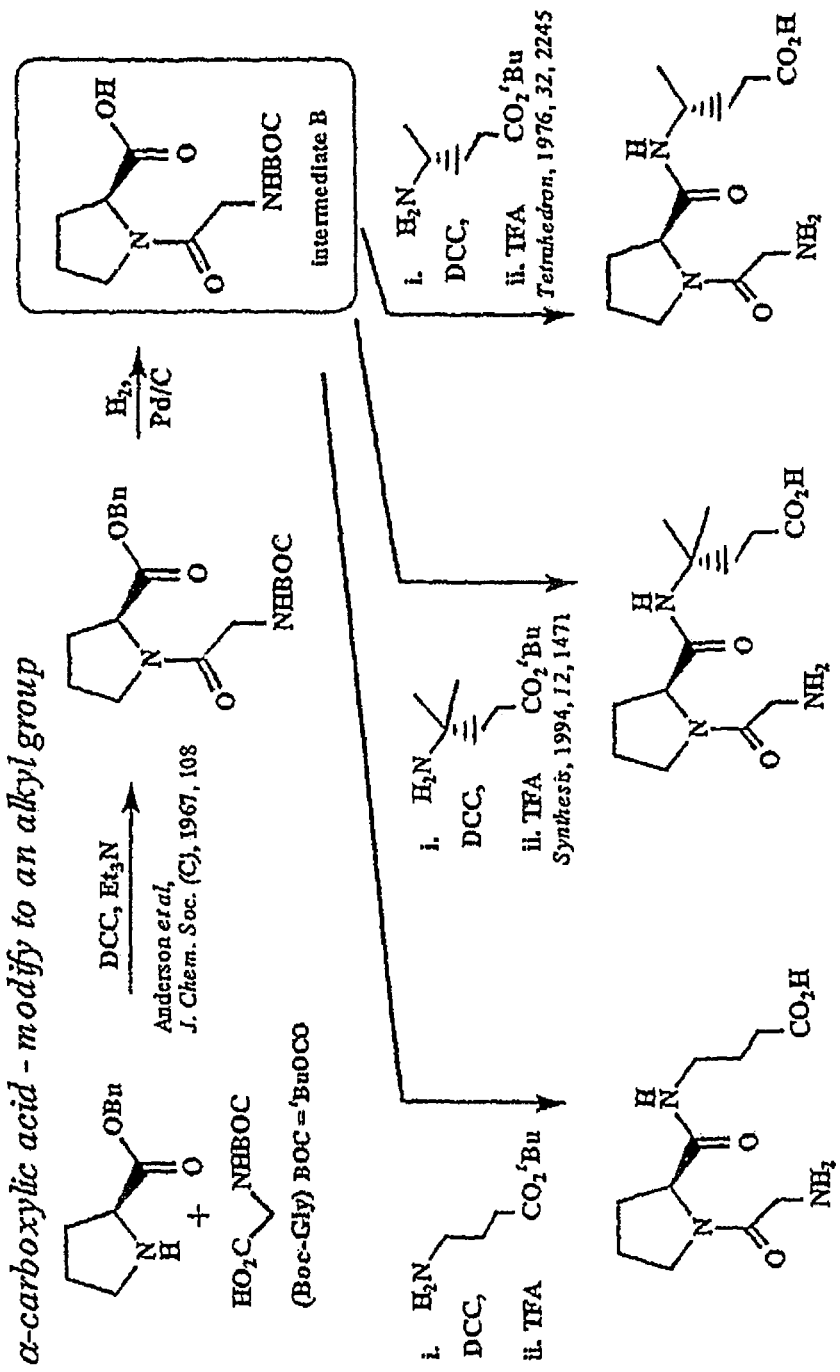
Figure 5:
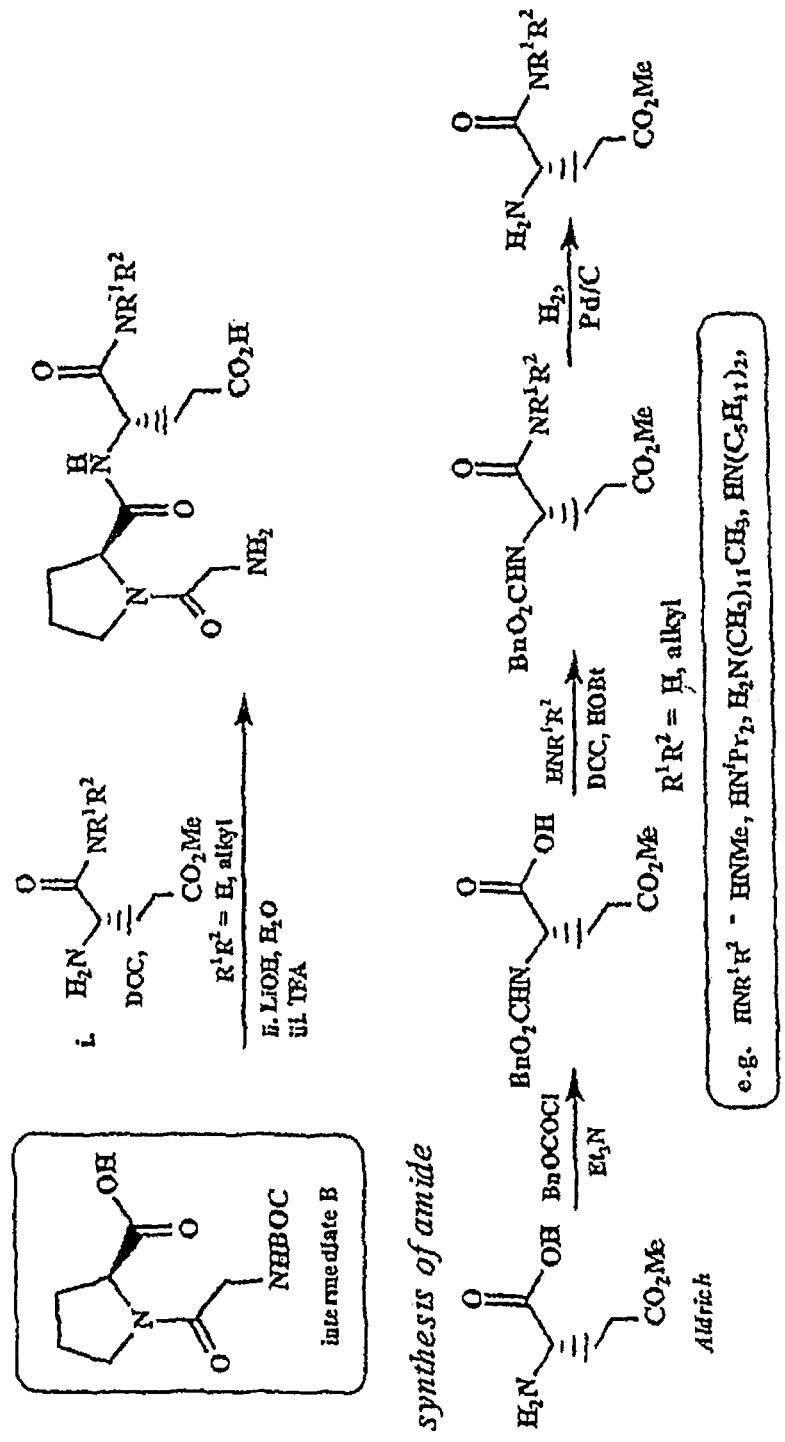
Figure 6:
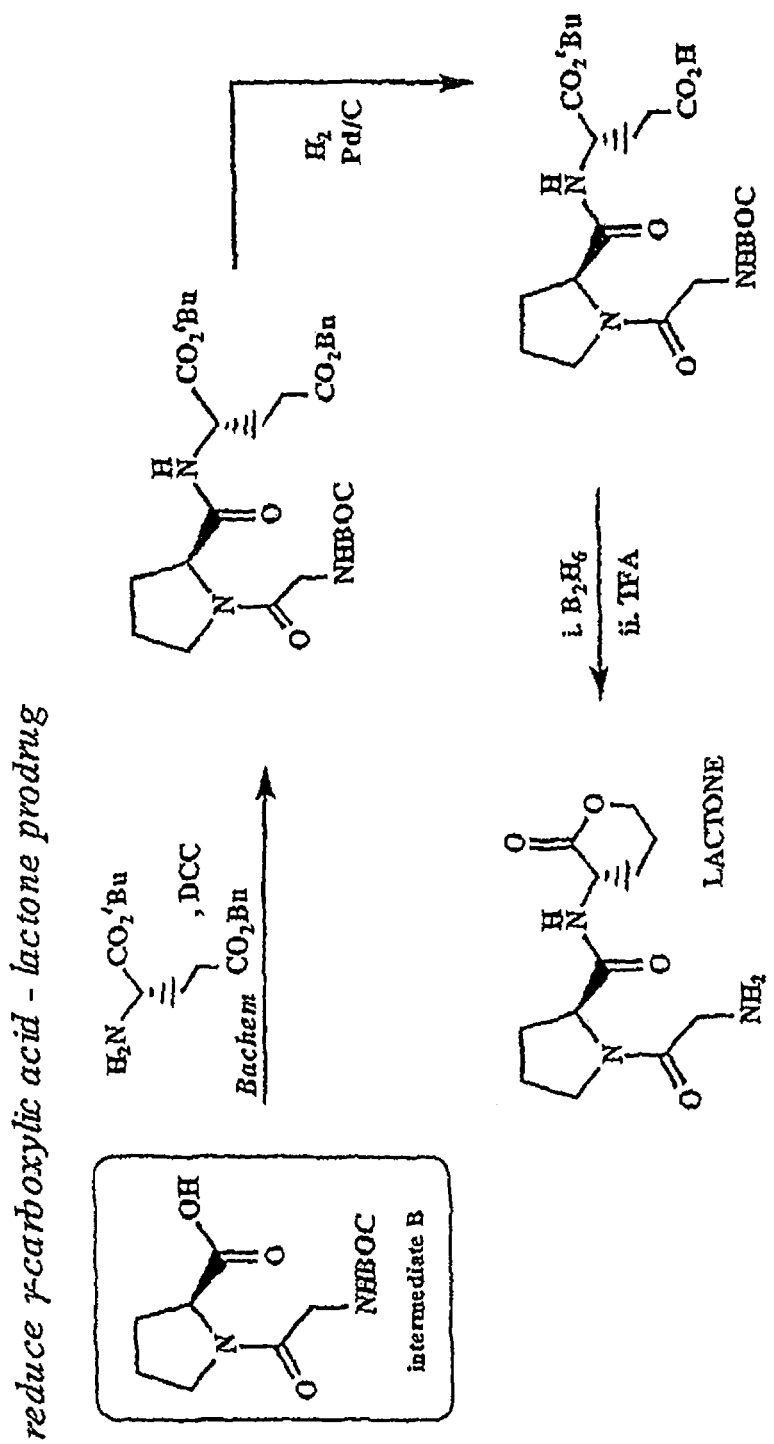
Figure 7:
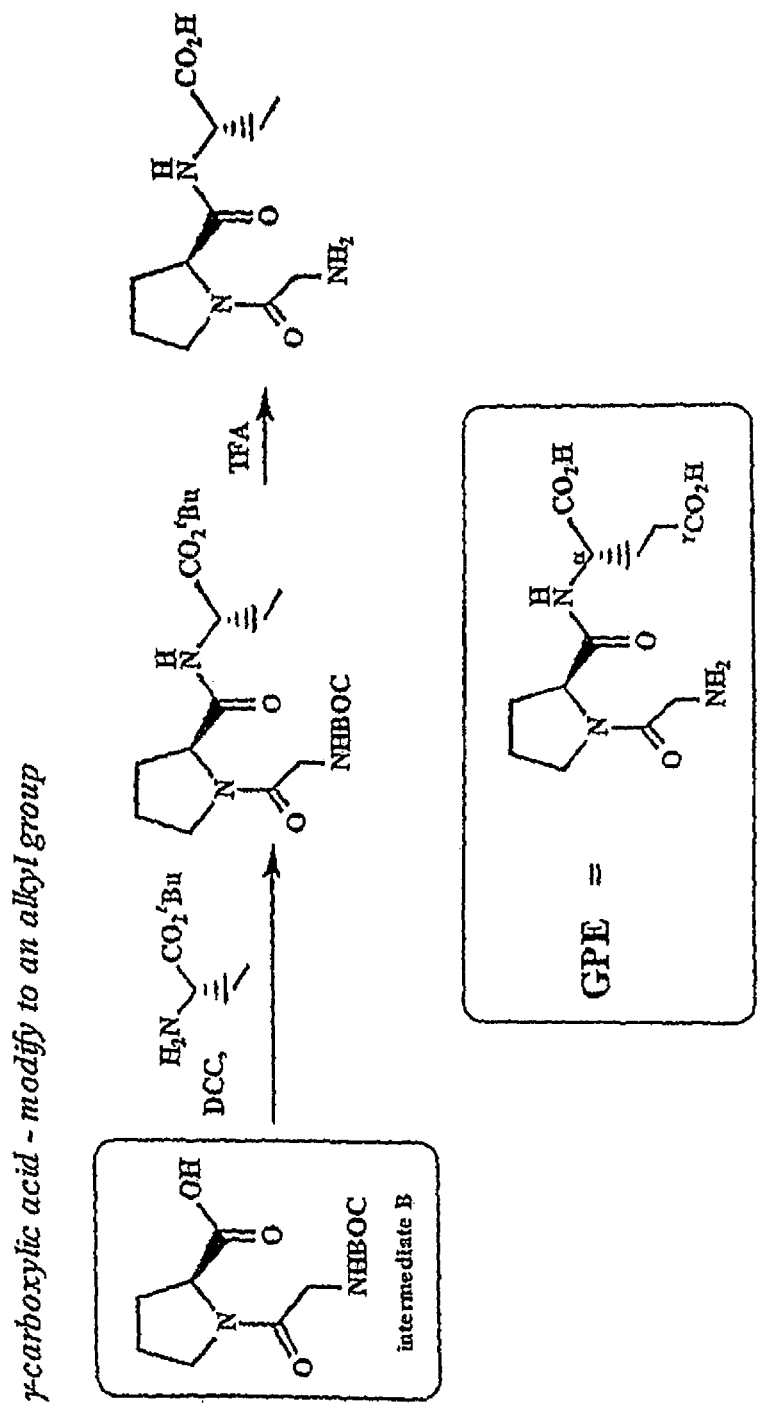
Figure 8:
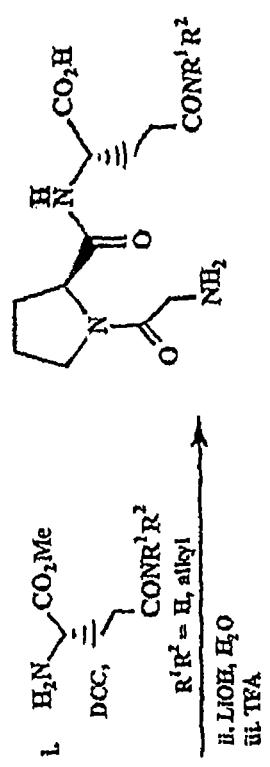
Figure 8:
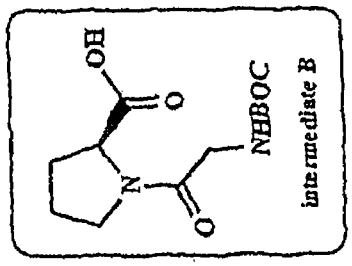
Figure 8:
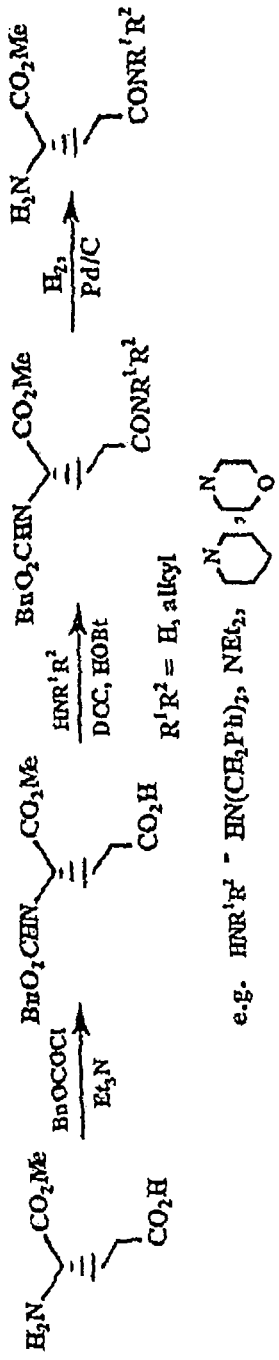
Figure 9:
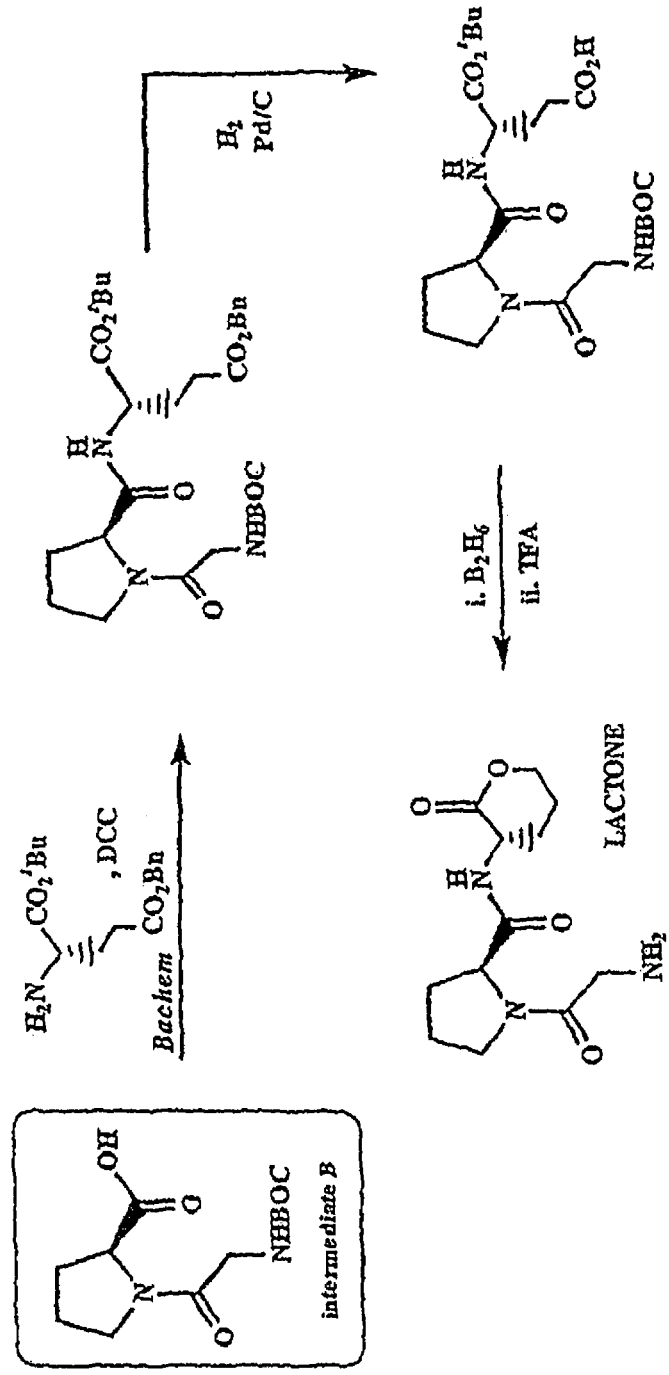

FIGS. 2 and 3 depict schemes for modifying glycine residues on GPE.

FIGS. 4 through 9 depict schemes for modifying glutamic acid residues of GPE.

Figure 10:
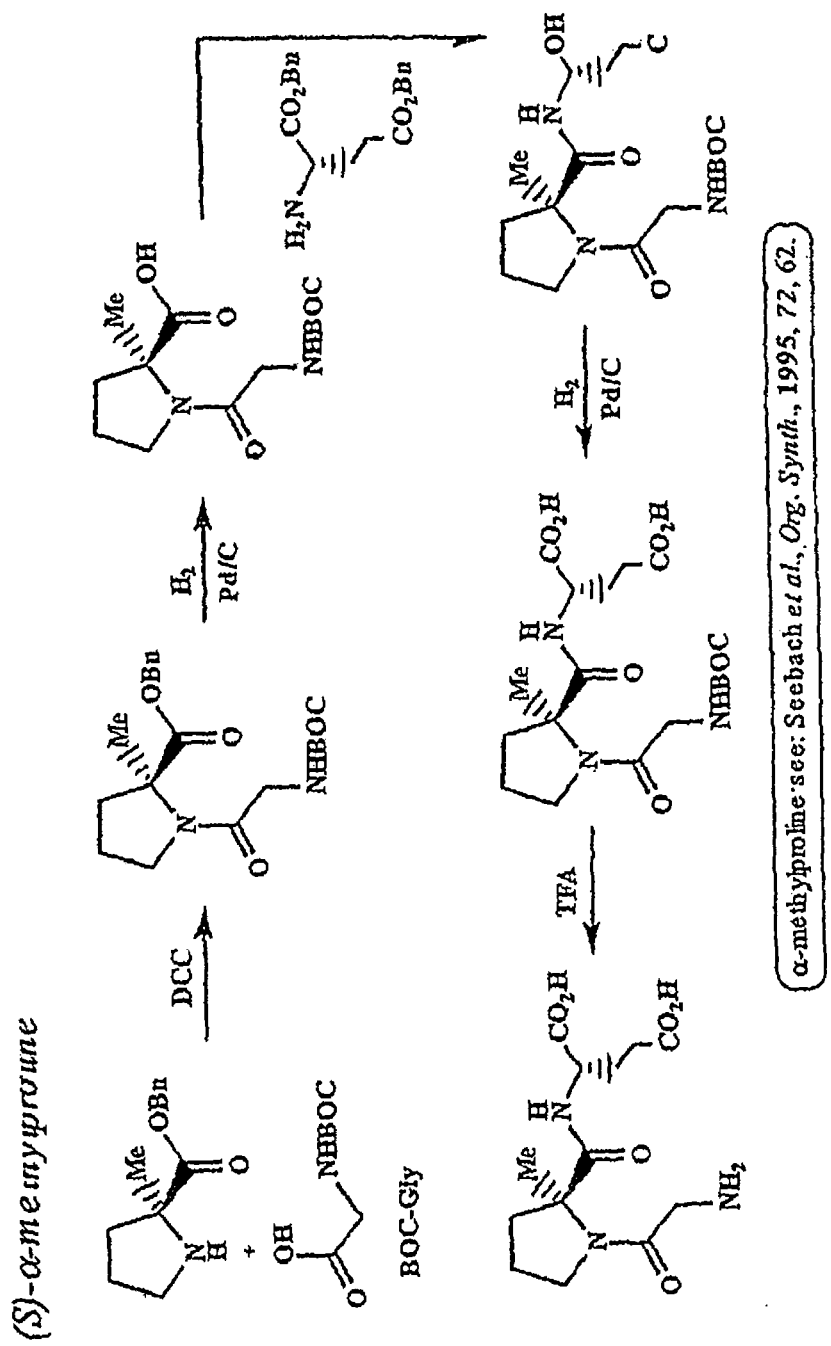
Figure 11:
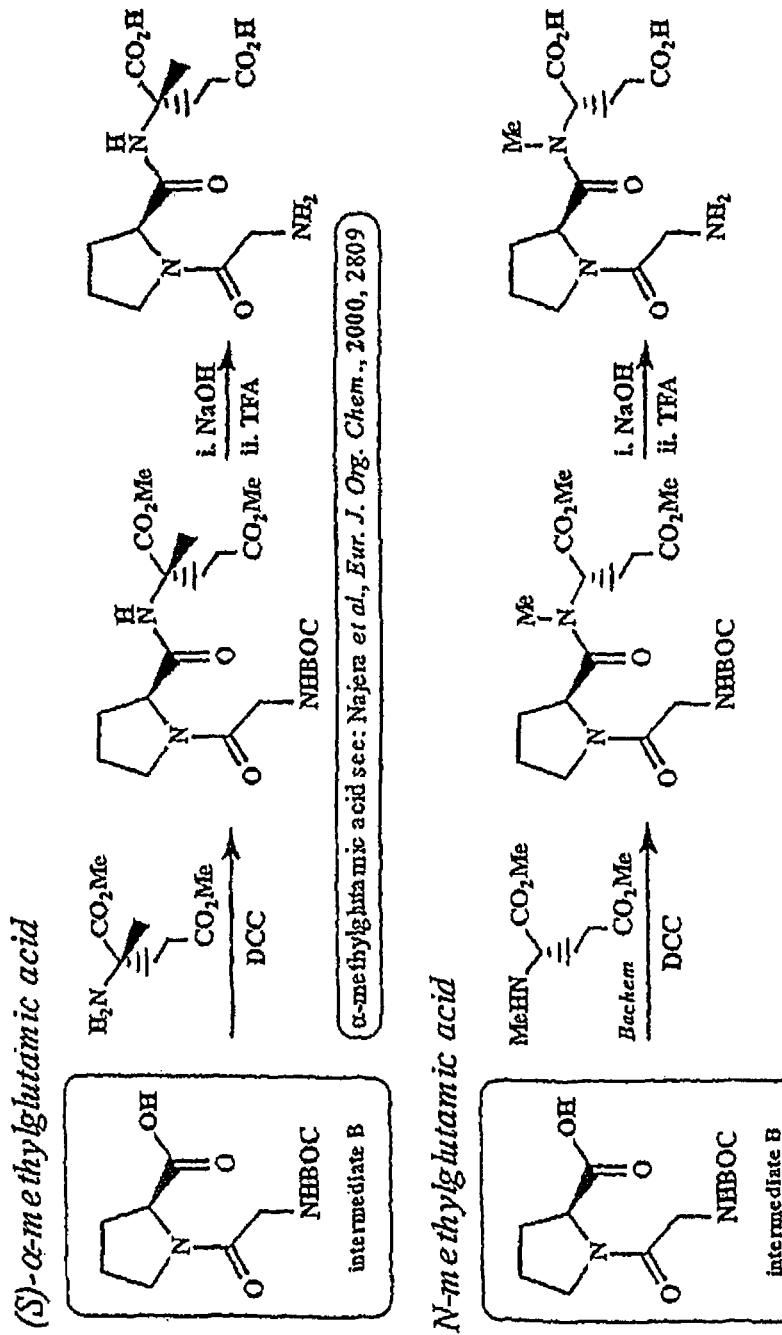

FIGS. 10 and 11 depict schemes for modifying peptide linkages of GPE.

FIGS. 12-15 depict graphs summarizing results of testing neurons in vitro with GPE or G-2-MePE and okadaic acid.

Figure 12:
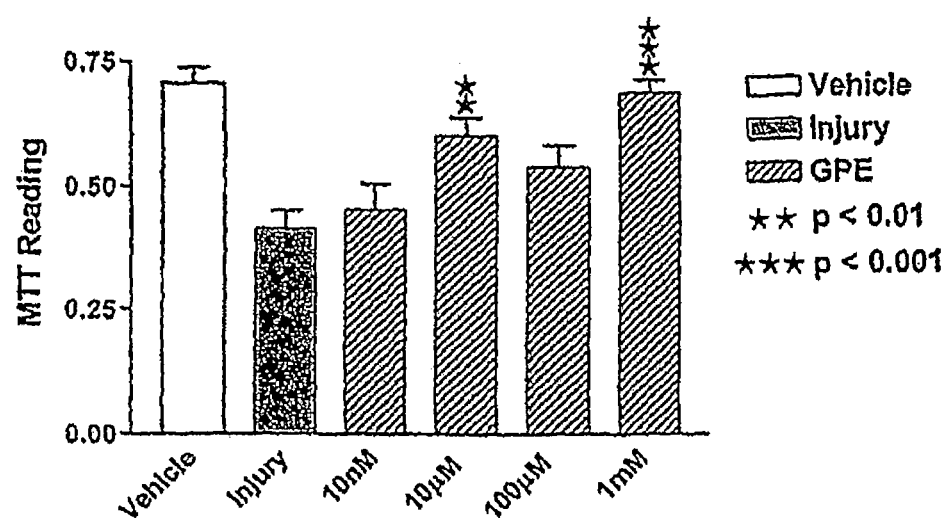

FIG. 12 depicts a graph showing effects of GPE on cortical neurons injured with okadaic acid.

Figure 13:
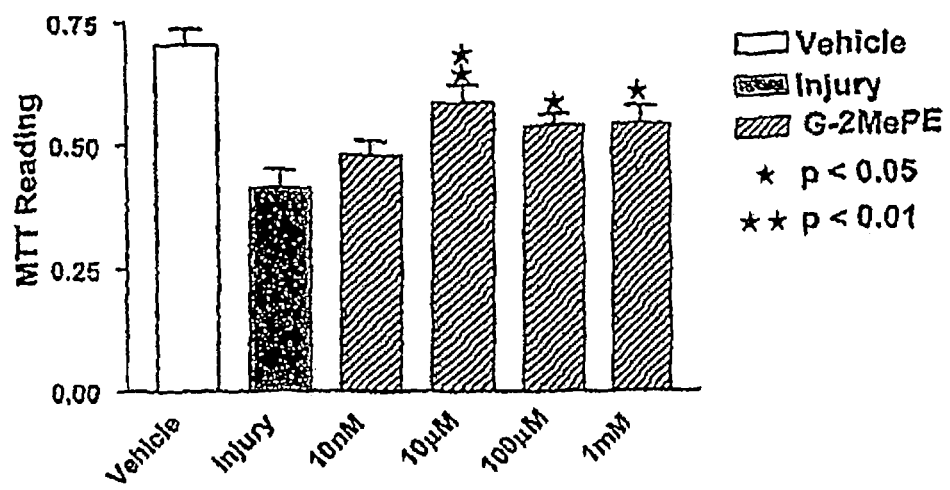

FIG. 13 depicts a graph showing effects of G-2-MePE on cortical neurons injured with okadaic acid.

Figure 14:
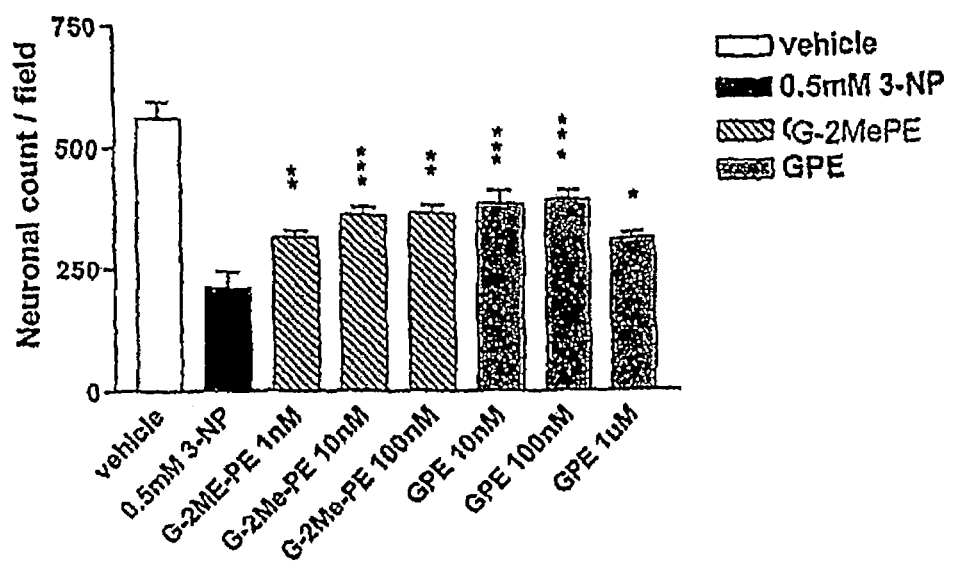

FIG. 14 depicts a graph showing effects of G-2-MePE, GPE on cerebellar microexplants injured with okadaic acid.

Figure 15:
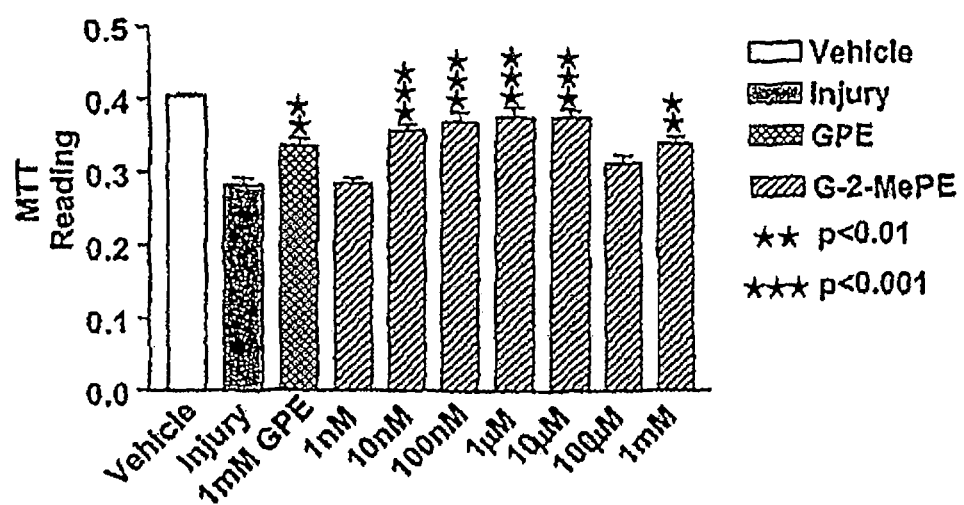

FIG. 15 depicts a graph showing effects of G-2-MePE or GPE on striatal cells injured with okadaic acid.

Figure 16:
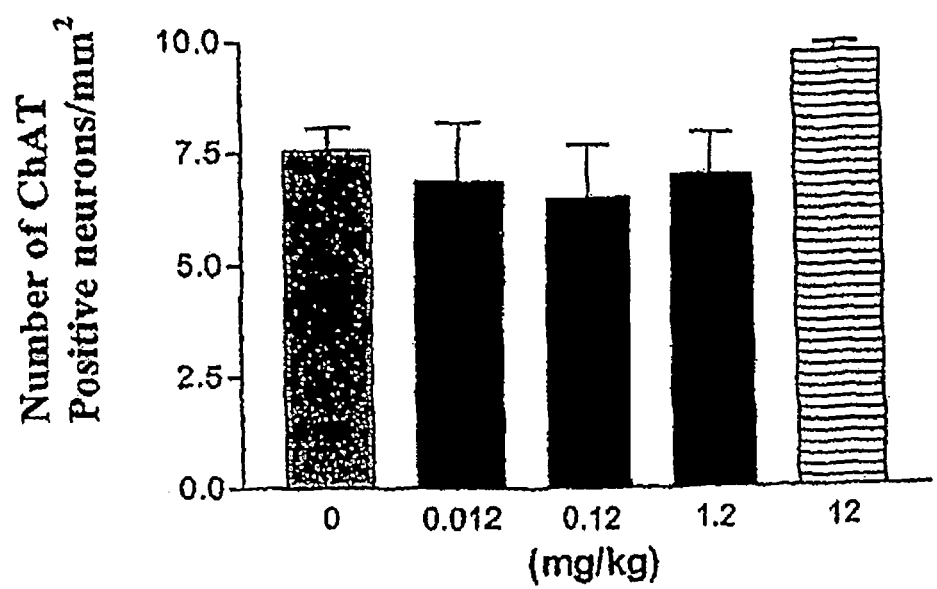

FIG. 16 shows the effects of subcutaneous injection of G-2-MePE (at doses of 0.012, 0.12, 1.2 and 12 mg/kg) on the number of ChAT-positive neurons in the striatum of 18-month old rats.

Figure 17:
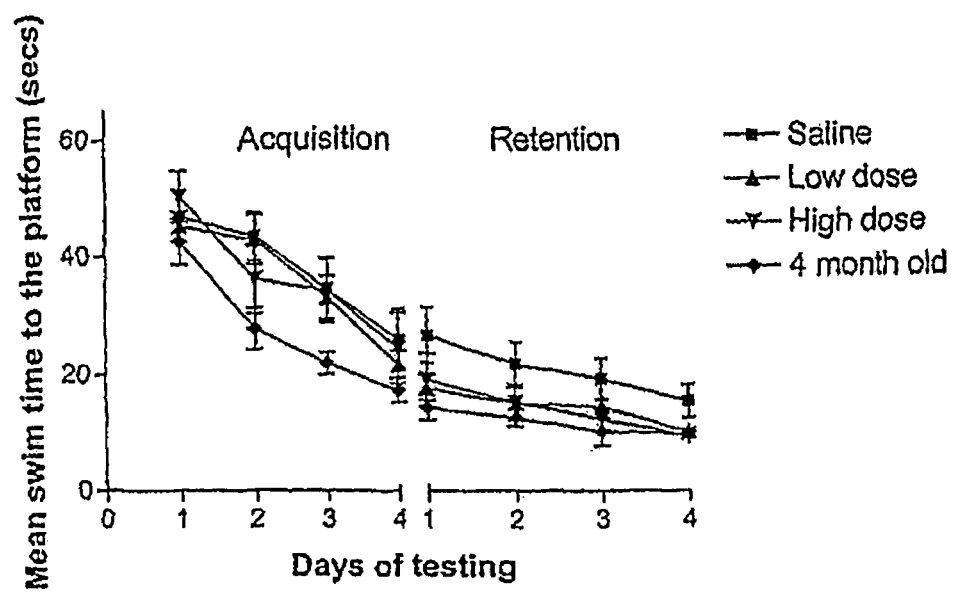

FIG. 17 shows effects of G-2-MePE treatment on spatial memory retention in middle-aged 12-month old rats.

Figure 18A:
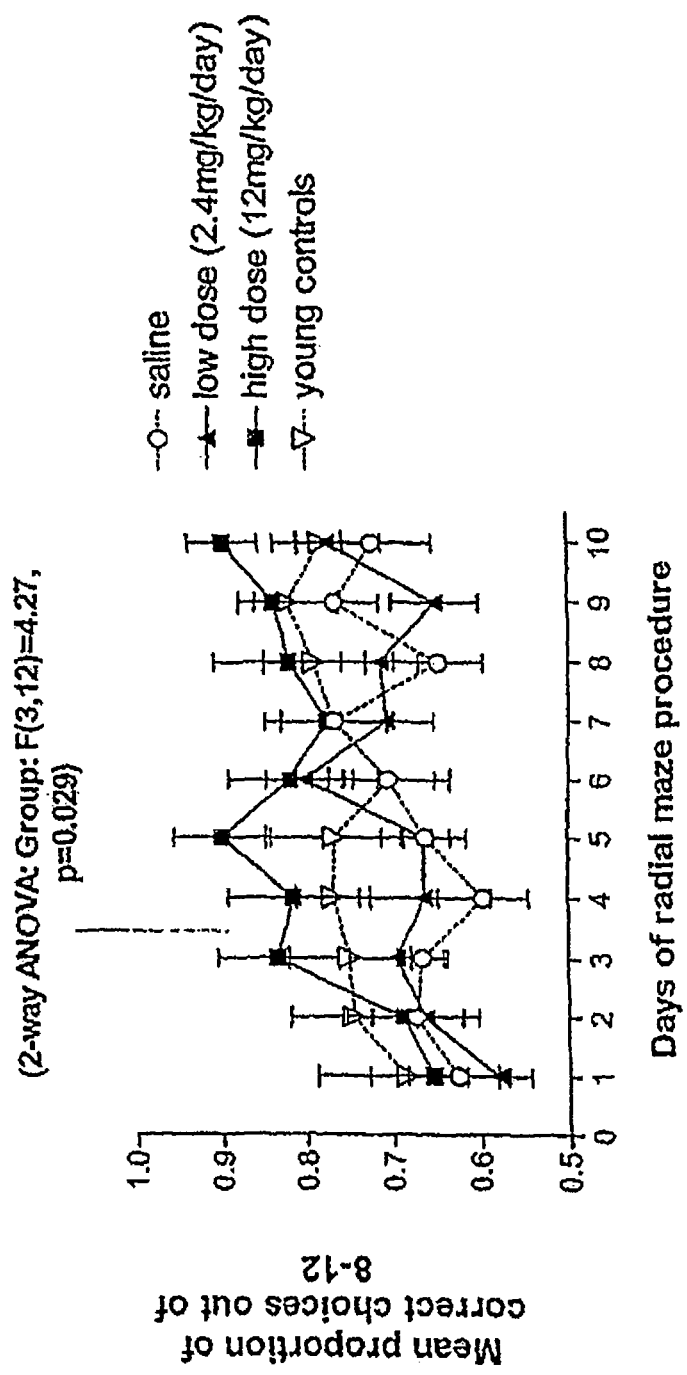
Figure 18B:
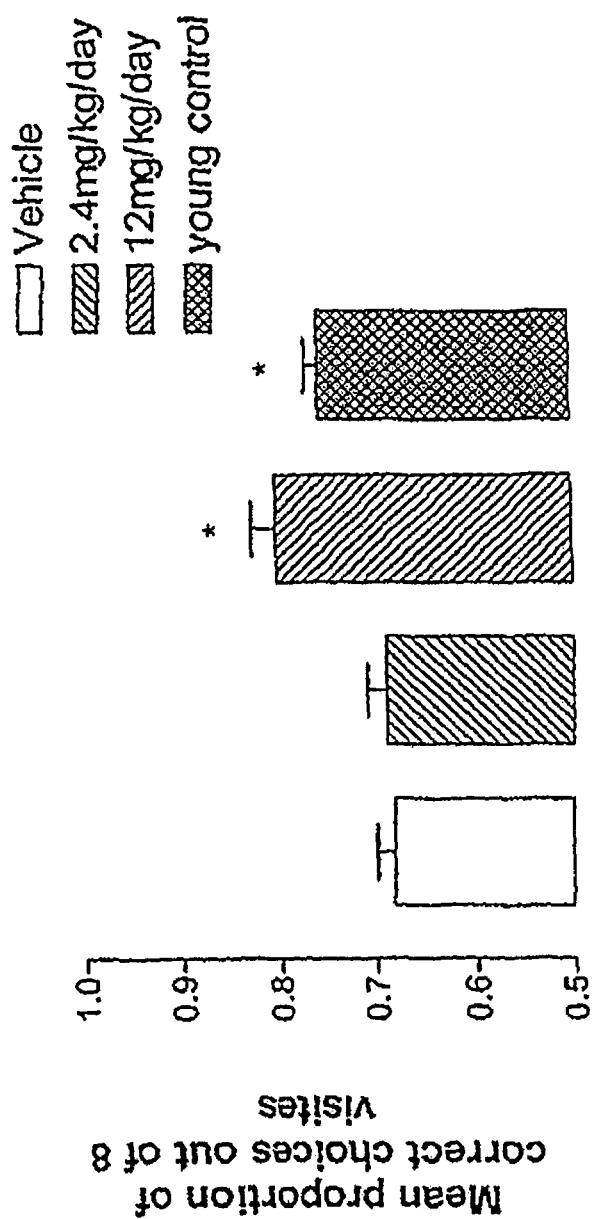

FIGS. 18A and 18B show effects of G-2-MePE on spatial working memory of aged (17-month old) rats in an 8-arm radial maze following 3-weeks of treatment and a nine day washout.

FIG. 18A shows the maze acquisition profiles across days for the different groups. FIG. 18B shows the proportion of correct maze choices averaged across days for the groups.

Figure 19A:
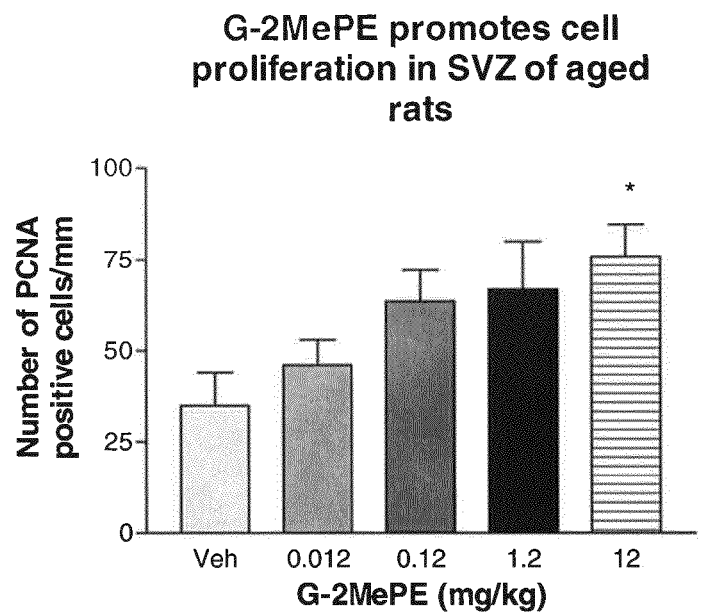

FIG. 19A shows effects of a single intraperitoneal administration of 4 doses of G-2-MePE on neuroblast proliferation as assessed by the number of PCNA positive cells in the subventricular zone (SVZ) of aged rats.

Figure 19B:
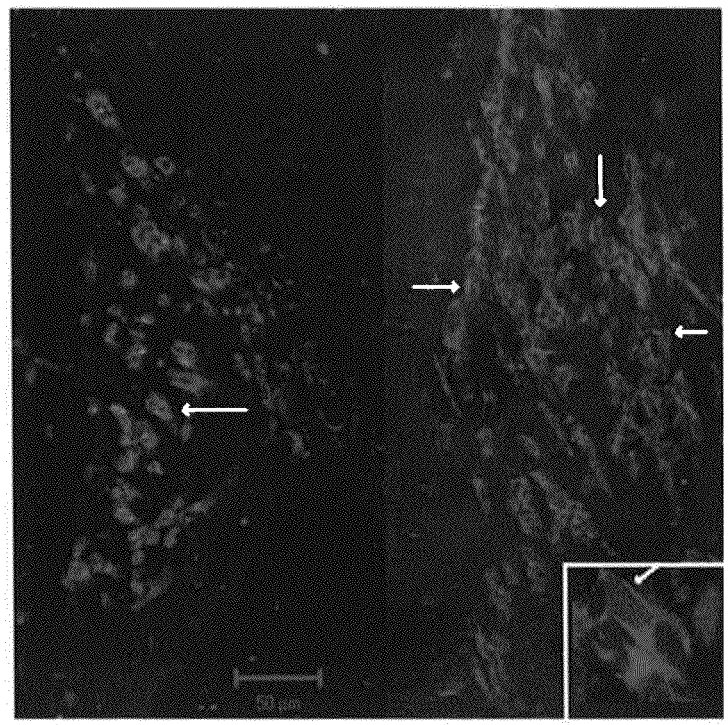

FIG. 19B shows effects of a single intraperitoneal administration of 4 doses of G-2-MePE on co-localisation of PCNA and doublecortin staining in a rat treated with the highest dose of G-2-MePE (right panel) compared to the vehicle treated rat (left panel).

Figure 19C:
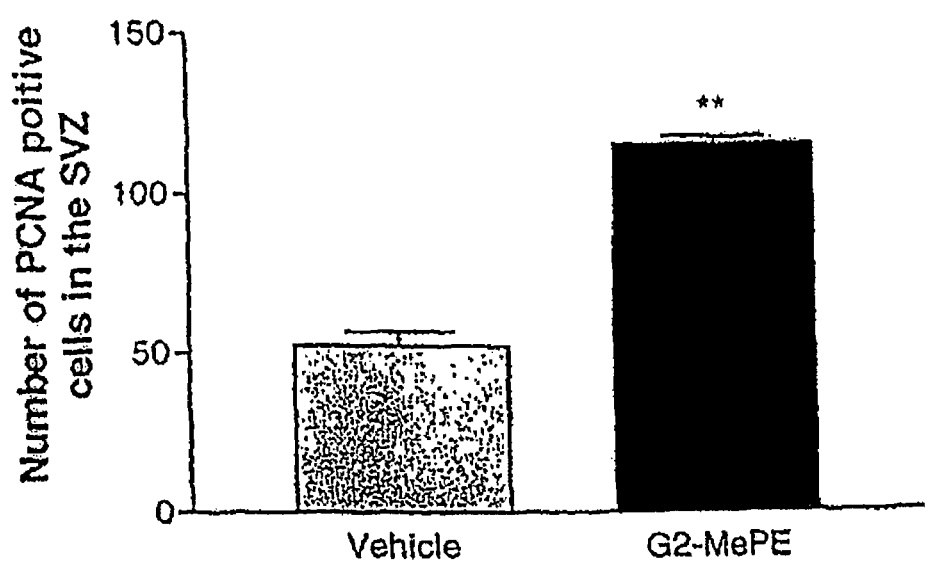

FIG. 19C shows effects of G-2-MePE on neuroblast proliferation as assessed by PCNA immunohistochemical staining in middle-aged rats.

Figure 20A:
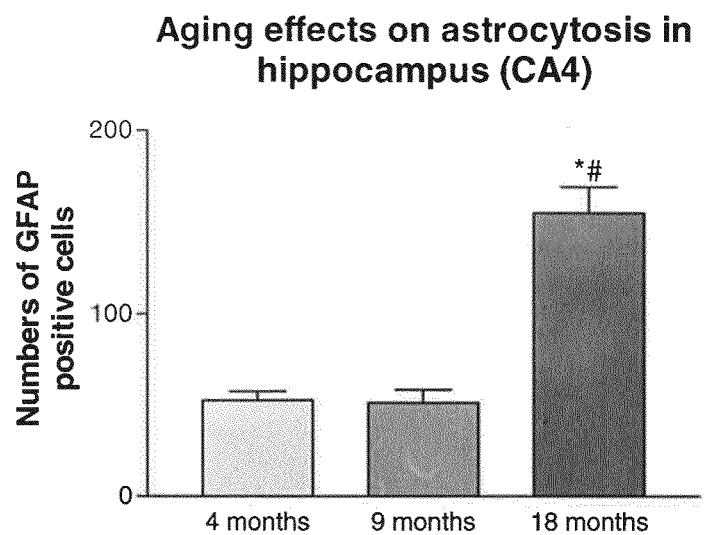

FIG. 20A shows a significant increase in the number of reactive astrocytes as assessed by GFAP staining in the hippocampus in aged rats compared to young rats ($*p<0.01$) and middle aged rats ($*p<0.01$).

Figure 20B:
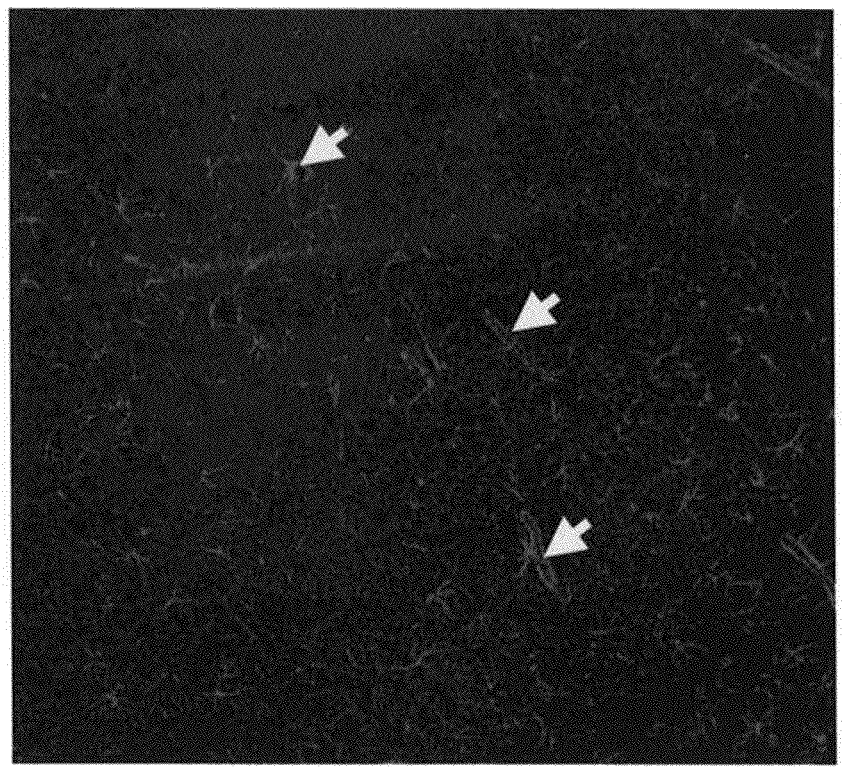

FIG. 20B shows a photograph of a section of cerebral cortex of an aged rat, showing astrocytes as assessed with GFAP staining, some of which are associated with formation of capillaries (arrows).

Figure 20C:
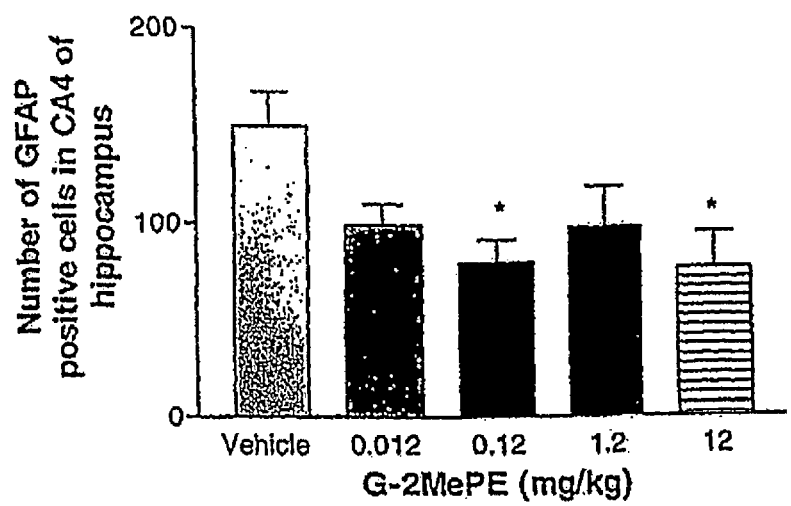

FIG. 20C shows dose-dependent effects of G-2-MePE treatment (at doses of 0.12, 0.12, 1.2 and 12 mg/kg/day) on reduction of the number of astrocytes as assayed using GFAP staining in the CA4 sub-region of the hippocampus in aged rats.

Figure 20D:
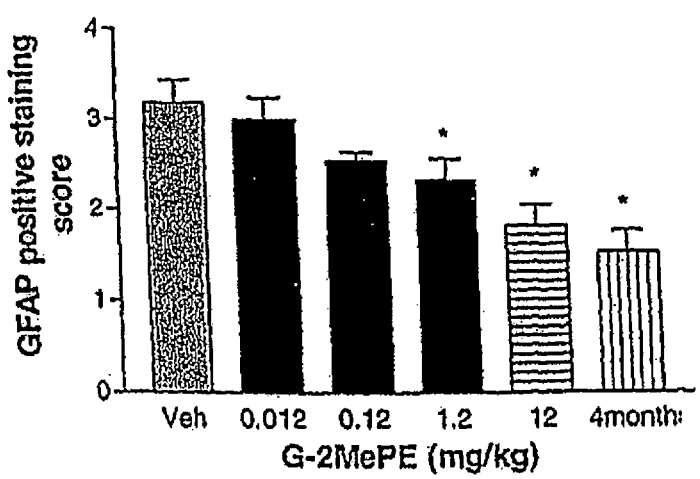

FIG. 20D shows dose-dependent effects of G-2-MePE treatment (at doses of 0.12, 0.12, 1.2 and 12 mg/kg/day) on reduction of the number of astrocytes as assayed using GFAP staining in the cerebellar cortex.

Figure 21:
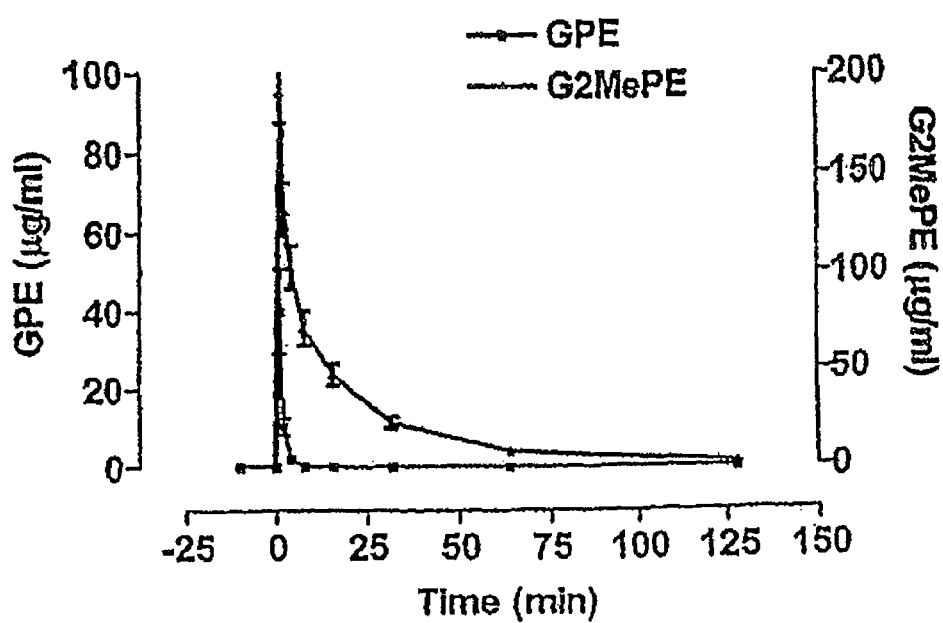

FIG. 21 shows pharmacokinetic properties of GPE and G-2-MePE in the circulation of rats after intravenous injection.

Figure 22:
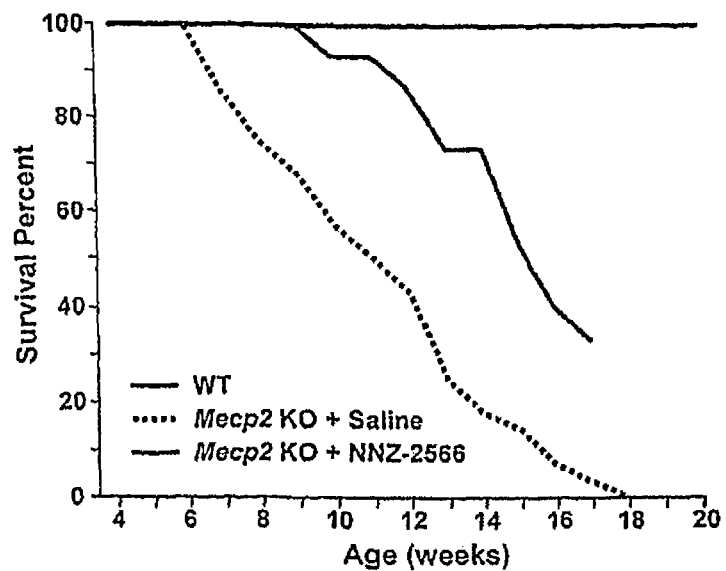

FIG. 22 shows the effects of G-2-MePE on increased survival duration in MeCP2 deficient mice compared to saline-treated MeCP2 deficient mice.

Figure 23:
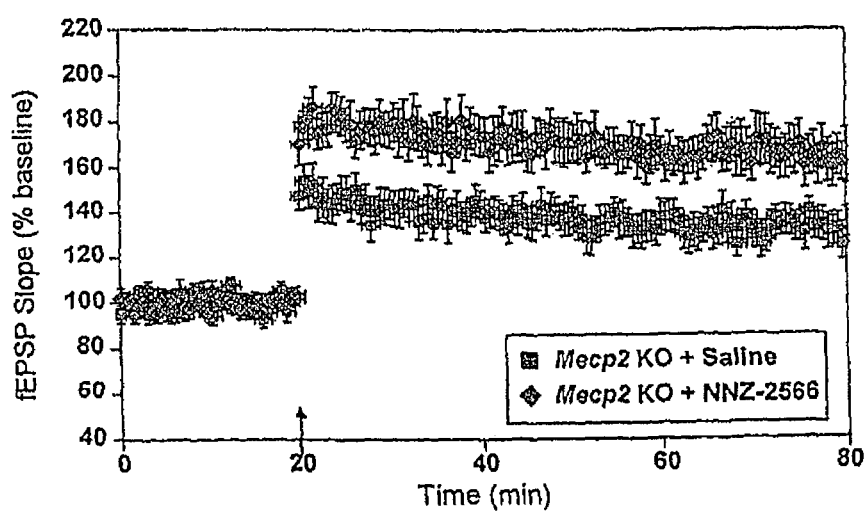

FIG. 23 shows the effects of G-2-MePE on the hippocampal long-term potentiation as measured by the fEPSP slope in MeCP2 deficient mice, compared to saline-treated MeCP2 deficient mice.

Figure 24:
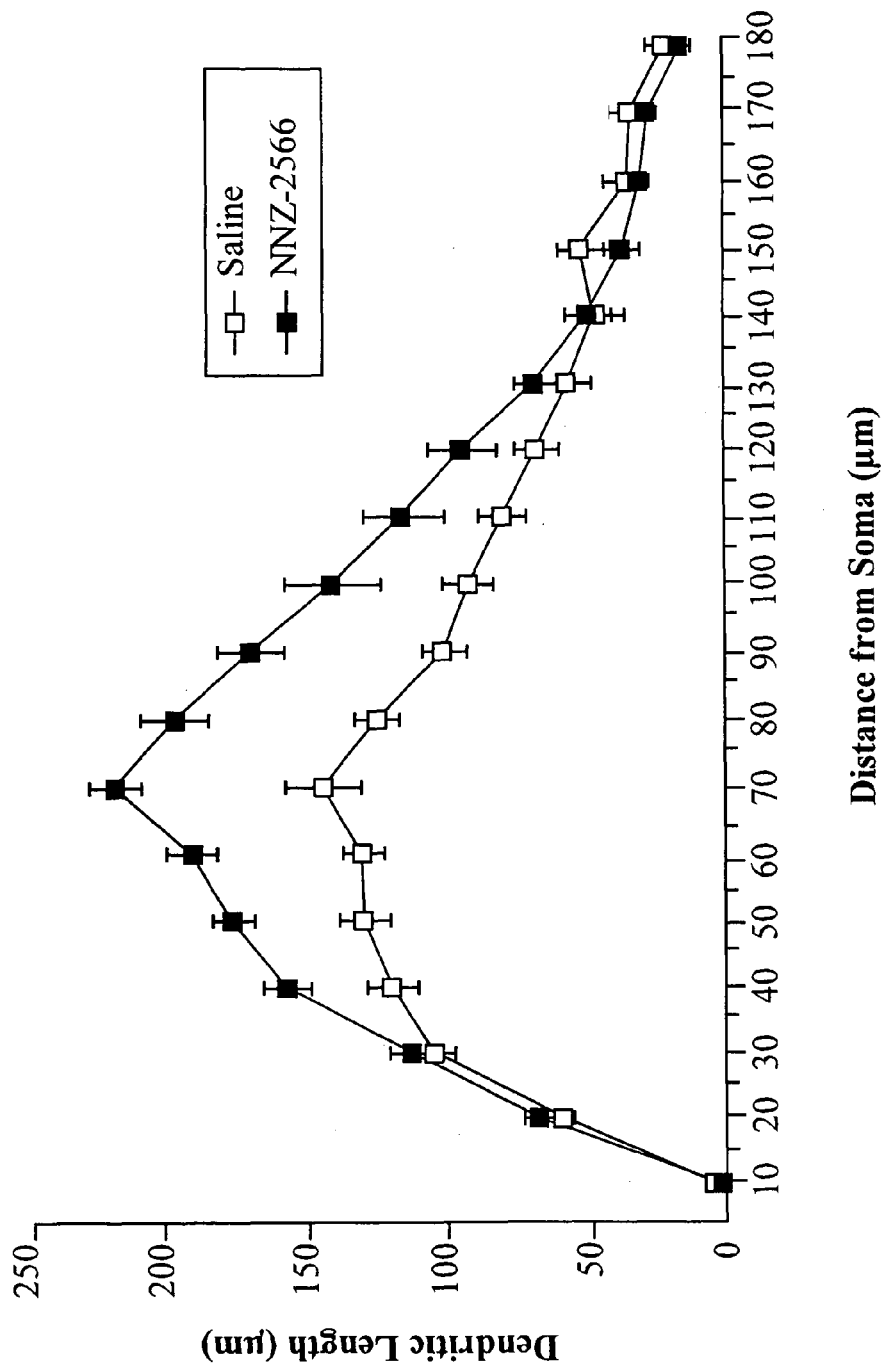

FIG. 24 depicts a graph showing effects of G-2-MePE on dendrite length as a function of distance from the cell soma.

DETAILED DESCRIPTION

Definitions

The term "about" with reference to a dosage or time refers to a particular variable and a range around that variable that is within normal measurement error is within 20% of the value of the variable. The term "about" with reference to a result observed means the variation is within 20% of the value of the observed variable.

The term "alkyl" means a linear saturated hydrocarbyl group having from one to six carbon atoms, or a branched or cyclic saturated hydrocarbyl group having from three to six carbon atoms. Exemplary alkyl groups include straight and branched chain, or cyclic alkyl groups, methyl, ethyl, isopropyl, cyclopropyl, tert-butyl, cyclopropylmethyl, and hexyl.

The term "animal" includes humans and non-human animals, such as domestic animals (cats, dogs, and the like) and farm animals (cattle, horses, sheep, goats, swine, and the like).

The term "aralkyl" means a group of the formula —$(CH_2)_{1-2}$Ar, where Ar is a 5- or 6-membered carbocyclic or heterocyclic aromatic ring, optionally substituted with 1 to 3 substituents selected from Cl, Br, —OH, —O-alkyl, —$CO_2R^8$ (where $R^8$ is H or alkyl), or —$NR^8R^9$, where $R^8$ is as described previously and $R^9$ is H or alkyl. Exemplary aralkyl groups include benzyl, 2-chlorobenzyl, 4-(dimethylamino)benzyl, phenethyl, 1-pyrrolylmethyl, 2-thienylmethyl, and 3-pyridylmethyl.

The term "disease" includes any unhealthy condition of an animal including particularly Parkinson's disease, Huntington's disease, Alzheimer's disease, multiple sclerosis, diabetes, motor disorders, seizures, cognitive dysfunctions due to aging and Autism Spectrum Disorders including autism, Fragile X Syndrome, Rett Syndrome (RTT), Autistic Disorder, Asperger Syndrome, Childhood Disintegrative Disorder and Pervasive Developmental Disorder Not Otherwise Specified (PDD-NOS), and Pathological Demand Avoidance (PDA).

The term "fatty alcohol residue" is a linear hydrocarbyl group having from seven to twenty carbon atoms, optionally containing up to three carbon-carbon double bonds. Exemplary fatty alcohol residues include decyl, pentadecyl, hexadecyl (cetyl), octadecyl (stearyl), oleyl, linoleyl, and eicosyl.

The term "growth factor" means an extracellular polypeptide-signaling molecule that stimulates a cell to grow or proliferate.

The term "injury" includes any acute damage of an animal including non-hemorrhagic stroke, traumatic brain injury, perinatal asphyxia associated with fetal distress such as that following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, cerebral trauma and toxic injury.

"Memory disorders" or "cognitive disorders" are disorders characterized by permanent or temporary impairment or loss of ability to learn, memorize or recall information. Memory disorder can result from normal aging, injury to the brain, tumors, neurodegenerative disease, vascular conditions, genetic conditions (Huntington's disease), hydrocephalus, other diseases (Pick's disease, Creutzfeld-Jakob disease, AIDS, meningitis), toxic substances, nutritional deficiency, biochemical disorders, psychological or psychiatric dysfunctions. The presence of memory disorder in a human can be established thorough examination of patient history, physical examination, laboratory tests, imagining tests and neuropsychological tests. Standard neuropsychological tests include but are not limited to Brief Visual Memory Test-Revised (BVMT-R), Cambridge Neuropsychological Test Automated Battery (CANTAB), Children's Memory Scale (CMS), Contextual Memory Test, Continuous Recognition Memory Test (CMRT), Controlled Oral Word Association Test and Memory Functioning Questionnaire, Denman Neuropsychology Memory Scale, Digit Span and Letter Number Sequence sub-test of the Wechsler Adult Intelligence Scale-III, Fuld Object Memory Evaluation (FOME), Graham-Kendall Memory for Designs Test, Guild Memory Test, Hopkins Verbal Learning Test, Learning and Memory Battery (LAMB), Memory Assessment Clinic Self-Rating Scale (MAC-S), Memory Assessment Scales (MAS), Randt Memory Test, Recognition memory Test (RMT), Rey Auditory and Verbal Learning Test (RAVLT), Rivermead Behavioral Memory Test, Russell's Version of the Wechsler Memory Scale (RWMS), Spatial Working Memory, Test of Memory and Learning (TOMAL), Vermont Memory Scale (VMS), Wechsler Memory Scale, Wide Range Assessment of Memory and Learning (WRAML).

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The term "pharmaceutically acceptable salt" means a salt that is pharmaceutically acceptable and has the desired pharmacological properties. Such salts include salts that can be formed where acidic protons present in the compounds react with inorganic or organic bases. Suitable inorganic salts include those formed with the alkali metals, e.g. sodium and potassium, magnesium, calcium, and aluminum. Suitable organic salts include those formed with organic bases such as amines e.g. ethanolamine, diethanolamine, triethanolamine, tromethamine, N-methylglucamine, and the like. Salts also include acid addition salts formed by reaction of an amine group or groups present in the compound with an acid. Suitable acids include inorganic acids (e.g. hydrochloric and hydrobromic acids) and organic acids (e.g. acetic acid, citric acid, maleic acid, and alkane- and arene-sulfonic acids such as methanesulfonic acid and benzenesulfonic acid). When there are two acidic groups present in a compound, a pharmaceutically acceptable salt may be a mono-acid mono-salt or a di-salt; and similarly where there are more than two acidic groups present, some or all of such groups can be salified. The same reasoning can be applied when two or more amine groups are present in a compound.

The term "protecting group" is a group that selectively blocks one or more reactive sites in a multifunctional compound such that a chemical reaction can be carried out selectively on another unprotected reactive site and such that the group can readily be removed after the selective reaction is complete.

The term "therapeutically effective amount" means the amount of an agent that, when administered to an animal for treating a disease, is sufficient to effect treatment for that disease as measured using a test system recognized in the art.

The term "treating" or "treatment" of a disease may include preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "functional deficit" means a behavioral deficit associated with neurological damage. Such deficits include deficits of gait, as observed in patients with Parkinson's disease, motor abnormalities as observed in patients with Huntington's disease. Functional deficit also includes abnormal foot placement and memory disorders described herein.

The terms "G-2-MePE" and "NNZ-2566" means L-Glycyl-2-methyl-L-Prolyl-L-Glutamate.

The term "seizure" means an abnormal pattern of neural activity in the brain that results in a motor deficit or lack of motor control resulting in abnormal motion, including spasmodic motion. "Seizure" includes electroencephalographic abnormalities, whether or not accompanied by abnormal motor activity.

Implicit hydrogen atoms (such as hydrogen atoms on a pyrrolidine ring, etc.) are omitted from the formulae for clarity, but should be understood to be present.

Autism Spectrum Disorders

Autism spectrum disorders (ASDs) are a collection of linked developmental disorders, characterized by abnormalities in social interaction and communication, restricted interests and repetitive behaviours. Current classification of ASDs recognises five distinct forms: classical autism or Autistic Disorder, Asperger syndrome, Rett syndrome, childhood disintegrative disorder and pervasive developmental disorder not otherwise specified (PDD-NOS). A sixth syndrome, pathological demand avoidance (PDA), is a further specific pervasive developmental disorder. However, while PDA is increasingly recognised as an ASD, it is not yet part of the Diagnostic and Statistical Manual of Mental Disorders (DSM-IV), published by the American Psychiatric Association, nor is it part of the proposed revision, the DSM-V.

Autism

Classical autism is a highly variable neurodevelopmental disorder. It is typically diagnosed during infancy or early childhood, with overt symptoms often apparent from the age of 6 months, and becoming established by 2-3 years. According to the criteria set out in the DSM-IV, diagnosis of autism requires a triad of symptoms to be present, including (a) impairments in social interaction, (b) impairments in communication and (c) restricted and repetitive interests and behaviours. Other dysfunctions, such as atypical eating, are also common but are not essential for diagnosis. Of these impairments, social interaction impairments are particularly important for diagnosis, and two of the following impairments must be present for a diagnosis of autism:
(i) impairments in the use of multiple nonverbal behaviors (e.g. eye contact) to regulate social interaction;
(ii) failure to develop peer relationships appropriate to developmental level;
(iii) lack of spontaneous seeking to share enjoyment, interests, or achievements;
(iv) lack of social or emotional reciprocity.

Communication impairments in autism may be manifest in one or more of the following ways: delay in (or total lack of) the development of spoken language; marked impairment in the ability to initiate or sustain a conversation; stereotyped and repetitive use of language; and/or a lack of spontaneous make-believe play. Restricted, repetitive and stereotyped patterns of behavior is also required for diagnosis, such as preoccupation with one or more interest considered abnormal in intensity, inflexible adherence to routines or rituals, repetitive motor mannerisms and/or persistent focus on parts of objects.

Lastly, for a diagnosis of autism, it is necessary that the impairment in the functioning of at least one area (i.e. social interaction, language, or imaginative play) should have an onset at less than 3 years of age.

Autism is commonly associated with epilepsy or epileptiform activity in the electroencephalogram (EEG). As many as 60 percent of patients with autism have epileptiform activity in their EEGs (Spence and Schneider, 2009 Ped Res 65: 599-606).

Autism is also associated with disturbances in function of IGF-1, which is depleted in the Central Nervous System (CNS) in patients with autism (Riikonen et al., 2006 Devel Med Child Neurol 48: 751-755). IGF-1 levels in the CNS increase in patients with autism after treatment with agents that reduce symptoms such as fluoxetine (Makkonen et al., 2011 Neuropediatrics 42:207-209).

Importantly, autism shares features of Rett Syndrome and Fragile X Syndrome in relation to neuronal connectivity. All three disorders are characterised by defects in synaptic function and neuronal connectivity. This is reflected in studies of post mortem human brain in these patient groups, which all show failure to form normal synaptic connections. This is reflected in altered morphological characteristics, being either a reduction in neuron dendritic spine density, or enhanced dendritic spine density but associated with immature synapses. This is reflected in animal models of autism, Rett Syndrome and Fragile X Syndrome, which are based on genetic changes known to be pathological in these disorders. In these animal models, neuronal connectivity defects are revealed morphologically, and also as a failure of Long Term Potentiation (LTP). This is important since IGF-1, IGF-1[1-3] and G-2-MePE increase synapse formation.

Asperger Syndrome

Asperger syndrome or Asperger Disorder is similar to autism, and shares certain features. Like autism, Asperger syndrome is also characterized by impairment in social interaction and this is accompanied by restricted and repetitive interests and behavior. Thus, diagnosis of Asperger syndrome is characterized by the same triad of impairments as autism. However, it differs from the other ASDs by having no general delay in language or cognitive development and no deficit in interest in the subject's environment. Moreover, Asperger syndrome is typically less severe in symptomology than classical autism and Asperger's patients may function with self-sufficiency and lead relatively normal lives.

Childhood Disintegrative Disorder

Childhood disintegrative disorder (CDD), also known as Heller syndrome, is a condition in which children develop normally until age 2-4 years (i.e. later than in Autism and Rett syndrome), but then demonstrate a severe loss of social, communication and other skills. Childhood disintegrative disorder is very much like autism and both involve normal development followed by significant loss of language, social play and motor skills. However, childhood disintegrative disorder typically occurs later than autism, involves a more dramatic loss of skills and is far less common.

Diagnosis of CDD is dependent on dramatic loss of previously acquired skills in two or more of the following areas: language, social skills, play, motor skills (such as a dramatic decline in the ability to walk, climb, grasp, etc), bowel or bladder control (despite previously being toilet-trained). The loss of developmental skills may be abrupt and take place over the course of days to weeks or may be more gradual.

Pervasive Developmental Disorder—not Otherwise Specified (PDD-NOS)

Pervasive Developmental Disorder—Not Otherwise Specified (PDD-NOS) is an ASD that describes patients exhibiting some, but not all, of the symptoms associated with other well defined ASDs. The key criteria for diagnosis of an ASD include difficulty socializing with others, repetitive behaviors, and heightened sensitivities to certain stimuli. These are all found in the ASDs described above. However, autism, Asperger syndrome, Rett syndrome and childhood disintegrative disorder all have other features that enable their specific diagnosis. When specific diagnosis of one of these four disorders cannot be made, but ASD is apparent, a diagnosis of PDD-NOS is made. Such a diagnosis may result from symptoms starting at a later age than is applicable for other conditions in the spectrum.

Rett Syndrome

Rett Syndrome (RTT) is a neurodevelopmental disorder that almost exclusively affects females (1 in 10:000 live births). RTT is classified as an autism spectrum disorder (Diagnostic and Statistical Manual of Mental Disorders, Fourth Edition-Revised (DSM-IV-R). Approximately 16,000 patients are currently affected by it in the U.S.A. (Rett Syndrome Research Trust data). For a diagnosis of Rett syndrome, the following symptoms are characteristic: impaired development from age 6-18 months; slowing of the rate of head growth starting from between age 3 months and 4 years; severely impaired language; repetitive and stereotypic hand movements; and gait abnormalities, e.g. toe-walking or unsteady stiff-legged walk. There are in addition, a number of supportive criteria that may help diagnosis of Rett Syndrome, but are not essential for a diagnosis. These include breathing difficulties, EEG abnormalities, seizures, muscle rigidity and spasticity, scoliosis (curving of the spine), teeth-grinding, small hands and feet in relation to height, growth retardation, decreased body fat and muscle mass, abnormal sleep patterns, irritability or agitation, chewing and/or swallowing difficulties, poor circulation and constipation.

The onset of RTT usually begins between 6-18 months of age with a slowing of development and growth rates. This is followed by a regression phase (typically in children aged 1-4 years of age), pseudo-stationary phase (2-10 years of age) and a subsequent progressive late motor deterioration state. RTT symptoms include sudden deceleration of growth and regression in language and motor skills including purposeful hand movements being replaced by stereotypical movements, autistic features, panic-like attacks, sleep cycle disturbances, tremors, seizures, respiratory dysfunctions (episodic apnea, hyperpnea), apraxia, dystonia, dyskinesia, hypotonia, progressive kyphosis or scoliosis and severe cognitive impairment. Most RTT patients survive into adulthood with severe disabilities and require 24-hour-a-day care.

Between 85% and 95% cases of RTT are reported to be caused by a mutation of the Mecp2 gene (Amir et al. 1999. Nat Genet 23:185-188; *Rett Syndrome Research Trust*)—a gene encoding methyl-CpG-binding protein 2 (MeCP2). Mecp2 maps to the X-chromosome (location Xq28) and for this reason, mutations to the gene in males are usually lethal. While RTT is a genetic disorder, less than 1% of recorded cases are inherited; almost all mutations of Mecp2 occur de novo, with two thirds caused by mutations at 8 CpG dinucleotides (R106, R133, T158, R168, R255, R270, R294 and R306) located on the third and fourth exons.

MeCP2 is a protein that binds methylated CpG dinucleotides to exert transcriptional silencing of DNA in the CNS. The key effect of a reduction or absence of MeCP2 appears to be an impairment of dendritic spine development and the formation of synapses. MeCP2 expression appears to temporally correlate with brain maturation, explaining why symptoms typically appear around 18 months of age.

Presenting Features Common to ASDs

Taking the ASDs together, it is clear that there are commonalities in presenting symptoms among all 5 forms. These common features are impairments in normal social competences, and repetitive behaviours. In all but Asperger syndrome there is also a consistent presentation of delayed intellectual development most commonly manifest as a shortfall in language skills. Cognitive loss relative to normal parameters for the age is often quite marked in autism, Rett Syndrome, CDD and PDD-NOS. The presence of epilepsy or abnormal activity in the EEG is also common to autism, Fragile X Syndrome and Rett Syndrome. Epilepsy arises in situations of abnormal neuronal connectivity, Impaired neuronal connectivity and deranged synaptic function is a common feature of autism, Fragile X Syndrome and Rett Syndrome and of animal models of these conditions.

Genetic Models of ASD

To offer validity, animal models of ASDs must demonstrate similar symptoms to the clinical conditions and have a reasonable degree of face validity regarding the etiology of those symptoms. It is known that classical autism may be caused by many different genetic impairments and no single genetic defect is thought to account for more than a few percent of autism cases. Indeed, recent studies have revealed numerous de novo structural variations of chromosome locations thought to underlie ASD, in addition to rare inherited genetic defects (Marshall et al, 2008; Sebat et al, 2007). Thus, copy number variation (CNV), translocation and inversion of gene sequences at 20 key sites or more, including 1p, 5q, 7q, 15q, 16p, 17p and Xq, have been mapped as ASD loci.

However, despite the polygenetic background underlying ASD, and the complexity of the etiology, it is known that certain genetic defects can produce ASD. Some of the best characterized defects arise from chromosomal aberrations of genes that code for a cluster of postsynaptic density proteins, including neuroligin-3 (NLGN3), neuroligin-4 (NLGN4), neurexin-1α (NRXN1) and shank3 (Sebat et al, 2007). Importantly, these defects point to altered synaptic function and therefore disturbed neuronal connectivity as a final common pathway in autism and related disorders (Minshew and Williams 2007 *Arch Neurol.* 64:945-950; Gilman et al., 2011 *Neuron.* 70:898-907). Such connectivity deficits are reflected in morphological findings in post mortem examination, which reveal increased dendritic spine density in autism (Hutsler and Zhang 2010 *Brain Res.* 1309:83-94).

NLGN3 and NLGN4 are postsynaptic cell-adhesion molecules present in glutamatergic synapses. They play a role in coordinating presynaptic contact to the postsynaptic site and also interact with the postsynaptic scaffolding protein shank3. Mutations to NLGN3 and NLGN4 have been observed in the ASD population and account for perhaps 1% of all ASD cases (Lintas & Persico, 2008). Jamain and colleagues first reported a missense to NLGN3 and a frameshift to NLGN4 in two unrelated subjects, resulting in Asperger syndrome and classical autism respectively (Jamain et al, 2003). While the incidence of NLGN3 or NLGN4 mutations in the ASD population is low (indeed, no much mutations were observed in a study of 96 ASD patients in a Canadian study; Gauthier et al, 2005), it has been confirmed in preclinical studies that neuroligin mutations can indeed produce of model of autistic symptoms. Thus, introduction to mice of the same R451C missense to NLGN3 that has been reported clinically results in a mutant mouse strain showing reduced social interaction and enhanced inhibitory synaptic transmission (Tabuchi et al, 2007).

The R451C mutant therefore mouse represents a model for ASD based upon NLGN3 mutation. In this case, mutation at the R451 position of NLGN3 results in a 'gain-of-function' mutation.

In contrast, modeling the clinical mutation of NLGN4 in mice is achieved by a 'loss-of-function' mutation of NLGN4 (a classical knockout model). In this model, mutant mice display a social interaction deficit and reduced ultrasonic vocalization (Jamain et al, 2008). Communication deficits are central to clinical ASDs and in the NLGN4 knockout mice a reduction in ultrasonic vocalizations from male mice exposed to wild-type female counterparts supports the face validity of the strain as a model of ASD.

Presynaptic neurexin proteins induce postsynaptic differentiation in opposing dendrites through interactions with postsynaptic neuroligin counterparts. Mutations of the neurexin-1α (NRXN1) gene have been reported in numerous studies (Sebat et al, 2007; Marshall et al, 2008; Kim et al, 2008; Yan et al, 2008) and these have been observed in the form of copy-number variants. As with NLGN mutations, when a mutation of the NRXN1 gene is introduced to mice (in the form of gene knockout), a mutant strain with certain ASD-like features is produced (Etherton et al, 2009). These NRXN1 knockout mice show a decrease in hippocampal miniature excitatory postsynaptic current (mEPSC) frequency and a decreased input-output relationship of evoked currents. These electrophysiological effects relate to decreased excitatory transmission in the hippocampus. In addition to decreased excitatory neurotransmission, NRXN1 knockout mice exhibit a decrease in pre-pulse inhibition, though social behaviour appears, to be unaffected (Etherton et al, 2009).

Sharing certain features with the neurexin-NLGN transsynaptic construct, cell adhesion molecule 1 (CADM1) is an immunoglobulin family protein present both pre- and postsynaptically that is also involved in synaptic trans-cell adhesion activity (Biederer et al, 2002). Mutations to the CADM1 gene have been detected in ASD patients and appear to represent a further possible cause of these conditions (Zhiling et al, 2008).

Analysis of CADM1 knockout mice reveals that these animals show increased anxiety-related behavior, impaired social interaction and impaired social memory and recognition. In addition CADM1 knockout mice demonstrate poorer motor skills (Takayanagi et al, 2010). These dysfunctions are again consistent with ASD symptomatology.

22q13 deletion syndrome (also known as Phelan-McDermid Syndrome), is a rare genetic disorder caused by a microdeletion at the q13.3 terminal end of chromosome 22. This microdeletion is rarely uncovered by typical genetic screening and a fluorescence in situ hybridization test is recommended to confirm the diagnosis. Recent work indicates the syndrome is caused by errors in the gene shank3, a postsynaptic density protein critical for normal neuronal functioning. Interestingly, errors in this gene have also been associated with ASD and 22q13 deletion syndrome can commonly lead to an ASD diagnosis (Durand et al, 2007; Moessner et al, 2007; Sykes et al, 2009). Given the close association of 22q13 deletion syndrome and the consequential diagnosis of ASD, a mutant mouse model of this mutation has been developed.

The shank3 knockout mouse exhibits several deficits that mirror ASD symptoms, including reduced ultrasonic vocalizations (i.e. diminished social communication) as well as impaired social interaction time between mice. In addition, these mice have impaired hippocampal CA1 excitatory transmission, measured by input-output relationship of evoked currents and impaired long-term potentiation (LTP). LTP is believed to be a physiological process underlying memory formation and consolidation. Thus, the model exhibits a similar phenotype to the NLGN4 knockout, consistent with ASD.

As has been noted, 22q13 deletion syndrome itself is very rare. However, it provides important information that involvement specific genes may have in the etiology of ASDs. In addition to shank3, this disorder reveals a further possible gene defect in ASD. Of the 50 or so cases of 22q1.3 deletion syndrome described, all but one have a gene deletion that extends beyond shank3 to include a further gene, known as the Islet Brain-2 gene (IB2) (Sebat et al, 2007). The IB2 protein interacts with many other proteins including MAP kinases and amyloid precursor protein, appears to influence protein trafficking in neurites, and is enriched at postsynaptic densities (Giza et al, 2010). Mice lacking the protein (IB2−/− knockout mice) exhibit impaired social interaction (reduced social sniffing and interaction time), reduced exploration and cognitive and motoric deficits (Giza et al, 2010). This behavioral phenotype was associated with reduced excitatory transmission in cerebellar cells. As with shank3 knockout, the phenotype of IB2 mutation is therefore also consistent with ASD.

In addition to the animal models of postsynaptic density protein defects described above, other monogenetic syndromes that share various features with ASDs can lead to autism offer another avenue for drug targeting of ASD. An excellent example of this is Fragile X Syndrome.

Fragile X Syndrome (FXS) is caused by the expansion of a single trinucleotide gene sequence (CGG) on the X-chromosome that results in failure to express the protein coded by the fmr1 gene. FMR1 (fragile X mental retardation 1) is a protein required for normal neural development. FXS can cause a child to have autism (Hagerman et al, 2010); in 2-6% of all children diagnosed with autism the cause is FXS gene mutation. Moreover, approximately 30% of FXS children have some degree of autism and a further 30% are diagnosed with PDD-NOS (Hagerman et al, 2010). Indeed, Fragile X Syndrome is the most common known single gene cause of autism. FMR1 knockout mice have been developed as a model of FXS and, therefore, as a further model of ASD. Knockout mutation of the FMR1 gene has been shown to result in neuronal connectivity deficits such as abnormal dendritic spine development and pruning (Comery et al, 1997), along with an associated dysregulation of dendritic scaffold proteins (including shank1) and glutamate receptor subunits in postsynaptic densities (Schütt et al, 2009). These effects on dendrite morphology results deficits in functional measures of connectivity such as impaired LTP in the cortex and amygdala (Zhao et al, 2005) and hippocampus (Lauterborn et al, 2007), as well as impaired cognition (Kreuger et al, 2011) and an enhancement in social anxiety (Spencer et al, 2005). These connectivity deficits are mirrored in FXS patients, who show enhanced dendritic spine density in post mortem analyses (Irwin et al., 2000 *Cereb Cortex* 10:1034-1048). This enhanced dendritic spine density is accompanied by immature synapses (Klemmer et al., 2011 *J Biol Chem.* 286:25495-25504), i.e. may represent a functionally immature state.

In contrast to the ASDs of autism, Asperger, CDD and PDD-NOS, Rett syndrome appears to have an almost monogenetic basis and may be modeled in mice with good face validity. Rett syndrome is thought be caused, in up to 96% of cases, by a defect in the Mecp2 gene (Zoghbi, 2005). As a result, MeCP2 knockout mutant mice provide an animal model with all the hallmarks of clinical Rett syndrome, with a phenotype showing some overlap with the NLGN4, shank3 and IB2 knockout models of ASD. Thus, MeCP2 knockout mice display a clear impairment in LTP in the hippocampus along with a corresponding decrease in social and spatial memory (Moretti et al, 2006) and impaired object recognition (Schaevitz et al, 2010). This impairment in LTP is accompanied by a decrease in dendritic spine density. Patients with Rett Syndrome show reduced dendritic spine density (Belichenko et al., 1994 *Neuroreport* 5:1509-1513).

Thus, ASDs in human beings share many features of cognitive or developmental disorders in animals, including rodents. Therefore, studies of therapies of ASDs in rodents such as mice and rats are reasonably predictive of results obtained in human beings. A common feature seen in autism, Fragile X Syndrome and Rett Syndrome is the presence of neuronal connectivity deficits, reflected in either decreased dendritic spine density or enhanced dendritic spine density with immature synapses. The functional consequences of these morphological changes are similar in animal models of these disorders, reflected as deficits in LTP, for example.

Treatment of Clinical ASD and ASD Animal Models with G-2-MePE

As described above, a conserved pathology is observed in ASDs that comprises impaired neurite development, impaired synaptic connectivity and a corresponding impairment in social and cognitive functioning as a result. Such synaptic dysfunctions result from genetically altered functions of postsynaptic density proteins. Normal neurite growth and postsynaptic development may be regulated and augmented by growth factors such as brain derived neurotrophic factor (BDNF; Chapleau et al, 2009) and insulin-like growth factor-1 (IGF-1; Riikonen et al, 2006; Tropea et al, 2009). Indeed, IGF-1 is essential for normal dendritic spine growth and synapse formation (Cheng et al., 2003 *J Neurosci Res.* 73:1-9), Drugs that promote growth factor function are therefore of use in the treatment of progressive developmental disorders such as ASDs. G-2-MePE is a small molecule methylated analog of the terminal tripeptide of IGF-1, IGF1 (1-3). As an IGF-1 mimetic analog, G-2-MePE exerts trophic and neuroprotective effects in various animal models. G-2-MePE is therefore effective at treating ASD symptoms such as those relating to synaptic dysfunctions resulting from the gene mutations described above.

In clinical terms, ASD patients, presenting with autism, Asperger syndrome, Rett syndrome, childhood disintegrative disorder and PDD-NOS, as well as patients with 22q13 deletion syndrome, Fragile X Syndrome and pathological demand avoidance are treated with G-2-MePE. Patients exhibit social and communication impairments as well as cognitive deficit. Treatment with G-2-MePE, for example, on a daily basis and in another example, by the oral route, is observed to induce an improvement in stereotypic repetitive movements, improved social functioning and improved cognitive performance following drug treatment.

In animal models of ASDs, daily G-2-MePE treatment by oral gavage or intraperitoneal injection to knockout mice will improve ASD-like symptoms. G-2-MePE is effective in the following ASD mutant mouse models: NLGN3 (R451C) mutant, NLGN4 knockout, NRXN1 knockout, CADM1 knockout, shank3 knockout, IB2 knockout, FMR1 knockout and MeCP2 knockout. When administered sub-chronically (1-10 weeks) on a daily basis, G-2-MePE is effective at improving LTP in the hippocampus following burst stimulation or high frequency stimulation. Similarly, G-2-MePE increases excitatory neurotransmission as measured by field extracellular postsynaptic potential electrophysiological recordings in cortex, hippocampus and cerebellum. As a result of improved excitatory neurotransmission (reversal of observed ASD-like neurotransmission deficit), G-2-MePE is observed to improve cognitive and motoric outcome tests of cognitive performance. Thus, G-2-MePE improves performance in the Morris water maze and radial arm maze tests. In models of social interaction, G-2-MePE, administered to ASD mutant mice, increases time spent by knockout males in social interaction with wild-type females. In addition, ultrasonic vocalizations to female wild type mice is increased. In models in which longevity is observed to be reduced in mutant mice compared to wild-type controls (such as the MeCP2 knockout mouse model of Rett Syndrome), treatment with G-2-MePE increases the lifespan of the animals.

G-2-MePE has been found to inhibit non-convulsive seizures (NCS) in animals with hypoxic-ischemic injuries caused by middle cerebral artery occlusion (MCaO; U.S. Pat. No. 7,714,020; Lu et al., *NNZ-2566, a glypromate analog, attenuates brain ischemia-induced nonconvulsive seizures in rats*, J Cerebral Blood Flow metabolism (2009) 1-9) and inhibits neuroinflammation in animals with penetrating ballistic injury (pTBI; Wei et al., *NNZ-2566 treatment inhibits neuroinflammation and pro-inflammatory cytokine expression induced by experimental penetrating ballistic-like brain injury in rats*, J. Neuroinflammation (2009) 6:19, 1-10).

Our findings that G-2-MePE also are effective in treating Rett Syndrome and ASDs, are completely unexpected based on the prior art. This is because the NCS in the MCaO model is caused by hypoxia-ischemia and the inflammatory cytokine expression in the pTBI model is caused by penetrating trauma, both of which are acute insults that are very different from the chronic effects of MECP2 or other mutations on synaptic maturation.

Because G-2-MePE is a member of the compounds of GPE analogs disclosed herein, any of the disclosed compounds also can be effective in treating symptoms of ASDs. Further, because compounds and methods of this invention address underlying neurological mechanisms (e.g., decrease neural inflammation by inhibiting release of inflammatory cytokines), this invention can provide more than short-term management of symptoms. Rather, compounds and methods of this invention can improve neural function, promote neuronal cell migration, promote neurogenesis, promote neuronal stem cell differentiation, promote axonal and dendritic outgrowth, and promote synaptic transmission, thereby relieving adverse symptoms of ASDs.

Compounds of the Invention

While the broadest definition of the invention is set out in the Summary, certain compounds of this invention are presently described.

In one aspect, this invention provides compounds of Formula 1 and Formula 2:

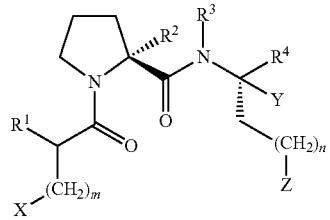

Formula 1

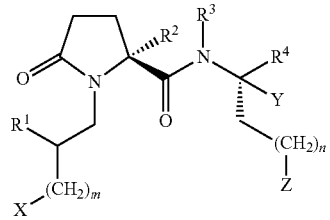

Formula 2 where m is 0 or 1;
n is 0 or 1;
X is H or $-NR^6R^7$;
Y is H, alkyl, $-CO_2R^5$, or $-CONR^6R^7$;
Z is H, alkyl, $-CO_2R^5$ or $-CONR^6R^7$;
$R^1$ is H, alkyl, or aralkyl;
$R^2$, $R^3$, and $R^4$ are independently H or alkyl;
each $R^5$ is independently H, alkyl, or a fatty alcohol residue;
each $R^6$ and $R^7$ is independently H, alkyl, or aralkyl, or $-NR^6R^7$ is pyrrolidino, piperidino, or morpholino;
or a lactone formed when a compound where Y is $-CO_2$(alkyl) and Z is $-CO_2H$ or where Y is $-CO_2H$ and Z is $-CO_2$(alkyl) is lactonized;
and the pharmaceutically acceptable salts thereof,
provided that the compound is not GPE, N-Me-GPE, GPE amide, APE, GPQ or a salt thereof.

In some aspects, this invention includes:
(a) the compounds are compounds of Formula 1;
(b) m is 0;
(c) n is 1;
(d) at least one of X, Y, $R^1$, $R^2$, $R^3$, $R^4$, and $R^5$ is not hydrogen;
(e) X is $-NR^6R^7$; and
(f) Y is $-CO_2R^5$ or $-CO_2NR^6R^7$ and
(g) Z is $-CO_2R$ or $-CO_2NR^6R^7$.

Other compounds of the invention are compounds of Formula 1 wherein X is $-NR^6R^7$ and $R^6$ and $R^7$ are independently alkyl or aralkyl. The more preferred embodiment is a compound of Formula 1 wherein X is $-NR^6R^7$ and both $R^6$ and $R^7$ are alkyl.

Yet another compound of the invention is G-2-MePE, a compound of Formula 1 wherein m is 0, n is 1, R1=R3=R4=H, R2 is methyl, X is $NR^6R^7$ where $R^6=R^7=H$, Y is $CO_2R^5$ where $R^5=H$, Z is $CO_2R^5$ where $R^5=H$.

Pharmacology and Utility

Compounds of this invention can have anti-inflammatory, anti-apoptotic, anti-necrotic and neuroprotective effects. Their activity in vivo can be measured by cell counts, specific staining of desired markers, or by methods such as those discussed in Klempt N D et al: Hypoxia-ischemia induces transforming growth factor β1 mRNA in the infant rat brain. Molecular Brain, Research: 13: 93-101. Their activity can also be measured in vitro using methods known in the art or described herein.

Conditions affecting brain function become prevalent in aging populations. Memory loss and memory impairment are distressing to patients affected and their families. Memory loss or impairment can result from normal aging, injury to the brain, neurodegenerative disease and psychological or psychiatric dysfunctions. It is therefore of great benefit to patients, their families and to society that novel compounds are identified and characterized that enhance memory and/or cognitive function, and treat or prevent memory loss or impairment.

It is desirable to study effects of potential therapeutic agents in animal systems. One such useful system is the rat. It is known that with aging, rats and other animals (including human beings) can exhibit symptoms of memory loss, memory impairment and other cognitive dysfunctions. Further, it is known that studies in rats of therapeutic agents are predictive of therapeutic effects in humans. Thus, studies of effects of GPE and G-2-MePE and cognitive function in aging rats are reasonably predictive of therapeutic effects of those agents in aging human beings that have or are prone to acquiring memory deficits or other cognitive dysfunction. Compounds of this invention can enhance cognitive function and/or treat memory disorders. The cognitive enhancing activity and therapeutic activity in vivo can be measured by standard neuropsychological or behavioral tests known to individuals skilled in the art. Such tests can be chosen from a wide range of available tests described above, and will vary depending on the cognitive function to be tested and the condition of the animal.

Standard behavioral tests useful for testing cognitive function in experimental animals include but are not limited to the Morris Water Maze test, passive avoidance response test, novel object recognition test, olfactory discrimination test, the 8-arm radial maze test and the T-maze test. These tests are directly applicable to studies of effects of GPE and G-2-MePE on cognitive function in aging rats.

The compounds of this invention are also expected to have pharmacological and therapeutic activities similar to those of GPE, and these activities may be measured by the methods known in the art, and discussed in the documents cited herein, and by methods used for measuring the activity of GPE.

The therapeutic ratio of a compound can be determined, for example, by comparing the dose that gives effective anti-inflammatory, anti-apoptotic and anti-necrotic activity in a suitable in vivo model such as a hypoxic-ischemic injury (Sirimanne E S, Guan J, Williams C E and Gluckman P D: Two models for determining the mechanisms of damage and repair after hypoxic-ischemic injury in the developing rat brain (Journal of Neuroscience Methods: 55: 7-14, 1994) in a suitable animal species such as the rat, with the dose that gives significant observable side-effects in the test animal species.

The therapeutic ratio of a compound can also be determined, for example by comparing the dose that gives effective cognitive function enhancement or treats a memory disorder in a suitable in vivo model (Examples 4, 5 and 6 below) in a suitable animal species such as the rat, with the dose that gives significant weight loss (or other observable side-effects) in the test animal species.

Compounds of this invention can be useful in treatment of a variety of neurodegenerative disorders, including hypoxia/ischemia and neuronal degeneration (U.S. Pat. No. 7,041,314), traumatic brain injury, motor disorders and seizures, stroke, and cardiac artery bypass graft surgery (U.S. Pat. No. 7,605,177), non-convulsive seizures (U.S. Pat. No. 7,714,020), and disorders of cognitive function (U.S. application Ser. No. 12/903,844). Additionally, as described more fully herein below, compounds of this invention can be useful for treating Rett Syndrome, including prolonging life, increasing neuronal activity and treating seizures associated with Rett Syndrome.

In one study of Rett Syndrome in mice (using the MeCP2 knock-out model), GPE was found to have effects to prolong life and increase neuronal function (U.S. Publication No. 2009/0099077). However, as disclosed further herein, GPE, being a naturally occurring peptide, is rapidly degraded in vivo and in vitro, and its utility in chronic therapy of patients with Rett Syndrome is therefore unclear.

Pharmaceutical Compositions and Administration

In general, compounds of this invention can be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease or injury, the severity of the disease, the age and relative health of the animal being treated, the potency of the compound(s), and other factors. As anti-inflammatory, anti-apoptotic, anti-necrotic, anti-neurodegenerative, therapeutically effective amounts of compounds of this invention can range from about 0.001 milligrams per kilogram (mg/kg) to about 100 (mg/kg) mass of the animal, for example, about 0.1 to about 10 mg/kg, with lower doses such as about 0.001 to about 0.1 mg/Kg, e.g. about 0.01 mg/Kg, being appropriate for administration through the cerebrospinal fluid, such as by intracerebroventricular administration, and higher doses such as about 1 to about 100 mg/Kg, e.g. about 10 mg/Kg, being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

In general, compounds of this invention can be administered as pharmaceutical compositions by one of the following routes: oral, topical, systemic (e.g. transdermal, intranasal, or by suppository), or parenteral (e.g. intramuscular, subcutaneous, or intravenous injection), by administration to the CNS (e.g. by intraspinal or intercisternal injection); by implantation, and by infusion through such devices as osmotic pumps, implantable pumps, transdermal patches, and the like. Compositions can take the form of tablets, pills, capsules, semi-solids, powders, sustained release formulation, solutions, suspensions, elixirs, aerosols, soluble gels or any other appropriate compositions; and comprise at least one compound of this invention in combination with at least one pharmaceutically acceptable or physiological acceptable excipient. Suitable excipients are well known to persons of ordinary skill in the art, and they, and the methods of formulating the compositions, may be found in such standard references as Gennaro AR: Remington: The Science and Practice of Pharmacy, 20$^{th}$ ed., Lippincott, Williams & Wilkins, 2000. Suitable liquid carriers, especially for injectable solutions, include water, aqueous saline solution, aqueous dextrose solution, glycols, and the like, with isotonic solutions being preferred for intravenous, intraspinal, and intracisternal administration and vehicles such as artificial cerebrospinal fluid being also especially suitable for administration of the compound to the CNS. The above text is expressly incorporated herein fully by reference.

Compounds of this invention can be administered orally, in tablets or capsules. In some embodiments, compounds of this invention can be prepared in water-in-oil emulsions in the form of microemulsions, coarse emulsions, liquid crystals, or nanocapsules (U.S. application Ser. No. 12/283,684, now U.S. Pat. No. 7,887,839 issued Feb. 15, 2011). Because compounds of this invention can have substantial oral bioavailability, they can be advantageously used for convenient and chronic administration. Additionally, orally available compositions include soluble hydrogels containing active compounds, thus permitting oral administration of neuroprotective compounds without the need for a patient to swallow a tablet or capsule. Such slow-release materials and gels are known in the art.

Compounds of this invention can be administered after or before onset of a condition that is likely to result in neurodegeneration or a symptom thereof. For example, it is known that hypoxia/ischemia can occur during coronary artery bypass graft (CABG) surgery. Thus, a patient can be pretreated with a compound of this invention before being placed on an extracorporeal oxygenation system. In some embodiments, it can be desirable to administer a compound of this invention beginning about 4 hours before surgery or before an event that is likely to lead to traumatic or other neurological injury. In other embodiments, it can be desirable to infuse a compound of this invention during the surgery or during a surgical procedure to repair a neurological injury. Compounds of this invention can also be used in emergency situations, for example in a patient that has just experienced a stroke, hypoxic event, traumatic brain injury or other acute insult. In such situations, a compound of this invention can be administered immediately after a diagnosis of neural injury is made.

In some situations, kits containing compound of this invention can be prepared in advance of use in the field. A kit can contain a vial containing a compound of the invention in a pharmaceutically acceptable formulation (e.g., for injection or oral administration), along with a syringe or other delivery device, and instructions for use. In situations in which a seizure is diagnosed, a compound of this invention can be administered along with an anticonvulsant, Many anticonvulsants are known in the art and need not be described in detail herein.

Additionally, "secondary" neurological injuries can occur after a primary insult such as a traumatic injury, stroke or surgical procedure. For example, after a stroke, penetrating brain injury or a CABG procedure, inflammation of neural tissue can lead to neurodegeneration. Secondary injuries can be reflected by increased activation of inflammatory cells (e.g., astrocytes and/or microglia), and actions of inflammatory mediators can cause neurological damage. Thus, in some embodiments, it can be desirable to administer a compound of this invention for periods beginning before the insult, to up to about 100 hours after the insult. In other embodiments, it can be desirable to administer a compound of this invention beginning before the insult, during the insult and after the insult, either continuously, as an infusion, or in discrete doses separated by a desired time interval.

Compounds of this invention can also be suitably administered by a sustained-release system or gel material with G-2-MePE incorporated therein. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al., 1981), ethylene vinyl acetate (Langer et al., supra), or poly-D-(−)-3-hydroxybutyric acid (EP 133,988). Additionally, gel compositions based on polysaccharides (e.g., carboxymethyl cellulose, carboxyethyl cellulose, chitosan or other cellulose derivatives) and polyethylene oxide derivatives (e.g., polyethylene glycols) can be used used. These gel compositions are soluble in aqueous solutions, are biocompatible, non-toxic and therefore can be used for administering compounds of this invention to any mucosal surface, including the oral cavity, nasopharynx, urogenital tract, intestine or rectum.

Sustained-release compositions also include a liposomally entrapped compound. Liposomes containing the compound are prepared by methods known per se; DE 3,218,121; Epstein et al., 1985; Hwang et al., 1980; EP 52,322; EP 36,676; EP 88,046; EP 143,949; EP 142,641; Japanese Pat. Appln. 83-118008; U.S. Pat. Nos. 4,485,045 and 4,544,545; and EP 102, 324. Ordinarily, liposomes are of the small (from or about 200 to 800 Angstroms) unilamellar type in which the lipid content is greater than about 30 mole percent cholesterol, the selected proportion being adjusted for the most efficacious therapy. Each and every of the above-identified publications is expressly herein incorporated fully by reference, as if each had been separately so incorporated.

Compounds of this invention can also be attached to polyethylene glycol ("PEGylated") to increase their lifetime in vivo, based on, e.g., the conjugate technology described in WO 95/32003.

Desirably, if possible, when administered as an anti-inflammatory, an anti-apoptotic agent, an anti-necrotic agent, or an anti-neurodegenerative agent, compounds of this invention can be administered orally. The amount of a compound of this invention in the composition can vary widely depending on the type of composition, size of a unit dosage, kind of excipients, and other factors well known to those of ordinary skill in the art. In general, the final composition can comprise from about 0.0001 percent by weight (% w) to about 10% w of the compound of this invention, preferably about 0.001% w to about 1% w, with the remainder being an excipient or excipients.

A composition may optionally contain, in addition to a compound of this invention, at least one agent selected from, for example, growth factors and associated derivatives (insulin-like growth factor-1 (IGF-1), insulin-like growth factor-II (IGF-II), transforming growth factor-β1, activin, growth hormone, nerve growth factor, brain-derived neurotrophic factor (BDNF), growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHP-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), α-, β-, γ-, or consensus interferon, and TNF-α. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analog [ORG 2766] and dizolcipine (MK-801), selegiline; glutamate antagonists such as mematine (Namenda) NPS1506, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAdCAM-1 and/or its integrin α4 receptors (α4β1 and α4β7), such as anti-MAdCAM-1mAb MECA-367 (ATCC accession no. HB-9478). Combination therapy with metabotropic glutamate receptor antagonists such as fenobam may also be useful. Also, in addition to a compound of this invention, a composition may include a selective serotonin reuptake inhibitor such as fluoxetine, a selective norepinephine reuptake inhibitor such as viloxazine, or an atypical anti-psychotic such as risperidone. Most of these agents, especially the peptides such as the growth factors, etc., are not orally active, and will require administration by injection or infusion.

Preparation of Compositions

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art. For example, N-pyrrolidineacetic acid is described in Dega-Szafran Z and Pryzbylak R. Synthesis, IR, and NMR studies of zwitterionic α-(1-pyrrolidine)alkanocarboxylic acids and their N-methyl derivatives. J. Mol. Struct.: 436-7, 107-121, 1997; and N-piperidineacetic acid is described in Matsuda O, Ito S, and Sekiya M. Reaction of N-(alkoxymethyl)dialkylamines and N,N'-methylenebisdialkylamines with isocyanides. Chem. Pharm. Bull.: 23(1), 219-221, 1975. Each of the above-identified publications is herein expressly incorporated fully by reference as though individually so incorporated.

Starting materials, intermediates, and compounds of this invention may be isolated and purified using conventional techniques, including filtration, distillation, crystallization, chromatography, and the like. They may be characterized using conventional methods, including physical constants and spectral data.

Compounds of this invention may be prepared by the methods described below and as given in the Examples.

Compounds of Formula 1 are analogs of GPE, or modifications thereof, such as esters or amides. In general, they may be prepared by methods such as are already well-known to persons of ordinary skill in the art of peptide and modified peptide synthesis, following the reaction schemes set forth in the FIGS. 1-11 accompanying this specification, or by following other methods well-known to those of ordinary skill in the art of the synthesis of peptides and analogs.

Conveniently, synthetic production of the polypeptides of the invention may be according to the solid-phase synthetic method described by Merrifield et al. Solid phase peptide synthesis. I. The synthesis of a tetrapeptide: J. Amer. Chem. Soc.; 85, 2149-2156, 1963. This technique is well understood and is a common method for preparation of peptides. The general concept of this method depends on attachment of the first amino acid of the chain to a solid polymer by a covalent bond. Succeeding protected amino acids are added, one at a time (stepwise strategy), or in blocks (segment strategy), until the desired sequence is assembled. Finally, the protected peptide is removed from the solid resin support and the protecting groups are cleaved off. By this procedure, reagents and by-products are removed by filtration, thus eliminating the necessity of purifying intermediaries.

Amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl ($BzlCl_2$), and phenylmethoxycarbonyl (Z or CBZ). Additional protective groups are identified in Merrifield, cited above, as well as in McOmie J F W: Protective Groups in Organic Chemistry, Plenum Press, New York, 1973, both references expressly incorporated fully herein.

General procedures for preparing peptides of this invention involve initially attaching a carboxyl-terminal protected amino acid to the resin. After attachment the resin is filtered, washed and the protecting group (desirably BOC) on the 1-amino group of the carboxyl-terminal amino acid is removed. The removal of this protecting group must take place, of course, without breaking the bond between that amino acid and the resin. The next amino, and if necessary, side chain protected amino acid, is then coupled to the free l-amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Alternative techniques for peptide synthesis are described in Bodanszky et al, Peptide Synthesis, 2nd ed, John Wiley and Sons, New York, 1976. For example, the peptides of the invention may also be synthesized using standard solution peptide synthesis methodologies, involving either stepwise or block coupling of amino acids or peptide fragments using chemical or enzymatic methods of amide bond formation. (See, e.g., H. D. Jakubke in The Peptides, Analysis, Synthesis, Biology, Academic Press, New York, 1987, p. 103-165; J. D. Glass, ibid., pp. 167-184; and European Patent 0324659 A2, describing enzymatic peptide synthesis methods.) These solution synthesis methods are well known in the art. Each of the above-identified publications is expressly incorporated herein fully by reference as though individually so incorporated.

Commercial peptide synthesizers, such as the Applied Biosystems Model 430A, are available for the practice of these methods.

A person of ordinary skill in the art will not have to undertake undue experimentation, taking account of that skill and the knowledge available, and of this disclosure, in developing one or more suitable synthetic methods for compounds of this invention.

For example, analogs in which the glycine residue of GPE is replaced by an alternative amino acid, or by a non-amino acid, may conveniently be prepared by the preparation of a C-protected proline-glutamic acid dipeptide (such as the dibenzyl ester), and coupling that dipeptide with an N-protected glycine analog, such as BOC-N-methylglycine, BOC- L-valine, N-pyrrolidineacetic acid, and the like, followed by deprotection, as illustrated in FIGS. 2 and 3. Analogs in which the glutamic acid residue of GPE is replaced by an alternative amino acid or an amino acid amide or ester may conveniently be prepared by the preparation of an N-protected glycine-L-proline dipeptide (such as BOC-glycyl-L-proline), and coupling that dipeptide with a C-protected glutamic acid or analog thereof, such as tert-butyl γ-aminobutyrate, methyl 4-amino-4-dimethylcarbamoylbutyrate, L-glutamine methyl ester, dimethyl I-methylglutamate, etc. Lactones may be prepared by the preparation of an appropriate mono-acid-mono-ester derivative and reduction Analogs in which $R^2$ is alkyl may conveniently be prepared simply by use of the appropriate 2-alkylproline in the synthesis, and similarly analogs in which $R^3$ is alkyl may conveniently be prepared by the use of the appropriate N-alkylglutamic acid or analog in the synthesis. Where modifications are to be made to two or more amino acids, the coupling techniques will still be the same, with just more than one modified amino acid or analog being used in the synthesis. The choice of appropriate protecting groups for the method chosen (solid-phase or solution-phase), and of appropriate substrates if solid-phase synthesis is used, will be within the skill of a person of ordinary skill in the art.

Compounds of Formula 2 may be prepared from suitably protected 5-oxo-L-proline or analogs or derivatives thereof, following methods such as the coupling of the proline carboxyl group with a protected glutamic acid or analog or derivative to give an analog of intermediate A of FIG. 2, comparable to the coupling reaction shown in FIG. 2, and then alkylating the pyrrolidine nitrogen with a group of the formula A-$(CH_2)_m$—$CH(R^1)$—$CH_2R$, protected at A if necessary, where R is a leaving group under alkylation conditions. Alternatively, the suitably protected 5-oxo-L-proline may first by alkylated at the pyrrolidine nitrogen to give an analog of intermediate B of FIG. 4, and then coupling this with a suitably protected glutamic acid or analog or derivative in the manner shown in FIGS. 4 though 9.

EXAMPLES

The following examples are intended to illustrate embodiments of this invention, and are not intended to limit the scope to these specific examples. Persons of ordinary skill in the art can apply the disclosures and teachings presented herein to develop other embodiments without undue experimentation and with a likelihood of success. All such embodiments are considered part of this invention.

Example 1

Synthesis of
N,N-Dimethylglycyl-L-prolyl)-L-glutamic acid

The following non-limiting example illustrates the synthesis of a compound of the invention, N,N-Dimethylglycyl-L-prolyl-L-glutamic acid

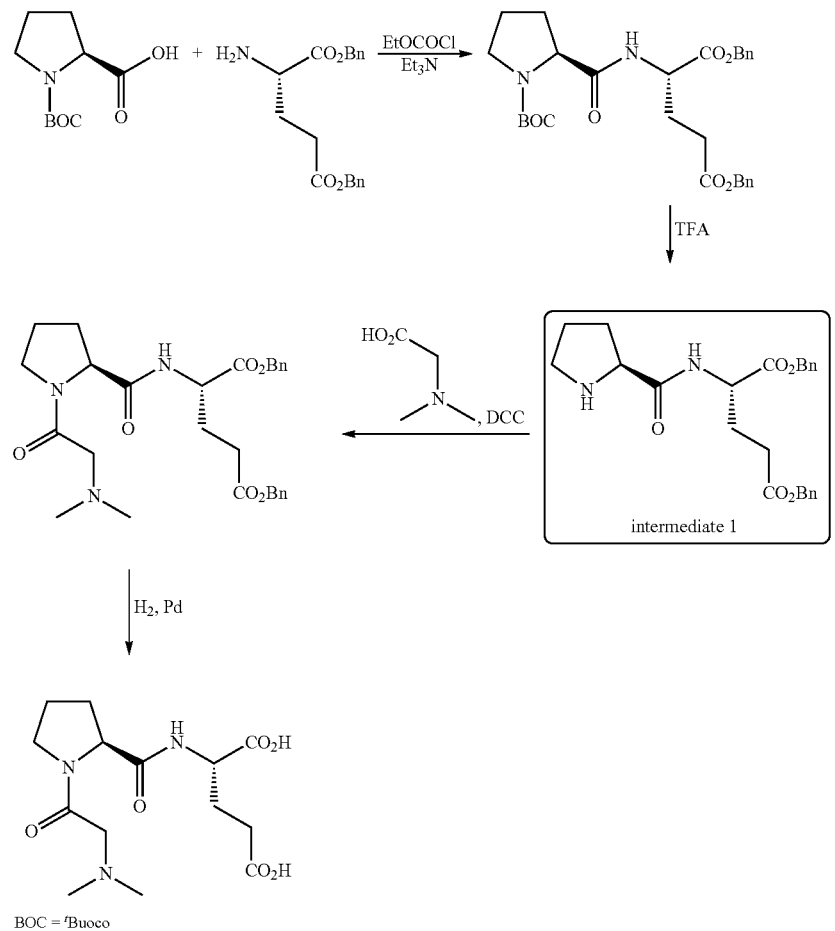

All starting materials and other reagents were purchased from Aldrich; BOC=tert-butoxycarbonyl; Bn=benzyl.

BOC-L-proline-(β-benzyl)-L-glutamic acid benzyl ester

To a solution of BOC-proline [Anderson G W and McGregor A C: J. Amer. Chem. Soc.: 79, 6810, 1994] (10 mmol) in dichloromethane (50 ml), cooled to 0° C., was added triethylamine (1.39 ml, 10 mmol) and ethyl chloroformate (0.96 ml, 10 mmol). The resultant mixture was stirred at 0° C. for 30 minutes. A solution of dibenzyl-L-glutamate (10 mmol) was then added and the mixture stirred at 0° C. for 2 hours then warmed to room temperature and stirred overnight. The reaction mixture was washed with aqueous sodium bicarbonate and citric acid (2 mol l$^{-1}$) then dried (MgSO$_4$) and concentrated at reduced pressure to give BOC-L-proline-L-glutamic acid dibenzyl ester (5.0 g, 95%).

L-proline-L-glutamic acid dibenzyl ester

A solution of BOC-L-glutamyl-L-proline dibenzyl ester (3.4 g, 10 mmol), cooled to 0° C., was treated with trifluoroacetic acid (25 ml) for 2 h. at room temperature. After removal of the volatiles at reduced pressure the residue was triturated with ether to give L-proline-L-glutamic acid dibenzyl ester.

N,N-Dimethylglycyl-L-prolyl-L-glutamic acid

A solution of dicyclohexylcarbodiimide (10.3 mmol) in dichloromethane (10 ml) was added to a stirred and cooled (0° C.) solution of L-proline-L-glutamic acid dibenzyl ester (10 mmol), N,N-dimethylglycine (10 mmol) and triethylamine (10.3 mmol) in dichloromethane (30 ml). The mixture was stirred at 0° C. overnight and then at room temperature for 3 h. After filtration, the filtrate was evaporated at reduced pressure. The resulting crude dibenzyl ester was dissolved in a mixture of ethyl acetate (30 ml) and methanol (30 ml) containing 10% palladium on charcoal (0.5 g) then hydrogenated at room temperature and pressure until the uptake of hydrogen ceased. The filtered solution was evaporated and the residue recrystallised from ethyl acetate to yield the tripeptide derivative.

It can be appreciated that following the method of the Examples, and using alternative amino acids or their amides or esters, will yield other compounds of Formula 1.

Example 2

Synthesis of Glycyl-L-2-Methyl-L-Prolyl-L-Glutamate Glycl-L-2-Methylprolyl-L-Glutamic Acid (G-2MePE)

Scheme 1 Reagents, and conditions and yields:

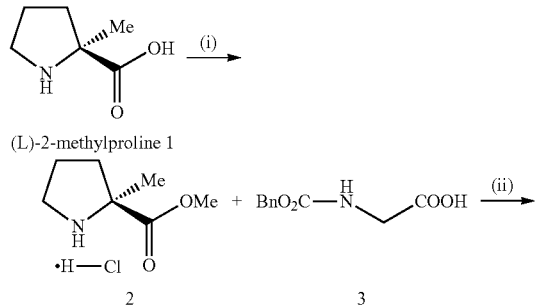

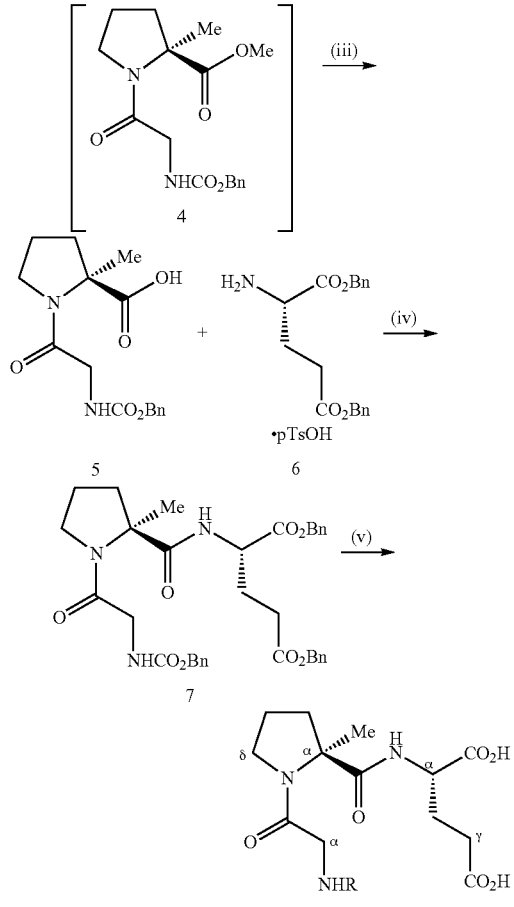

G-2MePE: R = H (73:27 trans:cis)
8: R = CH$_3$ (i) SOCl$_2$, MeOH, 79° C., N$_2$, 24 h (104%); (ii) Et$_3$N, DCC, CH$_2$Cl$_2$, 0° C. to RT, N$_2$, 20 h; (iii) 1M aq. NaOH, 1,4-dioxane, 19 h (60%, 2 steps); (iv) Et$_3$N, BoPCl, CH$_2$Cl$_2$, RT, N$_2$, 17 h (89%); (v) H$_2$, 10% Pd/C, 91:9 MeOH—H$_2$O, RT, 23 h (86%)

L-2-Methylproline and L-glutamic acid dibenzyl ester p-toluenesulphonate were purchased from Bachem, N-benzyloxycarbonyl-glycine from Acros Organics and bis(2-oxo-3-oxazolidinyl)phosphinic chloride (BoPCl, 97%) from Aldrich Chem. Co.

Methyl L-2-methylprolinate hydrochloride 2

Thionyl chloride (5.84 cm$^3$, 80.1 mmol) was cautiously added dropwise to a stirred solution of (L)-2-methylproline 1 (0.43 g, 3.33 mmol) in anhydrous methanol (30 cm$^3$) at −5° C. under an atmosphere of nitrogen. The reaction mixture was heated under reflux for 24 h, and the resultant pale yellow-coloured solution was concentrated to dryness in vacuo. The residue was dissolved in a 1:1 mixture of methanol and toluene (30 cm$^3$) then concentrated to dryness to remove residual thionyl chloride. This procedure was repeated twice more, yielding hydrochloride 2 (0.62 g, 104%) as an hygroscopic, spectroscopically pure, off-white solid: mp 127-131° C.; $[\alpha]_D$ −59.8 (c 0.24 in CH$_2$Cl$_2$); $\nu_{max}$ (film)/cm$^{-1}$ 3579, 3398 br, 2885, 2717, 2681, 2623, 2507, 1743, 1584, 1447, 1432, 1374, 1317, 1294, 1237, 1212, 1172, 1123, 981, 894, 861 and 764; $\delta_H$ (300 MHz; CDCl$_3$; Me$_4$Si) 1.88 (3H, s, Proα-CH$_3$), 1.70-2.30 (3H, br m, Proβ-H$_A$H$_B$ and Proγ-H$_2$), 2.30-2.60 (1H, br m, Proβ-H$_A$H$_B$), 3.40-3.84 (2H, br m, Proδ-H$_2$), 3.87

(3H, s, CO$_2$CH$_3$), 9.43 (1H, br s, NH) and 10.49 (1H, br s, HCl); δ$_C$ (75 MHz; CDCl$_3$) 21.1 (CH$_3$, Proα-CH$_3$), 22.4 (CH$_2$, Proγ-C), 35.6 (CH$_2$, Proβ-C), 45.2 (CH$_2$, Proδ-C), 53.7 (CH$_3$, CO$_2$CH$_3$), 68.4 (quat., Proα-C) and 170.7 (quat., CO); m/z (FAB+) 323.1745 [M$_2$.H$^{35}$Cl.H$^+$: (C$_7$H$_{13}$NO$_2$)$_2$.H$^{35}$Cl.H requires 323.1738] and 325.1718 [M$_2$.H$^{37}$Cl.H$^+$: (C$_7$H$_{13}$NO$_2$)$_2$.H$^{37}$Cl.H requires 325.1708].

N-Benzyloxycarbonyl-glycyl-L-2-methylproline 5

Anhydrous triethylamine (0.45 cm$^3$, 3.23 mmol) was added dropwise to a mixture of methyl L-2-methylprolinate hydrochloride 2 (0.42 g, 2.34 mmol) and N-benzyloxycarbonyl-glycine (98.5%) 3 (0.52 g, 2.45 mmol) in methylene chloride (16 cm$^3$), at 0° C., under an atmosphere of nitrogen. The resultant solution was stirred for 20 min and a solution of 1,3-dicyclohexylcarbodiimide (0.56 g, 2.71 mmol) in methylene chloride (8 cm$^3$) at 0° C. was added dropwise and the reaction mixture was warmed to room temperature and stirred for a further 20 h. The resultant white mixture was filtered through a Celite™ pad to partially remove 1,3-dicyclohexylurea, and the pad was washed with methylene chloride (50 cm$^3$). The filtrate was washed successively with 10% aqueous hydrochloric acid (50 cm$^3$) and saturated aqueous sodium hydrogen carbonate (50 cm$^3$), dried (MgSO$_4$), filtered, and concentrated to dryness in vacuo. Further purification of the residue by flash column chromatography (35 g SiO$_2$; 30-70% ethyl acetate-hexane; gradient elution) afforded tentatively methyl N-benzyloxycarbonyl-glycyl-L-2-methylprolinate 4 (0.56 g), containing 1,3-dicyclohexylurea, as a white semi-solid: R$_f$ 0.65 (EtOAc); m/z (EI+) 334.1534 (M$^+$.C$_{17}$H$_{22}$N$_2$O$_5$ requires 334.1529) and 224 (1,3-dicyclohexylurea).

To a solution of impure prolinate 4 (0.56 g, ca. 1.67 mmol) in 1,4-dioxane (33 cm$^3$) was added dropwise 1M aqueous sodium hydroxide (10 cm$^3$, 10 mmol) and the mixture was stirred for 19 h at room temperature. Methylene chloride (100 cm$^3$) was then added and the organic layer extracted with saturated aqueous sodium hydrogen carbonate (2×100 cm$^3$). The combined aqueous layers were carefully acidified with hydrochloric acid (32%), extracted with methylene chloride (2×100 cm$^3$), and the combined organic layers dried (MgSO$_4$), filtered, and concentrated to dryness in vacuo. Purification of the ensuing residue (0.47 g) by flash column chromatography (17 g SiO$_2$; 50% ethyl acetate-hexane to 30% methanol-dichloromethane; gradient elution) gave N-protected dipeptide 5 (0.45 g, 60%) as a white foam in two steps from hydrochloride 2. Dipeptide 5 was shown to be exclusively the trans-orientated conformer by NMR analysis: R$_f$ 0.50 (20% MeOH—CH$_2$Cl$_2$); [α]$_D$ −62.3 (c 0.20 in CH$_2$Cl$_2$); ν$_{max}$ (film)/cm$^{-1}$ 3583, 3324 br, 2980, 2942, 1722, 1649, 1529, 1454, 1432, 1373, 1337, 1251, 1219, 1179, 1053, 1027, 965, 912, 735 and 698; δ$_H$ (300 MHz; CDCl$_3$; Me$_4$Si) 1.59 (3H, s, Proα-CH$_3$), 1.89 (1H, 6 lines, J 18.8, 6.2 and 6.2, Prop-H$_A$H$_B$), 2.01 (2H, dtt, J 18.7, 6.2 and 6.2, Proγ-H$_2$), 2.25-2.40 (1H, m, Proβ-H$_A$H$_B$), 3.54 (2H, t, J 6.6, Proδ-H$_2$), 3.89 (1H, dd; J 17.1 and 3.9, Glyα-H$_A$H$_B$), 4.04 (1H, dd, J 17.2 and 5.3, Glyα-H$_A$H$_B$), 5.11 (2H, s, OCH$_2$Ph), 5.84 (1H, br t, J 4.2, N—H), 7.22-7.43 (5H, m, Ph) and 7.89 (1H, br s, —COOH); δ$_C$ (75 MHz; CDCl$_3$) 21.3 (CH$_3$, Proα-CH$_3$), 23.8 (CH$_2$, Proγ-C), 38.2 (CH$_2$, Prop-C), 43.6 (CH$_2$, Glyα-C), 47.2 (CH$_2$, Proδ-C), 66.7 (quat, Proα-C), 66.8 (CH$_2$, OCH$_2$Ph), 127.9 (CH, Ph), 128.4, (CH, Ph), 136.4 (quat., Ph), 156.4 (quat., NCO$_2$), 167.5 (quat., Gly-CON) and 176.7 (quat., CO); m/z (EI+) 320.1368 (M$^+$. C$_{16}$H$_{20}$N$_2$O$_5$ requires 320.1372).

Dibenzyl N-benzyloxycarbonyl-glycyl-L-2-methyl-prolyl-L-glutamate 7

Triethylamine (0.50 cm$^3$, 3.59 mmol) was added dropwise to a solution of dipeptide 5 (0.36 g, 1.12 mmol) and L-glutamic acid dibenzyl ester p-toluenesulphonate 6 (0.73 g, 1.46 mmol) in methylene chloride (60 cm$^3$) under nitrogen at room temperature, and the reaction mixture stirred for 10 min. Bis(2-oxo-3-oxazolidinyl)phosphinic chloride (BoPCl, 97%) (0.37 g, 1.41 mmol) was added and the colourless solution stirred for 17 h. The methylene chloride solution was washed successively with 10% aqueous hydrochloric acid (50 cm$^3$) and saturated aqueous sodium hydrogen carbonate (50 cm$^3$), dried (MgSO$_4$), filtered, and evaporated to dryness in vacuo. Purification of the resultant residue by repeated (2×) flash column chromatography (24 g SiO$_2$; 30-70% ethyl acetate-hexane; gradient elution) yielded fully protected tripeptide 7 (0.63 g, 89%) as a colourless oil, Tripeptide 7 was shown to be exclusively the trans-orientated conformer by NMR analysis: R$_f$ 0.55 (EtOAc); [α]$_D$ −41.9 (c 0.29 in CH$_2$Cl$_2$); ν$_{max}$ (film)/cm$^{-1}$ 3583, 3353 br, 2950, 1734, 1660, 1521, 1499, 1454, 1429, 1257, 1214, 1188, 1166, 1051, 911, 737 and 697; δ$_H$ (400 MHz; CDCl$_3$; Me$_4$Si) 1.64 (3H, s, Proα-CH$_3$), 1.72 (1H, dt, J 12.8, 7.6 and 7.6, Prop-H$_A$H$_B$), 1.92 (2H, 5 lines, J 6.7, Proγ-H$_2$), 2.04 (1H, 6 lines, J 7.3 Gluβ-H$_A$H$_B$), 2.17-2.27 (1H, m, Gluβ-H$_A$H$_B$), 2.35-2.51 (3H, m, Prop-H$_A$H$_B$ and Gluγ-H$_2$), 3.37-3.57 (2H, m, Proδ-H$_2$), 3.90 (1H, dd, J 17.0 and 3.6, Glyα-H$_A$H$_B$), 4.00 (1H, dd, J 17.1 and 5.1, Glyα-H$_A$H$_B$), 4.56 (1H, td, J 7.7 and 4.9, Gluα-H), 5.05-5.20 (6H, m, 3×OCH$_2$Ph), 5.66-5.72 (1H, br m, Gly-NH), 7.26-7.37 (15H, m, 3×Ph) and 7.44 (1H, d, J 7.2, Glu-NH); δ$_C$ (100 MHz; CDCl$_3$) 21.9 (CH$_3$, Proα-CH$_3$), 23.4 (CH$_2$, Proγ-C), 26.6 (CH$_2$, Gluβ-C), 30.1 (CH$_2$, Gluγ-C), 38.3 (CH$_2$, Prop-C), 43.9 (CH$_2$, Glyα-C), 47.6 (CH$_2$, Proδ-C), 52.2 (CH, Gluα-C), 66.4 (CH$_2$, OCH$_2$Ph), 66.8 (CH$_2$, OCH$_2$Ph), 67.1 (CH$_2$, OCH$_2$Ph), 68.2 (quat, Proα-C), 127.9 (CH, Ph), 128.0 (CH, Ph), 128.1, (CH, Ph), 128.2, (CH, Ph), 128.2, (CH, Ph), 128.3, (CH, Ph), 128.4, (CH, Ph), 128.5, (CH, Ph), 128.5, (CH, Ph), 135.2 (quat., Ph), 135.7 (quat., Ph), 136.4 (quat., Ph), 156.1 (quat., NCO$_2$), 167.3 (quat., Gly-CO), 171.4 (quat., CO), 172.9 (quat., CO) and 173.4 (quat., CO); m/z (FAB+) 630.2809 (MH$^+$. C$_{35}$H$_{40}$N$_3$O$_8$ requires 630.2815).

Glycyl-L-2-methylprolyl-L-glutamic acid (G-2-MePE)

A mixture of the protected tripeptide 7 (0.63 g, 1.00 mmol) and 10 wt. % palladium on activated carbon (0.32 g, 0.30 mmol) in 91:9 methanol-water (22 cm$^3$) was stirred under an atmosphere of hydrogen at room temperature, protected from light, for 23 h. The reaction mixture was filtered through a Celite™ pad and the pad washed with 75:25 methanol-water (200 cm$^3$). The filtrate was concentrated to dryness under reduced pressure and the residue triturated with anhydrous diethyl ether to afford a 38:1 mixture of G-2-MePE and tentatively methylamine 8 (0.27 g, 86%) as an extremely hygroscopic white solid. Analytical reverse-phase HPLC studies on the mixture [Altech Econosphere C$_{18}$ Si column, 150×4.6 mm, 5 □m; 5 min flush with H$_2$O (0.05% TFA) then steady gradient over 25 min to MeCN as eluent at flow rate of 1 ml/min; detection using diode array] indicated it was a 38:1 mixture of two eluting peaks with retention times of 13.64 and 14.44 min at 207 and 197 nm, respectively. G-2-MePE was shown to be a 73:27 trans:cis mixture of conformers by $^1$H NMR analysis (the ratio was estimated from the relative intensities of the double doublet and triplet at δ 4.18 and 3.71, assigned to the Gluα-H protons of the major and minor conformers, respectively): mp 144° C.$^{\Phi}$; $[\alpha]_D$ −52.4 (c 0.19 in $H_2O$); δH (300 MHz; $D_2O$; internal MeOH) 1.52 (3H, s, Proα-$CH_3$), 1.81-2.21 (6H, m, Prop-$H_2$, Proγ-$H_2$ and Gluβ-$H_2$), 2.34 (1.46H, t, J 7.2, Gluγ-$H_2$), 2.42* (0.54H, t, J 7.3, Gluγ-$H_2$), 3.50-3.66 (2H, m, Proδ-$H_2$), 3.71* (0.27H, t, J 6.2, Gluα-H), 3.85 (1H, d, J 16.6, Glyα-$H_AH_B$), 3.92 (1H, d, J 16.6, Glyα-$H_AH_B$) and 4.18 (0.73H, dd, J 8.4 and 4.7, Gluα-H); δC (75 MHz; $D_2O$; internal MeOH) 21.8 ($CH_3$, Proα-$CH_3$), 25.0 ($CH_2$, Proγ-C), 27.8* ($CH_2$, Gluβ-C), 28.8 ($CH_2$, Gluβ-C), 32.9 ($CH_2$, Gluγ-C), 40.8 ($CH_2$, Prop-C), 42.7 ($CH_2$, Glyα-C), 49.5 ($CH_2$, Proδ-C), 56.0* (CH, Gluα-C), 56.4 (CH, Gluα-C), 69.8 (quat, Proα-C), 166.5 (quat., Gly-CO), 177.3 (quat., Pro-CON), 179.2 (quat., Gluα-CO), 180.2* (quat., Gluγ-CO) and 180.6 (quat., Gluγ-CO); m/z (FAB+) 316.1508 ($MH^+$. $C_{13}H_{22}N_3O_6$ requires 316.1509).

Example 3

In Vitro Neuroprotection

Therapeutic effects of GPE analogs were examined in a series of experiments in vitro to determine their effects on neurodegeneration of neural cells of different origin. The in vitro systems described herein are well-established in the art and are known to be predictive of neuroprotective effects observed in vivo, including effects in humans suffering from neurodegenerative disorders.

Material and Methods

The following experimental protocol followed guidelines approved by the University of Auckland Animal Ethics Committee.

Preparation of Cortical Astrocyte Cultures for Harvest of Metabolised Cell Culture Supernatant One cortical hemisphere from a postnatal day 1 rat was used and collected into 4 ml of DMEM. Trituration was performed using a 5 ml glass pipette and an 18-gauge needle. The cell suspension was sieved through a 100 μm cell strainer and washed in 50 ml DMEM (centrifugation for 5 min at 250 g). The sediment was resuspended in 20 ml DMEM+10% fetal calf serum. The suspension was added into two 25 $cm^3$ flasks (10 ml per flask) and cultivated at 37° C. in the presence of 10% $CO_2$ followed by a change of the medium twice a week. When cells reached confluence, they were washed three times with PBS, adjusted to Neurobasal/B27 and incubated for another 3 days. This supernatant was frozen for transient storage at −80° C.

Preparation of Stratial and Cortical Tissue from Rat E18/E19 Embryos

A dam was sacrificed by $CO_2$-treatment, and then was prepared for caesarean section. After surgery, the embryos were removed from their amniotic sacs and decapitated. The heads were placed on ice in DMEM/F12 medium for striatum and PBS+0.65% D(+)-glucose for cortex.

Striatal Tissue Extraction Procedure and Preparation of Cells

A whole brain was removed from the skull with the ventral side facing upwards in DMEM/F12 medium. The striatum was dissected out from both hemispheres under a stereomicroscope and the striatal tissue was placed into a Falcon tube on ice. Striatal tissue was then triturated using a P1000 pipettor in 1 ml of volume. The tissue was triturated by gently pipetting the solution up and down into the pipette tip about 15 times, using shearing force on alternate outflows. The tissue pieces settled to the bottom of the Falcon tube within 30 seconds. The supernatant containing a suspension of dissociated single cells was then transferred to a new sterile Falcon tube on ice. The tissue pieces were triturated again to avoid excessively damaging already dissociated cells, by over triturating them. 1 milliliter of ice-cold DMEM/F12 medium was added to the tissue pieces in the first tube and triturated as before. The tissue pieces were allowed to settle and the supernatant was removed to a new sterile Falcon tube on ice. The cells were centrifuged at 250 g for 5 minutes at 4° C.

Plating and Cultivation of Striatal Cells

Striatal cells were plated into Poly-L-Lysine (0.1 mg/ml) coated 96-well plates (the inner 60 wells only) at a density of 200,000 cells/$cm^2$ in Neurobasal/B27 medium (Invitrogen). The cells were cultivated in the presence of 5% $CO_2$ at 37° C. under 100% humidity. Medium was changed on days 1, 3 and 6.

Cortical Tissue Extraction Procedure and Preparation of Cells

The two cortical hemispheres were carefully removed by spatula from the whole brain with the ventral side facing upside into a PBS+0.65% D(+)-glucose containing petri dish. Forceps were put into the rostral part (near *B. olfactorius*) of the cortex in order to fix the tissue and two lateral-sagittal oriented cuts were made to remove the paraform and entorhinal cortices. A frontal oriented cut at the posterior end was made to remove the hippocampal formation. A final frontal cut was done a few millimeters away from the last cut in order to get hold of area 17/18 of the visual cortex.

Cortices were placed on ice in PBS+0.65%(+)-glucose and centrifuged at 350 g for 5 minutes. The supernatant was removed and trypsin/EDTA (0.05%/0.53 mM) was added for 8 min at 37° C. The reaction was stopped by adding an equal amount of DMEM and 10% fetal calf serum. The supernatant was removed by centrifugation followed by two subsequent washes in Neurobasal/B27 medium.

The cells were triturated once with a glass Pasteur pipette in 1 ml of Neurobasal/B27 medium and subsequently twice by using a 1 ml insulin syringe with a 22 gauge needle. The cell suspension was passed through a 100 μm cell strainer and rinsed by 1 ml of Neurobasal/B27 medium. Cells were counted and adjusted to 50,000 cells per 60 μl.

Plating and Cultivation of Cortical Cells 96-well plates were coated with 0.2 mg/ml Poly-L-Lysine and subsequently coated with 2 μg/ml laminin in PBS, after which 60 μl of cortical astrocyte-conditioned medium was added to each well. Subsequently, 60 μl of cortical cell suspension was added. The cells were cultivated in the presence of 10% $CO_2$ at 37° C. under 100% humidity. At day 1, there was a complete medium change (1:1—Neurobasal/B27 and astrocyte-conditioned medium) with addition of 1 μM cytosine-β-D-arabino-furanoside (mitosis inhibitor). On days 2 and 5, ⅔ of the medium was changed.

Cerebellar Microexplants from P8 Animals: Preparation, Cultivation and Fixation

Laminated cerebellar cortices of the two hemispheres were explanted from a P8 rat, cut into small pieces in PBS+0.65% D(+) glucose solution and triturated with a 23 gauge needle and subsequently pressed through a 125 μm pore size sieve. The obtained microexplants were centrifuged (60 g) twice (media change) into serum-free BSA-supplemented STARTV-medium (Biochrom). For cultivation, 40 μl of cell suspension was adhered for 3 hours on a 0.1 mg/ml Poly-L-Lysine coated cover slip placed in 35 mm sized 6 well plates in the presence of 5% $CO_2$ under 100% humidity at 34° C. Subsequently, 1 ml of STARTV-medium was added together with the toxins and drugs. The cultures were monitored (evaluated) after 2-3 days of cultivation in the presence of 5% $CO_2$ under 100% humidity. For cell counting analysis, the cultures were fixed in rising concentrations of paraformaldehyde (0.4%, 1.2%, 3% and 4% for 3 min each) followed by a wash in PBS.

Toxin and Drug Administration to Neural Dells In Vitro and Analysis of Data

To study neuroprotective effects of GPE analogs, we carried out a series of experiments in vitro using okadaic acid to cause toxic injury to neural cells, Okadaic acid is an art-recognized toxin that is known to cause injury to neurons. Further, recovery of neural cells or neural cell function after injury by okadaic acid is recognized to be predictive of recoveries from injuries caused by other toxins.

To cause toxic injury to neurons, we exposed neurons to 1:100 parts of okadaic acid at concentrations of 30 nM or 100 nM and 0.5 mM 3-nitropropionic acid (for cerebellar microexplants only). GPE (1 nM-1 mM) or G-2-MePE (1 nM-1 mM) was used at 8 days in vitro (DIV) for cortical cultures and 9DIV for striatal cultures. The incubation time was 24 hours. The survival rate was determined by a colorimetric end-point MTT-assay at 595 nm in a multi-well plate reader. For the cerebellar microexplants four windows (field of 0.65 mm$^2$) with highest cell density were chosen and cells displaying neurite outgrowth were counted.

Results

The GPE analog G-2-MePE exhibited comparable neuroprotective effects within all three tested in vitro systems (FIGS. 12-15).

Cortical cultures responded to 10 μM concentrations of GPE (FIG. 12) or G-2-MePE (10 μM, FIG. 13) with 64% and 59% neuroprotection, respectively.

The other 2 types of cultures demonstrated neuroprotection at lower doses of G-2-MePE (cerebellar microexplants: FIG. 14 and striatal cells: FIG. 15). Striatal cells demonstrated neuroprotection within the range of 1 nM to 1 mM of G-2-MePE (FIG. 15), while the postnatal cerebellar microexplants demonstrated neuroprotection with G-2-MePE in the dose range between about 1 nM and about 100 nM (FIG. 14). Thus, we conclude that G-2-MePE is a neuroprotective agent and can have therapeutic effects in humans suffering from neurodegenerative disorders. Because G-2-MePE can be neuroprotective when directly administered to neurons in culture, that G-2-MePE can be effective in vivo when directly administered to the brains of affected animals.

Example 4

Effects of G-2-MePE on Striatal Cholinergic Neurons in Aging Rats

To determine whether G-2-MePE can affect cholinergic neurons, we studied aging rats. Choline acetyltransferase (ChAT) is an enzyme that is involved in the biosynthesis of the neurotransmitter for cholinergic nerves, acetylcholine. It is well known that immunodetection of ChAT can be used to determine the numbers of cholinergic nerves present in a tissue. It is also known that the numbers of cholinergic nerves present is associated with the physiological function of cholinergic neural pathways in the brain.

In this experiment, we tested the effects of G-2-MePE on the number of ChAT-positive neurons in brains of 18-month old rats.

Methods

Eighteen-month old male rats received one of five treatments. A control group was treated with vehicle (saline alone (n=4) and four groups were treated with a single dose of G-2-MePE. Doses of 0.012 (n=4), 0.12 (n=5), 1.2 (ln=5) and 12 mg/kg (n=3), respectively, were given sub-cutaneously.

Rats were sacrificed with an overdose of pentobarbital 3 days after drug treatment. Brains were perfused with normal saline and 4% paraformaldehyde and fixed in perfusion fixative overnight. Brains were stored in 25% sucrose in 0.1M PBS (pH7.4) until the tissue sank. Frozen coronal sections of striatum were cut with a microtome and stored in 0.1% sodium azide in 0.1M PBS at 4° C. Immunoreactivity for choline acetyltransferase (ChAT) was established by staining using a free floating section method. Briefly, antibodies were diluted in 1% goat serum. The sections were incubated in 0.2% triton in 0.1M PBS/Triton™ at 4° C. overnight before Immunohistochemical staining. The sections were pre-treated with 1% $H_2O_2$ in 50% methanol for 20 min. The sections were then incubated with rabbit (Rb) anti-ChAT (1:5000) antibodies (the primary antibodies) in 4D on a shaker for two days. The sections were washed using PBS/Triton™ (15 minutes×3d) and then incubated with goat anti-rabbit biotinylated secondary antibodies (1:1000) at room temperature overnight. The sections were washed and incubated in ExtrAvidin™ (Sigma) (1:1000) for 3 hours and followed by $H_2O_2$ (0.01%) in 3,3-diaminobenzine tetrahydrochloride (DAB, 0.05%) to produce a coloured reaction product. These sections were mounted on chrome alum-coated slides, dried, dehydrated and covered.

The striatal neurons in both hemispheres exhibiting specific immunoreactivities corresponding to ChAT were counted using a light microscope and a 1 mm 2×1000 grid. The size of the striatal region used for the count was measured using an image analyser. The total counts of neurons/mm$^2$ were compared between the groups.

Data were analysed using a paired t-test and presented as mean+/−SEM. Results are presented in FIG. 16.

Results

FIG. 16A shows that the number of ChAT-immunopositive neurons increased in the brains of animals treated with G-2-MePE. This clearly indicates that administration of G-2-MePE is effective in increasing the level of ChAT in the brains of aged rats. Because ChAT is an enzyme involved in the synthesis of the cholinergic neurotransmitter acetylcholine, we conclude that G-2-MePE can increase the amount of cholinergic transmitter in the brains of middle-aged rats.

Example 5

Effects of G-2-MePE on Spatial Reference Memory in Rats

Having demonstrated that G-2-MePE can increase ChAT and therefore has the potential to improve cholinergic neural function, we then examined whether G-2-MePE can be useful in treating age-related changes in cognition and/or memory. Therefore, we carried out a series of studies in rats using well-established tests for memory.

Experiment 1

The Morris Water Maze Test

The Morris water maze test is a well-recognized test to assess spatial reference memory in rats.

Subjects

We used male Wistar rats 12, 8 or 4 months of age.

Methods

Testing Environment and Apparatus

The Morris water maze test was conducted using a black plastic pool filled to a depth of 25 cm with water colored black with a non-toxic dye. The pool had a circular black insert so that the walls also appeared uniform black The pool was divided into four quadrants (north, south, east and west) by two imaginary perpendicular lines crossing at the pool's center A metal platform was placed in the geographical centre of the SE quadrant 50 cm from the edge of the pool, so that it was 2 cm below the water surface and invisible. The platform remained in that position though the training.

The experiment used extra-maze cues (i.e. objects in the room surrounding the pool) that the rats could use to navigate to the platform. Distinctive posters or paintings were hung on the walls. Furniture in the room was not moved during the testing period. The placement of the pool allowed the experimenter an easy access to it from all sides. The pool was emptied and refilled daily during testing, with water at 25° C.+/−2° C.

The furthermost point in the pool (relative to the position of the experimenter) was designated as "north", and the other compass points "east", "south" and "west" were the rightmost, bottom and left-most points of the pool respectively. These points were marked with tape on the outside of the pool.

Acquisition Phase

Rats in each group were trained to swim to the submerged platform. The rats received six 60-second trials per day for four consecutive days. A trial began by placing the rat into the water facing the wall of the pool, at one of four start locations (north, south, east, west). The sequence of start locations was chosen pseudorandomly, so that the start location of any given trial was different from that of the previous trial, and no start location was used more than twice during daily training. The same sequence of locations was used for all the rats on a given day but varied between days. The trial ended when the rat had found the platform, or in 60 seconds, which ever occurred first. The trials were timed with a stop watch. If the rat found the platform, it was allowed to remain there for 15 seconds before being removed to a holding container. If the platform was not found, the rat was guided there manually and placed on the platform for 15-seconds. The inter-trial interval was 60 seconds. The holding container was covered in order to minimize any inter-trial interference. At the completion of daily testing for a rat, the animal was towel-dried and placed under the heat lamp in the holding bucket until his coat was dry. The time needed to locate the platform (latency, sees) was obtained for each rat in each training trial. If the rat did not find the platform in a given trial their latency score was the maximum length of that trial (60 seconds).

Drug Treatment

Three days after the completion of the acquisition phase, mini-osmotic pumps (Alzet) were implanted subcutaneously under halothane anesthesia) to dispense drug or vehicle continuously for 1 or 3 weeks. At the completion of the infusion the pumps were removed and the wounds re-sutured.

The 5 treatment groups were:
1. saline 1 week (n was originally 7, but one rat that lost weight rapidly was excluded and later found to have had a pituitary tumor);
2. saline 3 weeks (n=8);
3. G-2-MePE low dose (0.96 mg/day) 1 week (n=8);
4. G-2-MePE low dose (0.96 mg/day) 3 weeks (n=8);
5. G-2-MePE high dose (4.8 mg/day) 3 weeks (n=7).

The four (n=3) and eight month old (n=9) control rats received no drug treatment. The 12-month old rats were assigned to one of five groups on the basis of their swim times over acquisition, such that the groups were approximately equivalent in their mean performance prior to receiving any drug.

Retention (Reference Memory) Phase

The ability of the rats to remember or to relearn the original platform location was tested four weeks after original training. This means that residual drug would have been washed out for a minimum of 7 days in the case of the 3-week pumps, and 21 days in the case of the 1-week pumps. The retention testing procedure was identical to that of acquisition. Pharmacokinetic studies indicate that the plasma concentration of subcutaneously administered G-2-MePE rose to a peak and then declined with an approximately first order kinetic pattern, with a plasma half-life (t 2) of between about 30 and 60 minutes. Thus, by the time the retention study was performed, at least 7 days after removal of the G-2-MePE containing minipumps, nearly all of the G-2-MePE had been cleared from the animals' circulation.

Data Analysis

The swim latency for each rat was recorded for each trial for each day of the acquisition and retention phases and changes between phases were examined using Analysis of Variance.

The 3-week vehicle and 3-week high dose G-2-MePE were compared in acquisition and retention. The high dose of G-2-MePE, given over 3 weeks improved the retention of the original water maze task after a 4-week delay.

Results

FIG. 17 shows the comparison between high-dose (4.8 mg/day) G-2-MePE-treated and low-dose-treated (0.96 mg/day) aged rats and saline treated aged rats, with the young controls (4 months) used as controls. Prior to treatment with G-2-MePE, there were no differences between the aged (12 month old) groups. In contrast, the 4 month old animals required less time to reach the platform than older animals. After a 3-week period of no testing, during which time either saline or G-2-MePE were administered, animals that received saline only did not show improved ability to reach the platform, as indicated by the similar times required at test day 4 of the acquisition phase and test day 1 of the retention phase. In contrast, animals that received treatment with G-2-MePE at either the high or low doses, had improved memory as reflected in a decrease in the time needed to reach the platform compared to saline-treated controls. Further, the G-2-MePE-treated animals had similar performance to the 4 month old young animals (FIG. 17) and 8 month old animals (data not shown). Thus, we conclude that G-2-MePE can improve memory in middle-aged rats animals that had previously shown memory deficits in relation to young rats. Further, because by the time of retesting, the G-2-MePE had washed out from the circulation, we conclude that the memory-enhancing effects of G-2-MePE were likely due to the improvement in function of cholinergic neurons.

Experiment 2

8-Arm Radial Maze Test

Five months after the original experiment the now 17 month old rats were retested for spatial working memory in a radial arm maze.

Methods

Apparatus

The apparatus consists of a central platform communicating with 8 identical arms, each with a food cup at the end of the arm Testing Procedure Rats were partially food-deprived for at least 10 days prior to, and throughout the radial maze procedure.

The maze was assembled and positioned so that the experimenter could clearly observe the rats' behavior from a predetermined location. The experimenter numbered the arms of the maze according to their orientation from one to eight in a clock-wise direction.

Pre-Training (Pre-Drug)

On day one the doors were inserted into the arms and each rat was confined in the central platform with 20 food pellets for 5 minutes. This continued once a day for four days, and all of the rats were observed to consume some of the pellets. The following day the rats were allowed five minutes to explore the whole maze. All arms were baited with two food pellets in the food cup located at the end of each arm, and one pellet at both the entrance and middle of each arm. This was repeated for at least five, but up to eight days for rats that explored fewer than eight arms in two consecutive sessions. All rats had a final session on the ninth day of pre-training. At this point it was decided that one of the old rats that had made only one arm entry on eight of the nine days should be excluded from future testing in this procedure. Otherwise all rats were included regardless of the amount of exploring they performed in pre-training. There was no statistically significant difference between the old groups in the number of arms entered on the final pre-training session (Drug: $F(2,31)=0.44$, $p=0.65$).

Drug Treatment 30 days before the test (five days after pre-training) the 17 Male Wistar month old rats were implanted (under halothane anesthesia) with sub-cutaneous mini-osmotic pumps (Alzet) to dispense drug continuously for 3 weeks. At the completion of the infusion the pumps were removed and the wounds re-sutured (9-day washout allowed).

The treatment groups were:
1. young controls (4 months old), n=6;
2. saline n=10;
3. G-2-MePE low dose (2.4 mg/kg/day) n=13
4. G-2-MePE high dose (12.4 mg/kg/day) n=5

Saline and the low dose groups are comprised of all the rats that received those treatments in phase 1 of this experiment (when the rats were 12 months old) regardless of whether they had the one or three week treatment. One rat in each of the saline and high dose groups have been dropped because of skin tumors. One of the low dose rats did not participate in this experiment due to the fact that it could not be pre-trained (see below).

Testing (Post-Drug)

Working memory testing commenced on the ninth day of washout. Rats received 10 daily training sessions over 12 days. The procedure was the same as for pre-training but only the food cups were baited. Rats had 6 minutes to make up to 16 choices by visiting any of the eight arms. A choice was defined as occurring when all four paws were inside an arm. The experimenter recorded the sequence of arm entries with pen and paper, Sessions were terminated after all eight arms had been entered, 16 choices made, or 6 minutes had elapsed. The time taken to enter all eight arms, when this occurred, was recorded.

Data Analysis

An arm choice was considered correct when the rat entered an arm not previously visited. Performance was classified daily according to the following parameters:

1) Correct Choice (CC) 8-12 is the number of correct choices made divided by the total number of choices made. For animals that failed to visit all 8 arms in a test, the denominator of this ratio is considered to be 12.

2) Working Correct Choice (WCC) 8-12 is the measure from which the working memory data are derived. Data were collected as described for CC 8-12 above, but for this parameter, only the rats that entered all 8 arms in a session were included.

Rats that made fewer than 8 arm entries were not used to ascertain working memory because they couldn't remember which arms they had previously visited and therefore had memory so impaired that they could not complete the test, as opposed to the animals that, for whatever reason, did not explore the maze.

Results

CC8-12: There was a general improvement by all of the groups across the 10 days ($F(9,324)=4.01$, $p<0.0001$), but no significant group effect ($F(3,36)=1.19$, ns) or Group X Days interaction ($F(27,324)=1.05$, ns) (data not shown)

WCC8-12: FIG. 18A shows the acquisition profile according to WCC8-12 score across the 10 days of testing. There was a significant effect of Group ($F(3,12)=4.27$, $p=0.029$) and Days ($F(9,108)=2.09$, $p=0.036$) but the interaction between these factors was not significant ($F(27,108)=1.06$, ns). The high dose G-2Me-PE group showed the greatest improvement across days, followed by the young controls. There was very little difference between the low dose G-2Me-PE and saline.

FIG. 18B shows results indicating that rats exposed to the higher dose of G-2-MePE (n=5) had made more correct entries for getting food pellets compared to the vehicle treated rats (*$p<0.05$, n=10). We conclude from this study that G-2-MePE improves spatial memory in aged rats.

Example 6

G-2-MePE Increases Neuroblast Proliferation and Decreases Astrocytosis in Brains of Aged Rats Because neuronal degeneration can result in decreased numbers of neurons, one desirable therapeutic aim is increasing the numbers of neurons in the brain. Neurons are derived from neuroblasts, a less differentiated cell than a neuron, but within the neural lineage. Typically, a neuroblast is exposed to conditions that cause it to mature into a mature phenotype, having a defined soma, neural processes (axons and dendrites) and ultimately, making connections with other neurons (e.g., synapses). Thus, measuring neuroblast proliferation has become a well-known early marker for nerve cell proliferation. Thus, detecting an increase in neuroblast proliferation induced by a pharmaceutical agent is an accepted method for predicting growth of neural cells in animals. Because rats and humans share similar mechanisms in neural cell proliferation, detection of changes in neuroblast proliferation in rats in vivo is predictive of similar effects in human beings.

It is also known that one histological correlate of impaired cognitive function is an increase in the numbers of astrocytic cells in the brain of affected animals. Thus, to determine whether G-2-MePE might be useful in stimulating neuroblast proliferation and in treating astrocytosis, we carried out a series of studies in aging rats.

Methods and Materials

Immunohistochemistry

To carry out these studies, tissues were fixed and embedded in paraffin and sections obtained using standard methods. Coronal sections (6 μm) containing the level of the hippocampus were cut and mounted on chrome-alum-coated slides for staining. The sections were deparaffinized in xylene, dehydrated in a series of ethanol and incubated in 0.1 M phosphate buffered saline (PBS).

Primary antibodies against glial fibrillary acidic protein (GFAP) and proliferating cell nuclear antigen (PCNA) were used to mark reactive glial cells and cells undergoing apoptosis and proliferation, respectively. For antigen unmasking (caspase-3 and PCNA staining), sections were heated in 10 mM sodium citrate buffer (pH 6.0) for 1 min at high power. All sections were pretreated with 1% $H_2O$ in 50% methanol for 30 min to quench the endogenous peroxidase activity. Then either 1.5% normal horse serum or 2.5% normal sheep serum in PBS was applied for 1 h at room temperature to block nonspecific background staining. The sections were then incubated with following primary antibodies: monoclonal mouse anti-GFAP antibody (Sigma, St. Louis, Mo., U.S.A. diluted 1:500); mouse anti-PCNA antibody (DAKA, A/S, Denmark, diluted 1:100). After incubation with primary antibodies at 4° C. for 2 d (except for PCNA staining which was incubated overnight) the sections were incubated with biotinylated horse anti-mouse or goat anti-rabbit secondary antibody (1:200, Sigma) at 4° C. overnight. The ExtrAvidin™ (Sigma, 1:200), which had been prepared 1 h before use, was applied for 3 h at room temperature, and then reacted in 0.05% 3,3-diaminobenzidine (DAB) and PBS to produce a brown reaction product. Sections were dehydrated in a series of alcohols to xylene and coverslipped with mounting medium.

Immunohistochemical staining was performed on brain samples taken from both control and G-2-MePE treated groups of young (4 months old), middle-aged (9 months old) and aged rats (18 months old).

Control sections were processed in the same way except the primary antibody was omitted from the incubation solution. The number of PCNA positive cells was counted in the subventricular zone and the GFAP positive cells was scored in the cerebral cortex.

Experiment 1

G-2-MePE Stimulates Neuroblast Proliferation in Brains of Aged Rats

The subventricular zone (SVZ) and the dentate gyrus (DG) are two brain regions hosting adult neurogenesis. The reduction of neurogenesis in both SVZ and the DG has been well reported to be co-related to the memory decline with aging and effects of Nerve Growth Factor and Epidermal Growth Factor on memory improvement are reported to be due to increase in progenitors proliferation of the SVZ. Using PCNA as a marker of cell proliferation, cellular proliferation in the SVZ was examined by counting the numbers of cells that are positive for PCNA. In selected animals, at least some of the proliferating cells were identified as neuroblasts, as stained with the neural-cell specific agent, doublecortin.

Eighteen month old male rats were treated intraperitoneally with single does of G2-MePE (doses of either 0, 0.012, 0.12. 1.2, 12 mg/kg). Brains were collected 3 days after the treatments and the immunohistochemical staining of PCNA and GFAP were performed. The number of PCNA positive cells was counted in the SVZ and the number of cells was then averaged as cells/mm depending on the length of ventricle wall used for counting (FIG. 19A). The group treated with the highest dose (12 mg/kg, n=5) showed a significant increase in the number of PCNA positive cells compared to the group treated with vehicle (*p<0.05, n=7). The data indicated a dose-dependent effect of G-2PE on improving neurogenesis.

Fluorescence double labelling indicated co-localisation of PCNA with doublecortin, a marker for neuroblasts. FIG. 19B is a photograph of a portion of a rat's brain showing an increase in both PCNA (green, ×20) and doublecortin (red, ×20) in the rat treated with the highest dose of G-2-MePE (right panel) compared to the vehicle treated rat (left panel). The two markers clearly co-localised (FIG. 19B, photo, ×100). We conclude that G-2-MePE can stimulate proliferation of brain cells, including neuroblasts. Because neuroblasts are precursor cells for neurons; we further conclude that G-2-MePE can increase the population of neurons in the brains of animals treated with the compound of this invention.

Experiment 2

G-2-MePE Stimulates Neuroblast Proliferation in the SVZ of Brains of Middle-Aged Rats Effects of G-2-MePE (1.2 mg/kg) were studied in a group of middle-aged, 9 month old rats. G-2-MePE (1.2 mg/kg) or vehicle was administered intraperitoneally (i.p.). The proliferation of cells in the SVZ was examined 3 days after the treatment using PCNA immunohistochemical staining. FIG. 19C shows a significant increase in number of PCNA positive cells after the treatment of G-2-MePE (**p<0.005, n=4). Because some of the proliferating cells stained with PCNA were identified as neuroblasts (see Experiment 1 above), we conclude that G-2-MePE can stimulate neuroblast proliferation in middle-aged rat brains.

Experiment 3

Astrocytosis in Aging Brains

Growing evidence suggests that dysfunction of astrocytes in advanced age can trigger inflammation, leading to further neuronral degeneration. Up-regulation of activated astrocytes has been well reported and is closely associated with memory decline with aging, perhaps through depressed endogenous neurogenesis.

Using GFAP as a marker for reactive astrocytes, the number of GFAP-positive cells was counted in the CA4 sub-region of the hippocampus of aged rats treated with G-2MeP or vehicle. We found a significant increase in reactive astrocytes in the hippocampus of aged animals (FIG. 20A), and in the cerebral cortex. Some of the astrocytes were associated with capillaries (FIG. 20B photo, arrows) in aged rats compared to both young (*p<0.01) and middle aged rats (*#p<0.01).

As part of the vascular component, GFAP positive astrocytes also play a role in angiogenesis (FIG. 20B, arrows), which also contribute to inflammatory response in brains. Therefore the elevated GFAP astrocytes seen in aged brains may indicate a chronic stage of brain degeneration.

Experiment 4

G-2-MePE Reduces Astrocytosis in Aged Brains

We also evaluated effects of G-2-MePE on astrocytosis in the CA4 sub-region of the hippocampus in aged rats. 18-month old male Wistar rats were assigned to 5 treatment groups as follows: vehicle, 0.12 mg/kg/day, 0.12, 1.2 and 12 mg/kg/day (each n=6).

GFAP-positive cells were counted using a computerised program (Discovery 1). Results are shown in FIGS. 20C and 20D. G-2-MePE was administered intra-peritoneally and the numbers of GFAP-positive cells were assessed 3d after the injection. Using a visual scoring system (0=no astrocytes, 1=few astrocytes, 2<50%, 3>50%) we estimated the number of astrocytes in 5 different cortical regions.

Treatment with G-2-MePE reduced number of reactive astrocytes in the CA4 region of the hippocampus compared to the vehicle treated group (FIG. 20C; *p<0.05), particularly the groups treated with doses of 0.12 and 12 mg/kg. A similar effect was observed for G-2-MePE in the cerebral cortex (FIG. 20D).

Normally there are few GFAP-positive astrocytes located in the deep layer of cortex of rat brains and those that are present are usually in close association with white matter tracks. However, we have found there were GFAP-positive cells in the middle layer of the cortex, closely associated with blood vessels.

Results of the studies presented herein indicate that aging is associated with several changes in the brain. First, there is an age-dependent loss of memory and cognitive function, Second, there is an age-depended increase in astrocytes. All of these findings in the rat are consistent with each other and the known roles of cholinergic nerves in maintaining cognitive function and memory in experimental animals and in humans.

We unexpectedly found that a GPE analog, G-2-MePE, delivered to aged animals at least partially reverses all of the above age-associated changes. First, G-2-MePE increases the amount of ChAT present in the brain cells of animals exposed to the neurotoxins okadaic acid or 3-NP. This effect of G-2-MePE mimicked that of a well-known neuroprotective agent, GPE. These effects were seen in cortical cells, cerebellar cells and in striatal cells, indicating that the effects were widespread in different portions of the brain. Second, G-2-MePE increased ChAT in the striatum, indicating that cholinergic neurons are sensitive to G-2-MePE. These observed chemical and histological changes were paralleled by behavioral changes. Aged animals treated with G-2-MePE exhibited improved memory in two well-known test systems compared to vehicle-treated controls. Next, G-2-MePE induced neuroblast proliferation in aging brains. Finally, treatment with G-2-MePE reversed the increase in astrocytosis observed in the hippocampus and cortex of aging brains. The effects of G-2-MePE were not due to acute effects of the agent; because in many of the studies cited herein, sufficient time had elapsed from cessation of drug delivery to the test, that there was likely little or no drug present.

Example 7

Comparison of the Pharmacokinetics of GPE and G-2-MePE

The purpose of these studies was to compare pharmacokinetic profiles of GPE and G-2-MePE in animals in vivo using standard pharmacokinetic methods.

Methods

Adult male Wistar rats weighing between 180 and 240 g were used to determine the pharmacokinetics of GPE and G2MePE. To facilitate intravenous bolus injections and blood sampling, all rats were surgically implanted with an indwelling jugular venous cannula under halothane anesthesia three days before the experiment. Groups of six rats were given a single intravenous bolus injection of either 30 mg/kg GPE or 10 mg/kg G2MePE dissolved in 0.1M succinate buffer (pH 6.5). Blood samples (about 220 µl each) were collected into heparinized tubes containing Sigma protease inhibitor cocktail for mammalian tissues at 10 and 0 min before injection of either GPE or G2MePE, and 1, 2, 4, 8, 16, 32, 64 and 128 min after injection of either GPE or G2MePE. The samples were centrifuged at 3000 g for 15 min at 4° C. and the plasma removed and stored at −80° C. until extraction and assay by either radioimmunoassay ("RIA") or reverse phase HPLC. The RIA and HPLC methods used were conventional.

Drug elimination after a single intravenous bolus injection was found to be a first-order process following the equation $C=C_0 e^{-kt}$, where C represents drug concentration in any time point, $C_0$ is the concentration when time (t) equals zero and k is the first-order rate constant expressed in units of concentration per hour. The k and half-life ($t_{1/2}$) were calculated from the slope of the linear regression line in the elimination phase of the semi-logarithmic plot of plasma concentration versus time as: Log. $C=-kt/2.3+\log C_0$. Results were expressed as mean±standard error.

Results

FIG. 21 shows a graph of plasma concentrations in vivo of GPE and G-2-MePE after intravenous (i.v.) injection. Filled squares represent concentrations of GPE at each time point, and filled triangles represent concentrations of G-2-MePE at each time point.

Plasma concentrations of GPE and G-2-MePE were markedly increased within 1 min after injection. After injection of 30 mg/kg GPE, a peak concentration of 40.0 t 10.8 mg/ml was observed. Plasma concentrations of GPE then rapidly declined according to a first-order kinetic process. The first order rate constant for GPE was found to be 0.15±0.014 ng/ml/min, the $t_{1/2}$ was found to be 4.95±0.43 min and the estimated clearance of GPE from plasma was found to be 137.5±12.3 ml/hr.

After injection of 10 mg/kg G-2-MePE, the peak concentration was found to be 191±16.1 mg/ml. Plasma concentrations of G-2-MePE then declined according to a first-order kinetic process. The first order rate constant for G-2-MePE was found to be 0.033±0.001 ng/ml/min, the tin was found to be 20.7±0.35 min and the estimated clearance was found to be 30.1±0.5 ml/hr.

After injection, the maximal plasma concentration of G-2-MePE was about 4.8 times greater than the maximal plasma concentration of GPE, in spite of the larger dose of GPE delivered (30 mg/kg) compared to the dose of G-2-MePE delivered (10 mg/kg).

The finding of greater plasma concentrations of G-2-MePE than for GPE at all time points less than 125 minutes, in spite of a lower delivered dose of G-2-MePE, was totally unexpected based on known plasma concentrations of GPE. The $t_{1/2}$ for G-2-MePE was over 4 times longer than the tin for GPE.

The finding of increased half-life of G-2-MePE compared to that of GPE was completely unexpected based on the $t_{1/2}$ of GPE. The increased $t_{1/2}$ of G-2-MePE means that G-2-MePE is cleared more slowly from the circulation. This finding is totally unexpected based on the clearance rate of GPE.

We conclude from these studies that G-2-MePE is a potent agent capable of reversing many of the adverse effects of aging in the brains of animals, including humans. GPE analogs, including G-2-MePE therefore, can produce desirable therapeutic effects, including neuroprotection, improved memory, increased neuroblast proliferation and reduction in astrocytosis, and can be valuable in reversing or mitigating adverse effects of aging in humans.

While this invention has been described in terms of certain preferred embodiments, it will be apparent to a person of ordinary skill in the art having regard to that knowledge and this disclosure that equivalents of the compound of this invention may be prepared and administered for the conditions described in this application, and all such equivalents are intended to be included within the claims of this application.

Example 8

Treatment of Rett Syndrome I Effects of G-2-MePE on Lifespan and Long-Term Potentiation in Rett Syndrome (RTT) Model To determine whether G-2-MePE treatment can impact the development and progression of Rett Syndrome in a murine model of the disorder, we used hemizygous MeCP2(1lox) male mice. The MeCP2 knock-out (MeCP2-KO) mouse system is widely accepted in the art as closely mimicking the range and the severity of physiological and neurological abnormalities characteristic of the human disorder, Rett Syndrome.

All experiments were performed at the University of Texas Southwestern Medical Center and approved by the University of Texas Southwestern Medical Center Animal Care and Use Committee. G-2-MePE was synthesised Albany Molecular Research Inc. (Albany, N.Y.) and supplied by Neuren Pharmaceuticals Limited.

Methods

Treatment

We treated hemizygous MeCP2(1lox) male mice with 20 mg/kg/day of G-2-MePE or saline, (0.01% BSA, n=15 per group in survival experiment and n=20 in the LTP experiment). The treatments were administered intraperitoneally from 4 weeks after birth. For the survival experiments the treatment was maintained through the course of the experiment. For the LTP experiment the mice were treated until week 9 when they were used for slice preparation.

Survival

MeCP2 deficient mutant mice develop RTT symptoms at about 4-6 weeks of age and die between 10-12 weeks (Chen et al., 2001. Nat Genet 27: 327-331). We compared the survival of the wild type controls and the MeCP2 deficient animals in vehicle- and G-2-MePE-treated groups. Survival was measured weekly from start of treatment (4 weeks) and used to produce Kaplan-Meier survival curves to show the proportion of mice that survived (y axis) at each weekly interval (x axis) (see FIG. 22).

Long-Term Potentiation (Electrophysiology)

MeCP2 deficient mice have been previously reported to suffer from functional and ultrastructural synaptic dysfunction, significant impairment of hippocampus-dependent memory and hippocampal long-term potentiation (LTP) (Moretti et al. The Journal of Neuroscience. 2006. 26(1):319-327). To test the effects of the G-2-MePE treatment on synaptic function in the RTT model we compared hippocampal LTP in both vehicle and G-2-MePE treated animals at 9 weeks of age. To do so, we measured the slope of the fEPSP as a % of baseline potential in neurons in slices of hippocampus from MeCP2 deficient mice treated with either saline or G-2-MePE (FIG. 23).

Results

FIG. 22 shows that G-2-MePE treatment increased survival of MeCP2 deficient mice. Wild-type mice (top line) are control animals, and therefore their survival was 100% at each time point. MeCP2 deficient mice treated with saline only died much more rapidly (dotted line) than wild-type mice, such that by about 11 weeks, only 50% of the MeCP deficient mice survived. In striking contrast, however, we unexpectedly found that MeCP2 deficient mice treated with G-2-MePE survived substantially longer than saline-treated mice. At about 15 weeks, 50% of the animals survived. Data initially presented showed that MeCP2 mice were impacted in terms of survival such that 50 percent of animals had died by 11 weeks in the untreated case. G-2-MePE treated animals showed improved survival, with 50 percent having died at 16 weeks. In this study, the longevity data were compromised by inconsistent veterinary procedures, such that mice did not have their teeth clipped consistently—a requirement in mecp2 mice unrecognized at the start of the experiment. A consequence was the observation of early animal deaths unrelated to Rett Syndrome (particularly in the control group). Re-examination of the data showed that the effect of G-2-MePE persisted when the control group was re-run, albeit the difference in groups being smaller (time to 50 percent death 13.5 weeks in controls, 16 weeks in G-2-MePE treated animals). No safety concerns were raised by G-2-MePE treatment of mecp2 mice.

These results demonstrated that G-2-MePE can substantially increase survival of MeCP2 deficient mice. Because MeCP2 deficient mice are predictive of the pathology and therapeutic efficacy in human beings with Rett Syndrome, we conclude that G-2-MePE can increase life span of human beings with Rett Syndrome.

FIG. 23 shows results of our studies to determine if G-2-MePE treatment increased hippocampal long-term potentiation (LTP) as measured by the fEPSP slope in MeCP2 deficient animals compared to saline-treated mutant mice. As shown in FIG. 23, we unexpectedly found that G-2-MePE increased the slope of fESPS in MeCP2 deficient mice compared to animals treated with saline only.

These results demonstrated that G-2-MePE can be effective in treating MeCP2 deficient mice in vivo. Because MeCP2 deficient mice are predictive of the pathology and therapeutic efficacy in human beings with Rett Syndrome, we conclude that G-2-MePE can be an effective therapy for people with Rett Syndrome.

Example 9

G-2-MePE Improves Dendritic Arborization and Increases Dendritic Spine Length We assess the effects of G-2-MePE treatment on dendrites. Transgenic mecp2 knockout mice (n=15 to 20) were administered G-2-MePE intraperitoneally at a dose of 20 mg/kg once daily. Following sacrifice dendritic spine density, spine length and aborization were examined after Golgi staining after nine weeks, as per the Table 1 below:

TABLE 1

Sample size for all neuron morphologic and spine analysis

| Analysis | AGE (Weeks) | MALE Sample size (no. of mice) | | Sample size (average number of neurons or dendrites per animal) | |
| --- | --- | --- | --- | --- | --- |
| | | KO-vehicle | KO-NNZ-G-2MePE | KO-vehicle | KO-NNZ-G-2MePE |
| Neuron morphology | 9 | 3 | 3 | 4 | 4 |
| Spine Analysis | 9 | 3 | 3 | 10 | 10 |

Dendritic length was assessed by distance from the soma of representative hippocampal CA1 neurons from 9 week old male mecp2 null mutant mice treated with either saline (3 neurons analysed from 3 separate mice, n=9) or G-2-MePE (20 mg/kg i.p. 1/day, from week 4; 3 neurons analysed from 3 separate mice, n=9).

We observed that G-2-MePE improved dendritic arborization and increased dendritic spine length. FIG. 24 depicts results of this study. Dendritic length in μm (vertical axis) is plotted against the distance (in μm; horizontal axis) from the soma of the cells. For cells with dendrites close to the somas, the dendrites were short. However, as the distance from the somas increased saline-treatment (open squares) produced dendritic lengths that increased to a maximum at a distance of 70 μm from the soma and declined at distances further away from the somas. In contrast, treatment with G-2MePE (filled squares) produced longer dendrites over much of the range of distances from the somas.

Example 10

Treatment of Rett Syndrome in Mice II Mice Mating and Genotyping

The MeCP2 germline null allele mice are used (Chen et al., 2001). Genotyping is performed as in Chen et al. (Chen et al., 2001).

G-2-MePE Treatment

For the survival measurements, the nocturnal activity analysis and the immunoblot analysis, G-2-MePE (synthesised Albany Molecular Research Inc. (Albany, N.Y.) and supplied by Neuren Pharmaceuticals Limited) is administered daily via intra-peritoneal injections (20 mg/kg, vehicle=saline, 0.01% BSA). The treatment starts at PI 5 and is maintained throughout the course of the experiments. For intracellular physiology experiments, the mice are injected daily with G-2-MePE (20 mg/kg body weight, vehicle=saline, 0.01% BSA) for 2 weeks, from P15 to P28-P32 when they are used for acute slice preparation. For optical imaging experiments, mice are injected with G-2-MePE (20 mg/kg body weight, vehicle=saline, 0.01% BSA) daily from the day of the lid suture to the day of imaging.

Slice Physiology Preparation

Coronal sections (300 μm thick) at or near sensorimotor cortex are cut in <4° C. ACSF using a Vibratome. Slices are incubated at 37° C. for 20 minutes after slicing, and at room temperature for the remainder of the experiment. Slices are transferred to a Warner chamber and recordings are taken from visually identified pyramidal neurons located in layer 5. Artificial cerebral spinal fluid (ACSF) containing 126 mM NaCl, 25 mM NaHCO3, 1 mM NaHPO4, 3 mM KCl, 2 mM MgSO4, 2 mM CaCl2, and 14 mM dextrose, is adjusted to 315-320 mOsm and 7.4 pH, and bubbled with 95% O2/5% CO2. The intracellular pipette solution contained 100 mM potassium gluconate, 20 mM KCl, 10 mM HEPES, 4 mM MgATP, 0.3 mM NaGTP, and 10 mM Na-phosphocreatine.

Intracellular Whole-Cell Recordings

Borosilicate pipettes (3-5 MΩ, WP1) are pulled using a Sutter P-80 puller (Sutter Instruments). Cells are visualized with an Achroplan 40× water-immersion lens with infrared-DIC optics (Zeiss) and detected with an infrared camera (Hamamatsu) projecting to a video monitor. Experiments are driven by custom acquisition and real-time analysis software written in Matlab (Mathworks, Natick, Mass.) using a Multiclamp 700B amplifier (Axon Instruments) connected to a BNC-2110 connector block and M-Series dual-channel acquisition card (National Instruments). Gigaseal and rupture is achieved and whole-cell recordings are continuously verified for low levels of leak and series resistance. For each recording, a 5 mV test pulse is applied in voltage clamp ~10 times to measure input and series resistance. Then in current clamp ~10 pulses (500 ms, 40-140 pA at 10 pA increments), are applied to quantify evoked firing rates and cellular excitability. Access resistance, leak, and cellular intrinsic excitability are verified to be consistent across groups. Finally, spontaneous EPSCs under voltage clamp at −60 mV are sampled at 10 kHz and low-pass filtered at 1 kHz. Analysis is performed using a custom software package written in Matlab, with all events detected according to automated thresholds and blindly verified for each event individually by the experimenter.

Golgi Staining

Samples (<1 cm) from P28 mice are fixed in 10% formalin and 3% potassium bichromate for 24 hours. Tissue is then transferred into 2% silver nitrate for 2 days in the dark at room temperature. Sections from these samples are then cut at 50 μm thickness into distilled water. Sections corresponding to motor cortex are mounted onto slides, air dried for 10 minutes, and then dehydrated through sequential rinses of 95% alcohol, 100% alcohol, and xylene, and then sealed with a coverslip. Images re acquired at 10× (whole cell) and 100× (spine imaging) using a Zeiss Pascal 5 Exciter confocal microscope.

Optical Imaging of Intrinsic Signals

Adult (>P60) wild type (SVEV or BL6) and MeCP2 (+/−) mutant females (BL6) are used for this experiment. The wild type control group is composed of both wild type littermates of MeCP2+/− females or wild type age matched SVEV females. For monocular deprivation, animals are anesthetized with Avertin (0.016 ml/g) and the eyelids of one eye is sutured for 4 days. Prior to imaging, the suture is removed and the deprived eye re-opened. Only animals in which the deprivation sutures are intact and the condition of the deprived eye appears healthy are used for the imaging session. For G-2-MePE signaling activation, a solution containing G-2-MePE is injected intra-peritoneally (IP) daily for the entire period of deprivation. For the imaging sessions mice are anesthetized with urethane (1.5 g/kg; 20% of the full dosage is administered IP each 20-30 minutes up to the final dosage, 0.02 ml of cloroprothixene 1% is also injected together with the first administration). The skull is exposed and a custom-made plate is glued on the head to minimize movement. The skull is thinned over V1 with a dremel drill and covered with an agarose solution in saline (1.5%) and a glass coverslip. During the imaging session, the animal is constantly oxygenated, its temperature maintained with a heating blanket and the eyes periodically treated with silicone oil; physiological conditions are constantly monitored. The anesthetized mouse is placed in front of a monitor displaying a periodic stimulus presented to either eye, monocularly; the stimulus consisted of a drifting vertical or horizontal white bar of dimensions 9°×72°, drifting at 9 sec/cycle, over a uniformly gray background. The skull surface is illuminated with a red light (630 nm) and the change of luminance is captured by a CCD camera (Cascade 512B, Roper Scientific) at the rate of 15 frames/sec during each stimulus session of 25 minutes. A temporal high pass filter (135 frames) is employed to remove the slow signal noise, after which the signal is computer processed in order to extract, at each pixel, the temporal Fast Fourier Transform (FFT) component corresponding to the stimulus frequency. The FFT amplitude is used to measure the strength of the visual evoked response to each eye. The ocular dominance index is derived from each eye's response (R) at each pixel as ODI=(Rcontra−Ripsi)/(Rcontra+Ripsi). The binocular zone is defined as the region activated by the stimulation of the eye ipsilateral to the imaged hemisphere.

Heart Rate Measurements

Real time cardiac pulse rate is measured using a tail clip sensor (Mouse OX Oximeter—Oakmont, Pa.). Mice are not anesthetized but physically restrained in a fitted open plastic tube. Prior to the recording session the tube is placed overnight in the cages housing the experimental animals to allow habituation. Body temperature is maintained at ~82-84° F.

throughout the recording time. We record 3 trials of 15 minutes for each mouse, mice are 8 weeks old and treated with vehicle or G-2-MePE from P15.

Nocturnal Activity Measurements

Spontaneous motor activity is measured by using an infrared beam-activated movement-monitoring chamber (Opto-Varimax-MiniA; Columbus Instruments, Columbus, Ohio). For each experiment, a mouse is placed in the chamber at least 3 h before recordings started. Movement is monitored during the normal 12-h dark cycle (7 p.m. to 7 a.m.). One dark cycle per animal per time point is collected.

Results

To test whether G-2-MePE treatment will impact the development of cardinal features of the RTT disease, 2 week old mutant animals are given daily intra-peritoneal injections for the course of their lifespan. Measurements of synaptic physiology, synaptic molecular composition, and cortical plasticity are then acquired as detailed below, along with health-related measurements such as heart rate, locomotor activity levels, and lifespan.

Effects of G-2-MePE on the Synaptic Physiology of MeCP2 Mutant Mice

Recent studies have reported that neurons across multiple brain regions of MeCP2–/y mice display a profound reduction in spontaneous activity (Chang et al., 2006; Chao et al., 2007; Dani et al., 2005; Nelson et al., 2006) a phenotype that is rescued by over-expression of BDNF (Chang et al., 2006). Similarly, acute application of an IGF1 derivative has been shown to elevate evoked excitatory postsynaptic current (EPSC) amplitudes by 40% in rat hippocampal cultures (Ramsey et al., 2005; Xing et al., 2007). To test the efficacy of G-2-MePE in rescuing the MeCP2–/y physiological phenotype, we acquire intracellular whole cell recordings in acute brain slices, measuring excitatory synaptic drive (spontaneous EPSC amplitude and frequency) in layer 5 cortical neurons. Here, EPSCs recorded from –/y animals are significantly reduced in amplitude compared to EPSCs measured in wild-type animals. The trend is partially reversed in EPSCs recorded from MeCP2–/y animals treated with G-2-MePE, which are significantly larger in amplitude than EPSCs from MeCP2–/y mice treated with vehicle. These differences are also seen when averaging across cells. Throughout these measurements, access resistance, leak, and cellular intrinsic excitability are also verified to be consistent across groups. Quantifying EPSC intervals also shows a slight increase in the interval between EPSC events (reduced EPSC frequency) between wild-type and MeCP2–/y animals (P=0.04, Kolmogorov-Smirnov test). Our findings thus indicate that the reduction of excitatory synaptic drive in cortical cells of MeCP2–/y mice, and its partial rescue following G-2-MePE treatment, are due in part to a change in EPSC amplitude as a consequence of a change in the strength of the synapses mediating excitatory transmission in this region.

G-2-MePE Treatment Stimulates Cortical Spine Maturation

We use Golgi staining to label neurons sparsely and distinctly, and applied high-resolution confocal imaging to measure dendritic spine density and morphology in the labelled cells, restricting analysis to layer 5 pyramidal neurons in sections of motor cortex from critical period mice (P28).

While low-magnification imaging clearly delineates the extent of the dendrites of the pyramidal cells we use higher magnifications to count synaptic contacts and determine the morphological class of each spine. We classify spines as either large and bulbous ("mushroom", M), short and stubby ("stubby", S), short and thin ("thin", T) or filopodia (F). Comparing the density of spines per unit branch exhibits a trend of decreased spine density in knockout neurons that is largely ameliorated in the knockout with treatment.

Together these results indicate the potential for deficits in the number and maturational status of dendritic contacts in the knockout to underpin functional defects in excitatory transmission, in a manner that can be treated following administration of G-2-MePE.

Ocular Dominance (OD) Plasticity in Adult MeCP2+/– Mice is Reduced by G-2-MePE

Developmental changes in OD plasticity are controlled in part by the activation of the IGF-1 pathway, and administration of (1-3)IGF-1 can reduce OD plasticity in wild type young mice (Tropea et al., 2006). We therefore test if G-2-MePE treatment could stabilize the prolonged OD plasticity observed in adult MeCP2 mutants. Female MeCP2+/– mice, aged P60 or more, are monocularly deprived for 4 days and treated concurrently with G-2-MePE. G-2-MePE treatment reduces the OD plasticity in the adult Mecp2+/– mice, indicating that indeed G-2-MePE can rapidly induce synapse stabilization or maturation.

Bradycardia in MeCP2–/y Mice is Treated by G-2-MePE

In addition to examining the efficacy of G-2-MePE in ameliorating neurophysiological symptoms, we seek to characterize its effects on the general health of the organism. Clinical and experimental evidence shows autonomic system dysfunctions such as labile breathing rhythms and reduced baseline cardiac vagal tone in Rett Syndrome patients (Julu et al., 2001). A poor control of the feedback mechanisms that regulate blood pressure homeostasis through the sympathetic system, for example hyperventilation-induced decrease in heart rate, is common in Rett Syndrome patients and can cause life threatening cardiac arrhythmias (Acampa and Guideri, 2006; Julu et al., 2001).

The pathogenesis of the cardiac dysautonomia, although not well understood, suggests that immature neuronal connections in the brainstem could be the cause. To examine heart rate abnormalities in MeCP2–/y mice and the effect of G-2-MePE treatment, we monitor real time cardiac pulse rate in non-anesthetized wild type and MeCP2–/y animals treated with vehicle or G-2-MePE. Wild type mice exhibit a regular distribution of heart rate measurements centred near 750 beats per minute. In contrast, MeCP2–/y mice exhibit a more irregular heart rate with a lower average rate, the occurrence of which is significantly reduced following treatment with G-2-MePE.

G-2-MePE Administration Improves Locomotor Activity and Life Span

MeCP2–/y mice develop Rett-like symptoms beginning at 4-6 weeks of age when they progressively become lethargic, develop gait ataxia and die between 10 and 12 weeks of age (Chen et al., 2001). Baseline locomotor activity is also recorded in mice after 6 weeks by counting nocturnal infrared beam crossing events within a caged area. MeCP2 knockout mice (KO) exhibits markedly reduced locomotor activity levels compared to wild-type mice (WT), but treatment with G-2-MePE (KO-T) elevates these levels.

Finally, compared to MeCP2 KO littermates, MeCP2–/y mice treated with G-2-MePE also show a ~50% increase in life expectancy (an increase in the 0.5 probability survival rate).

We also measure the effect of G-2-MePE treatment on neuron soma size in the hippocampus. Mice are treated with G-2-MePE as described above for locomotor activity. Soma size in neurons in the CA3 region of the hippocampus is significantly impaired in MeCP2 KO animals relative to wild-type animals. G-2-MePE treatment increases average soma size in KO animals, but has little or no effect on soma size in wild type animals.

Example 11

Effect of Oral G-2-MePE on Survival in Rett Syndrome in Mice

Because Rett Syndrome is a chronic, debilitating disorder involving loss of motor skills, it is desirable to treat Rett Syndrome using easily administered preparations. To this end, we can take advantage of unexpectedly beneficial therapeutic and pharmacokinetic properties of G-2-MePE and related compounds (U.S. Pat. Nos. 7,041,314, 7,605,177, 7,714,070, 7,863,309 and U.S. application Ser. Nos. 11/315,784 and 12/903,844).

Therefore, we administer G-2-MePE orally to MeCP2 deficient mice as described in US 2009/0074865. Briefly, an aqueous solution, a water-in-oil emulsion (micro-emulsion, coarse emulsion or liquid crystal), or a gel composition containing a pharmaceutically effective amount of G-2-MePE (20 or 80 mg/kg per animal) is administered daily. In control MeCP2 deficient animals, we administer saline only, and wild-type animals are used to obtain baseline data similar to the design of studies described in Example 8 above.

In wild-type animals, survival is defined to be 100% at each time point. In MeCP2 deficient animals, survival is decreased substantially. However, after oral administration of G-2-MePE to MeCP2 deficient mice, survival is increased substantially.

Example 12

Effect of G-2MePE on Seizure Activity in Rett Syndrome in Mice

Because seizures are a prominent, hazardous and a difficult to treat aspect of Rett Syndrome, we determine the effects of G-2MePE on seizure activity in MeCP2 deficient animals. G-2-MePE can be effective in treating seizure activity in animals with neurodegenerative disease (U.S. Pat. No. 7,714,020). Therefore, we carry out experiments to determine whether G-2-MePE can also treat seizure activity in MeCP2 deficient mice.

Electroencephalograpic recordings of wild-type mice and MeCP2 deficient mice treated with either saline or G-2-MePE are obtained using methods described in U.S. Pat. No. 7,714,020.

We find that G-2MePE can be effective in decreasing both motor seizures and non-convulsive seizures.

Conclusions

Based on our in vivo and in vitro studies in MeCP2 deficient animals, we conclude that G-2-MePE can be an effective therapy for treating human beings with Rett Syndrome. Moreover, because G-2-MePE has unexpectedly longer half life than a naturally occurring compound ((1-3) IGF-1; Glycyl-Prolyl-Glutamate or GPE) (FIG. 21), we conclude that use of G-2-MePE has distinct and substantial advantages over other pharmacological agents, including GPE.

For example, G-2-MePE is not degraded by gastrointestinal cells, is taken up by gastrointestinal cells, and is active in the central nervous system after oral administration (Wen et al., U.S. application Ser. No. 12/283,684; U.S. 2009/0074865, U.S. Pat. No. 7,887,839, incorporated herein fully by reference), Therefore, G-2MePE need not be delivered intravenously, subcutaneously, intraventricularly, or parenterally. In fact, oral formulations comprising microemulsions, coarse emulsions, liquid crystal preparations, nanocapsules and hydrogels can be used in manufacture of orally administered preparations such as tablets, capsules and gels that can improve neurological function and treat neurodegenerative conditions (U.S. Pat. No. 7,887,839). Compounds of this invention can be used in situations in which a patient's motor functioning is below that needed to swallow a table or capsule. There are several types of soluble gels for oral administration of compounds, and these can be used to deliver a compound or composition of this invention to a patient. Because G-2-MePE can be easily administered orally and is orally effective in treating neurodegenerative disorders, including Rett Syndrome, we conclude that G-2-MePE can be convenient and beneficial for long-term therapy of patients with Rett Syndrome.

Further, because Rett Syndrome shares key features with other autism spectrum disorders, compounds of this invention can be useful in providing therapeutic benefit from animals having other ASD, and in humans with autism, Asperger Syndrome, Childhood Disintegrative Disorder, and Pervasive Developmental Disorder—Not Otherwise Specified (PDD-NOS).

Example 13

Treatment of ASD

Shank3-Deficient Mouse Model

Shank3-deficient mice are used in the study as a model of 22q13 deletion syndrome associated with ASD.

22q13 deletion syndrome has been linked with deletions or mutations in Shank3 gene (Bonaglia et al, 2006). The Shank3 gene codes for a master scaffolding protein which forms the framework in glutamatergic synapses (Boeckers et. al, 2006). Shank3 is a crucial part of the core of the postsynaptic density (PSD) and recruits many key functional elements to the PSD and to the synapse, including components of the α-amino-3-hydroxyl-5-methyl-4-isoxazole-propionic acid (AMPA); metabotropic glutamate (mGlu), and N-methyl-D-aspartic acid (NMDA) glutamate receptors, as well as cytoskeletal elements. Recent studies exploring the rate of 22q13 deletions/Shank3 mutations suggest that haploinsufficiency of Shank3 can cause a monogenic form of ASD with a frequency of 0.5% to 1% of ASD cases (Durand et al, 2007; Moessner et al, 2007; Gauthier et al, 2008).

The generation of the mouse model with disrupted expression of full-length Shank3 has been previously described in the art (Bozdagi et al., Molecular Autism 2010, 1:15, p 4). Briefly, Bruce4 C57BL/6 embryonic stem cells were used to generate a mouse line that had loxP sites inserted before exon 4 and exon 9. The floxed allele was excised and a line was maintained with a deletion of exons 4 to 9, i.e. a complete deletion of the ankyrin repeat domains of Shank3. Wild-type (+/+), heterozygous (+/−) and knockout (−/−) mice were produced, with Mendelian frequencies from heterozygote-heterozygote crosses. A 50% reduction of full length Shank3 mRNA was confirmed in heterozygotes (qPCR) as well as a reduced expression of Shank3 protein (by immunoblotting with Shank3 antibody N69/46).

Heterozygous mice generated by crossing wild-type mice with heterozygotes are used in this example to best model the haploinsufficiency of Shank3, responsible for 22q13 deletion syndrome.

Methods

Drug Treatment 1 to 3 month old wild type and heterozygous Shank3-deficient mice are divided into 4 treatment groups: placebo treated wild-type, placebo treated Shank3-deficient group and two Shank3-deficient G-2-MePE treated groups. The animals are given placebo (water) or G-2-MePE formulated in water administered orally, b.i.d for 14 days. G-2-MePE is administered at two doses: 15 or 60 mg/kg.

Methodology

A detailed description of the methodology can be found in Bozdagi et al. (Molecular Autism 2010, 1:15).

Behavioral Analyses

Behavioral assessments are made at several, time points, and include analysis of social interactions and ultrasonic social communication, in line with the methodology described by Bozdagi et al. Briefly, male-female social interactions in each treatment group are evaluated. The subject males are group-housed and individually tested in clean cages with clean litter. Each testing session lasts 5 min. Each of the subject mice is paired with a different unfamiliar estrus C57BL/6J female. A digital closed circuit television camera (Panasonic, Secaucus, N.J., USA) is positioned horizontally 30 cm from the cage. An ultrasonic microphone (Avisoft UltraSoundGate condenser microphone capsule CM15; Avisoft Bioacoustics, Berlin, Germany) is mounted 20 cm above the cage. Sampling frequency for the microphone is 250 kHz, and the resolution is 16 bits. While the equipment used cannot distinguish between calls emitted by the male subject and female partner, the preponderance of calls during male-female interactions in mice is usually emitted by the male. The entire apparatus is contained in a sound-attenuating environmental chamber (ENV-018V; Med Associates, St Albans, Vt., USA) illuminated by a single 25-Watt red light. Videos from the male subjects are subsequently scored by an investigator uninformed of the subject's genotype and treatment group on measures of nose-to-nose sniffing, nose-to-anogenital sniffing and sniffing of other body regions, using Noldus Observer software (Noldus Information Technology, Leesburg, Va., USA). Ultrasonic vocalizations are identified manually by two highly trained investigators blinded to genotype/treatment group information, and summary statistics are calculated using the Avisoft package. Interrater reliability is 95%. Data are analysed using an unpaired Student's t-test.

Olfactory habituation/dishabituation testing is conducted in male and female mice for each group. The methodology is as previously described (Silverman et al 2010, Yang et al 2009 and Silverman et al 2010). Non-social and social odors are presented on a series of cotton swabs inserted into the home cage sequentially, each for 2 min, in the following order: water, water, water (distilled water); almond, almond, almond (1:100 dilution almond extract); banana, banana, banana (1:100 dilution artificial banana flavouring); social 1, social 1, social 1 (swiped from the bottom of a cage housing unfamiliar sex-matched B6 mice); and social 2, social 2, social 2 (swiped from the bottom of a second cage housing a different group of unfamiliar sex-matched 129/SvImJ mice). One-way repeated measures ANOVA is performed within each treatment group for each set of habituation events and each dishabituation event, followed by a Tukey post hoc test.

Hippocampal Slice Electrophysiology

Post-mortem, acute hippocampal slices (350 μm) are prepared from mice using a tissue chopper. Slices are maintained and experiments are conducted at 32° C. Slices are perfused with Ringer's solution containing (in mM): NaCl, 125.0; KCl, 2.5; $MgSO_4$, 1.3; $NaH_2PO_4$, 1.0; $NaHCO_3$, 26.2; $CaCl_2$, 2.5; glucose, 11.0. The Ringer's solution is bubbled with 95% $O_2$/5% $CO_2$, at 32° C., during extracellular recordings (electrode solution: 3 M NaCl). Slices are maintained for 1 hr prior to establishment of a baseline of field excitatory postsynaptic potentials (fEPSPs) recorded from stratum radiatum in area CA1, evoked by stimulation of the Schaffer collateral-commissural afferents (100 μs pulses every 30 s) with bipolar tungsten electrodes placed into area CA3. Test stimulus intensity is adjusted to obtain fEPSPs with amplitudes that are one-half of the maximal response. The EPSP initial slope (mV/ms) is determined from the average waveform of four consecutive responses. Input-output (I/O) curves are generated by plotting the fEPSP slope versus fiber volley amplitude in low-$Mg^{2+}$ (0.1 mM) solution. AMPA receptor-mediated and NMDA receptor-mediated I/O relationships are measured in the presence of ionotropic glutamate receptor antagonists: 2-amino-2-phosphonopentanoic acid APV (50 μM) and 6-cyano-7-nitroquinoxaline-2,3-dione CNQX (100 μM). Paired-pulse responses are measured with interstimulus intervals of 10 to 200 ms, and are expressed as the ratio of the average responses to the second stimulation pulse to the first stimulation pulse.

LTP is induced either by a high-frequency stimulus (four trains of 100 Hz, 1 s stimulation separated by 5 min), or by theta-burst stimulation (TBS) (10 bursts of four pulses at 100 Hz separated by 200 ms), or by a single 100 Hz stimulation, for control and genetically-modified mice. To induce long-term depression (LTD), Schaffer collaterals are stimulated by a low frequency or paired-pulse low frequency stimulus (900 pulses at 1 Hz for 15 min) to induce mGlu receptor-dependent LTD. Data are expressed as means±SD, and statistical analyses are performed using analysis of variance (ANOVA) or student's t-test, with significance set at an a level of 0.05.

Results

Behavioral

Cumulative duration of total social sniffing by the male test subjects is lower in placebo treated Shank3-deficient group than in placebo treated wild-type group. In addition, fewer ultrasonic vocalizations are emitted by the placebo treated Shank3-deficient group than by the wild-type controls during the male-female social interactions.

G-2-MePE treatment in the two Shank3-deficient groups results in a significant increase in the cumulative duration of total social sniffing in comparison to the placebo treated Shank3-deficient group. Moreover, the G-2-MePE treated groups display an increased number of ultrasonic vocalizations than the placebo treated mutant group.

In the olfactory habituation/dishabituation study, intended to confirm that the mice are able to detect social pheromones, all 4 groups display normal levels of habituation (indicated by decreased time spent in sniffing the sequence of three same odors), and the expected dishabituation (indicated by increased spent in sniffing the different odor).

Electrophysiology

Plotting field excitatory postsynaptic potential (fEPSP) slope versus stimulus intensity demonstrates a reduction in the I/O curves in the placebo treated Shank3-deficient group versus the control group. In the heterozygous placebo treated group we also observe a decrease in AMPA receptor-mediated field potentials, reflected in a 50% decrease in the average slope of I/O function compared to the wild-type control group. In contrast, when the I/O relationship is analysed in the presence of the competitive AMPA/kainate receptor antagonist CNQX to measure synaptic NMDA receptor function, there is no difference between the wild-type and placebo treated heterozygous groups. These results indicate that there is a specific reduction in AMPA receptor-mediated basal transmission in the Shank3 heterozygous mice.

G-2-MePE treatment in both heterozygous groups normalizes the AMPA receptor-mediated field potentials and causes an increase in the average slope of I/O function compared to the placebo treated Shank3-deficient group.

The maintenance of LTP in the placebo treated Shank3-deficient group is clearly impaired in comparison to the wild-type control. TBS LTP tests (10 bursts of four pulses at 100 Hz separated by 200 ms) also show a significant decrease in the potentiation at 60 min after TBS in the placebo treated Shank3-deficient group. In contrast to the altered synaptic plasticity observed with LTP, long-term depression (LTD) was not significantly changed in the mutant group. G-2-MePE treatment increased hippocampal long-term potentiation (LTP) and its maintenance in both Shank3-deficient group in comparison to the placebo treated Shank3-deficient group.

Discussion

Poor social competencies and repetitive behaviors are the common features and key diagnostic measures of all forms of ASD, Delayed intellectual development and underdeveloped language skills are also a common feature present in all ASD, excluding Asperger syndrome.

The animal models described above have been accepted in the art as demonstrating similar symptoms to the clinical human conditions. All mutant models discussed above (NLGN3, NLGN4, CADM1, NRXN1, FMR1, shank3) exhibit impaired social skills or increased social anxiety. Decreased excitatory transmission into the hippocampus has been identified in NRXN1, shank3, MeCP2 and FMR1 mutant animal models. At present no polygenetic or multifactorial models of ASD have been described. The animal models described above, based on genetic defects that are known to produce ASD in human population, provide the best opportunity to test the efficacy of ASD therapies.

Therefore the efficacy of G-2-MePE in animal models of ASD is reasonably predictive of its efficacy in a human subject suffering from ASD.

Example 14

G-2-MePE Treatment Changes the Morphology of Neurons in an In Vitro Human Model of Rett Syndrome To test the effects of G-2-MePE on neuronal morphology, we used an in vitro model of RTT described in Marchetto et al., *A model for neural development and treatment of Rett syndrome using human induced pluripotent stem cells*, Cell 143:527-539 (2010) (including supplemental information). The model uses induced pluripotent stem cells (iPSCs) generated from fibroblasts of human RTT patients carrying different MeCP2 mutations.

Methods

Cell Culture and Retrovirus Infection

RTT fibroblasts (carrying 4 distinct MeCP2 mutations) and control fibroblasts are generated from explants of dermal biopsies. The shRNA against target MeCP2 gene is cloned into the LentiLox3.7 lentivirus vector (as described in Marchetto et al.). The fibroblasts are infected with retroviral reprogramming vectors (Sox2, Oct4, c-Myc and Klf4), Two days after infection, fibroblasts are plated on mitotically inactivated mouse embryonic fibroblasts with hESC medium. After 2 weeks, iPSC colonies that emerge from the background of fibroblasts are manually picked and transferred to feeder-free conditions on matrigel-coated dishes (BD) using embryonic stem cell culture media mTeSR™ (Stem Cell Technologies) and passaged manually. Gene expression profiles of the generated clones are measured using human genome Affymetrix Gene Chip™ arrays to confirm that reprogramming is successful.

Neural Differentiation: NPCs and Mature Neurons

To obtain neural progenitor cells (NPCs), embryoid bodies (EBs) are formed by mechanical dissociation of cell clusters and plating onto low-adherence dishes in hESC medium without FGF2 for 5-7 days. After that, EBs are plated onto poly-ornithine/laminin-coated dishes in DMEM/F12 plus N2 medium (serum-free supplement for growth and expression of post-mitotic cells). Resulting rosettes are collected after 7 days and dissociated with accutase and plated onto coated dishes with NPC media (DMEM/F12; 0.5×N2; 0.5×B27 and FGF2). Homogeneous populations of NPCs are achieved after 1-2 passages with accutase in the same condition. To obtain mature neurons, floating EBs are treated with 1 uM or retinoic acid for 3 weeks (giving the total time of differentiation of 4 weeks). Mature EBs are dissociated with papain and DNAse for 1 h at 37° C. and plated in poly-ornithine/laminin-coated dishes in NPC media without FGF2.

Treatment with G-2-MePE

RTT neuronal cultures are treated with G-2-MePE (1 nM-10M) for 1 week,

Immunocytochemistry and Quantification of Neuronal Morphology

Cells are fixed in 4% paraformaldehyde and permeabilized with 0.5% Triton-X100 in PBS. Cells are then blocked in PBS containing 0.5% Triton-X100 and 5% donkey serum for 1 h at room temperature. Fluorescent signals are detected using a Zeiss inverted microscope and images are processed with Photoshop CS3. The following primary antibodies are used: TRA-1-60, TRA-1-81 (1:100), Nanog and Lin28 (1:500), human Nestin (1:100), Tuj-1 (1:500), Map2 (1:100); meCP2 (1:1000; VGLUT1 (1:200), Psd95 (1:500), GFP (1:200), Sox1 (1:250), Mushasil (1:200) and me3H3K27 (1:500). Cell soma size is measured using suitable software (e.g. ImageJ) after identification of neurons using the Syn::EGFP™. The morphologies of neuronal dendrites and spines are studied from an individual projection of z-stacks optical sections and scanned at 0.5 um increments that correlate with the resolution valued at z-plane. Each optical section is the result of 3 scans at 500 lps followed by Kalman filtering. For synapse quantification, images are taken by a z-step of 1 um using Biorad radiance 2100™ confocal microscope. Synapse quantification is done blinded to genotype. Only VGLUT1 puncta along Map2-positive processes are counted. Statistical significance is tested using 2-way ANOVA test and Bonferroni post-test.

Calcium Imaging

Neuronal networks derived from human iPSCs are infected with the lentiviral vector carrying the Syn:DsRed reporter construct. Cell cultures are washed twice with sterile Krebs HEPES Buffer (KHB) and incubated with 2-5 μM Fluo-4AM™ (Molecular Probes/Invitrogen, Carlsbad, Calif.) in KHB for 40 minutes at room temperature. Excess dye is removed by washing twice with KHB, and an additional 20 minutes incubation is done to equilibrate intracellular dye concentration and allow de-esterification. Time-lapse image sequences (100× magnification) of 5000 frames are acquired at 28 Hz with a region of 336×256 pixels, using a Hamamatsu ORCA-ER™ digital camera (Hamamatsu Photonics K.K., Japan) with a 488 nm (FITC) filter on an Olympus IX81 inverted fluorescence confocal microscope (Olympus Optical, Japan). Images are acquired with MetaMorph 7.7™ (MDS Analytical Technologies, Sunnyvale, Calif.). Images are subsequently processed using ImageJ™ and custom written routines in Matlab 7.2™ (Mathworks, Natick, Mass.).

Electrophysiology

Whole-cell patch clamp recordings are performed from cells co-cultured with astrocytes after 6 weeks of differentiation. The bath is constantly perfused with fresh HEPES-buffered saline (see supplemental methods for recipe). The recording micropipettes (tip resistance 3-6 MSG) are filled with internal solution described in the Supplemental materials. Recordings are made using Axopatch 200B™ amplifier (Axon Instruments). Signals are filtered at 2 kHz and sampled at 5 kHz. The whole-cell capacitance is fully compensated. The series resistance is uncompensated but monitored during the experiment by the amplitude of the capacitive current in response to a 10-mV pulse. All recordings are performed at room temperature and chemicals are purchased from Sigma. Frequency and amplitude of spontaneous postsynaptic currents are measured with the Mini Analysis Program™ software (Synaptosoft, Leonia, N.J.). Statistical comparisons of WT and RTT groups are made using the non-parametric Kolmogorov-Smirnov two-tailed test, with a significance criterion of $p=0.05$. EPSCs are blocked by CNQX or DNQX (10-20 µM) and IPSPs are inhibited by bicuculine (20 µM).

Results

RTT iPSC-derived neurons are characterized by decreased number of glutamatergic synapses, reduced spine density and smaller soma size. RTT neurons also show certain electophysiological defects, i.e. a significant decrease in frequency and amplitude of spontaneous synaptic currents when compared to controls. The RTT neurons show a decreased frequency of intracellular calcium transients.

We test G-2-MePE in the above model to test whether any of the pathologies of the RTT phenotype can be attenuated.

Treatment of the cell cultures with each drug concentration improves all of the morphological and physiological parameters of the treated RTT cell cultures in comparison to the non-treated RTT controls. Specifically, we observe a significant increase in glutamatergic synapse numbers in the G-2-MePE treated RTT cells. All concentrations of G-2-MePE treatment increase VGLUT1 puncta number in the RTT-derived neurons. G-2-MePE treatment normalizes the frequency and amplitude of spontaneous post-synaptic currents as well as the frequency of calcium transients generated by synaptic activity of the G-2-MePE treated RTT neurons.

In the present in vitro model of human RTT, the iPSCs derived from RTT patients and neurons differentiated from them are characterized by abnormalities in the MeCP2 expression. As discussed in the detailed description of the invention above, the vast majority of RTT cases are associated with mutations of the MeCP2 gene. Therefore the efficacy of G-2-MePE in the present in vitro model of human RTT is reasonably predictive of its efficacy in a human subject suffering from RTT.

Example 15

Effects of G-2-MePE in Human Beings with Rett Syndrome

Methods

Thirty subjects with Rett Syndrome are recruited, Subjects are female and aged between 16 and 29 years (Mean=12.1 SD=4.4). All subjects have an IQ<60 and mutations of the MECP2 gene. Subjects also show ether spike activity in the EEG or an increase in lower frequency bands of the BEG as detected by Fast Fourier Transform (FFT). Subjects are instructed that concomitant medications are to be stable for at least six weeks prior to study. Subjects receiving medication to treat signs of inattention are tested in the morning and instructed to take their medication in the afternoon. Subjects with QTc interval >451 msec are excluded.

The study is a randomized double blind placebo controlled parallel study with three doses of either placebo, 10 mg/kg T.I.D oral G-2-MePE for five days, or 30 mg/kg T.I.D. oral G-2-MePE.

Subjects are tested at baseline using the following instruments: The Rett Syndrome Natural History/Clinical Severity Scale, Aberrant Behavior Checklist Community Edition (ABC), Vinelands, Clinical Global Impression of Severity (CGI-S) and their carers completed the Caregiver Strain Questionnaire (CSQ).

Subjects are brought into clinic on an inpatient basis to enable initial baseline recordings of EEG, ECG and respiratory rate continuously for 24 hours using polysomnography technology. Hand movements are also recorded using the Q-Sensor™. Derived EEG measures include: spikes per unit time in the EEG, overall power of frequency bands of the EEG, QTc and heart rate variability (HRV), and respiratory irregularities.

Adverse events are also recorded using standard safety measures and the SMURF elicitation of adverse events Statistically, the effect of treatment with G-2-MePE is analysed by conducting a repeated analysis of covariance (ANCOVA) on the effect of treatment on change from baseline scores.

Results

Treatment with G-2-MePE produces no more adverse events than are present during treatment with placebo, with all adverse events being of short duration and mild severity. No Serious Adverse Events are reported. No instances of increases in QTC are reported.

No effects are seen on respiratory rate or heart rate variability.

Treatment with G-2-MePE produces a significant overall reduction of spikes per unit time in the EEG. Treatment with 30 mg/kg T.I.D. oral G-2-MePE decreases spike activity compared to placebo. This dose of G-2-MePE also decreases the power of the delta band of the EEG compared to placebo.

Treatment with G-2-MePE also reduces total hand movements per twenty-four hour period as counted using the Q-Sensor™ device. This effect is significant for the 30 mg/kg T.I.D. dose compared to placebo.

Treatment with G-2-MePE has no significant effect overall on the Rett Syndrome Natural History/Clinical Severity Score. However, 30 mg/kg T.I.D. oral G-2-MePE, compared to placebo, produces significant effects on the following subscales: "Nonverbal Communication at this visit by exam"; "Epilepsy/Seizures at this visit: and "Hand use".

Conclusions

Treatment with G-2-MePE produces significant improvements in Central Nervous System function in the present study. Despite relatively short term treatment, abnormalities in the electrical activity of the brain is reduced, a clear signal of efficacy. This effect is dose dependent, seen after treatment 30 mg/kg T.I.D. oral G-2-MePE, These effects mirror the improvements in CNS function seen in the mecp2 knockout transgenic mouse model of Rett Syndrome after administration of G-2-MePE.

Dose dependent effects are also seen on hand use, as assessed by an objective counting device and subjective rating. This is of interest because purposeless hand wringing is both characteristic to the Rett Syndrome clinical phenotype and is unique to this disorder.

The Non-verbal communication rating of the Rett Syndrome Natural History/Clinical Severity Scale is improved by treatment. This measure primarily assesses eye contact. This raises the prospect that longer term treatment with G-2-MePE may improve social relatedness in the population.

G-2-MePE is well tolerated in this population. No effects are seen in either standard measures or areas of specific concern in the patient population, such as QTc interval prolongation or apnea.

Example 16

Effects of G-2MePE on Human Beings with Autism Spectrum Disorders

Methods

To determine whether G-2-MePE can treat symptoms of ASD, we carry out a study in human beings with ASD. Twenty subjects with an Autism Spectrum Disorder are recruited. Subjects are male and aged between 16 and 65 years (Mean=18.1 SD=3.4). All subjects have an IQ >60 and strict DSM-IV-TR diagnosis of Autistic Disorder or Asperger Disorder, Subjects also meet criteria for an Autism Spectrum Disorder according the ADI-R and ADOS-G instruments, and fulfill the proposed DSM-V criteria for and Autism Spectrum Disorder. Subjects are instructed that concomitant medications are to be stable for at least six weeks prior to study. Subjects receiving medication to treat signs of inattention are tested in the morning and instructed to take their medication in the afternoon. Subjects better treated with atypical antipsychotic medications indicated for autism are excluded. Subjects are screened for known genetic disorders including and those with Fragile X Syndrome or tuberous sclerosis excluded. Subjects with uncontrolled epilepsy are excluded.

The study is a double blind placebo-controlled crossover study with three phases. Subjects enter each phase of the crossover in a randomized order. In the test phases, subjects receive either placebo, 10 mg/kg T.I.D oral G-2-MePE for five days, or 30 mg/kg T.I.D. oral G-2-MePE. Each phase of the crossover is separated by a washout period of fourteen days.

Subjects are tested at baseline using the following instruments: Wechsler IQ, Abberant Behavior Checklist Community Edition (ABC), Vinelands, Yale-Brown Obsessive Compulsive Scale (YBOCS) compulsion subscale, Social Responsiveness Scale (SRS), Clinical Global Impression of Severity (CGI-S) and their carers complete the Caregiver Strain Questionnaire (CSQ).

Subjects are administered two tasks—the Reading the Mind in the Eyes Test—Revised (RMET) and an Eye Tracking (ET) task, as well as Clinical Global Impression of Improvement (CGI-1). Tasks commence two hours following administration of placebo or either dose of G-2-MePE. The RMET is a computer based task that assesses one's ability to read emotions from the eyes of subtle affective facial expressions and is a widely used test of emotion recognition in patients with autism (2001). Importantly, the RMET is capable of detecting improvement with even a single dose of a pharmacological agent (Guastella et al., 2010). Eye tracking issues are characteristic of patients with autism who spend less time looking at the eyes of photographs of human faces. Again, a single administration of a pharmacologic intervention can ameliorate eye tracking deficits in autism (Andari et al, 2010).

Adverse events are also recorded using standard safety measures.

Statistically, the effect of treatment with G-2-MePE is analysed by conducting a repeated analysis of covariance (ANCOVA) on the effect of treatment on change from baseline scores.

Results

Treatment with G-2-MePE produces no more adverse events than were present during treatment with placebo, with all adverse events being of short duration and mild severity. No Serious Adverse Events are reported.

Treatment with G-2-MePE produces a significant overall improvement in performance of the RMET test. Treatment with 30 mg/kg T.I.D. oral G-2-MePE increases the percent correct responses on the RMET.

Treatment with G-2-MePE produces a significant overall improvement in time spent looking at the eye region in the ET test. CGI-1 scores at the end of treatment periods show a significant difference. Positive treatment effects are correlated with baseline CSQ scores.

Conclusions

Treatment with G-2-MePE produces significant improvements in performance in the Reading the Mind in the Eyes Test—Revised, and in performance of an Eye Tracking task. This effect is dose dependent, seen after treatment 30 mg/kg T.I.D. oral G-2-MePE.

Improvement in these measures is reflective of an improvement in processing of social information processing. Social interaction deficits are a core symptom diagnostic for autism spectrum disorders, and this is therefore a key finding.

G-2-MePE also produces an overall improvement in function as indexed by the Clinical Global Impression of Improvement. Free text annotation of the Case Report Forms from the study indicate this effect related to an improvement in social relatedness. This implies that the changes seen in the RMET and ET task may have relevance to social activity in daily life.

G-2-MePE is well tolerated in this population.

Example 17

Animal Models for Determining Effects of G-2-MePE on Autism Spectrum Disorders

Effects of G-2-MePE are further tested in the following genetic models of ASD: the Tbx1 heterozygous mouse, the Cntnap2 knockout mouse and the Sic9a6 knockout mouse. G-2-MePE is also tested in the fmr1 knockout mouse model of Fragile X Syndrome.

Tbx1.

Mutations of the TBX1 gene are associated with Autism Spectrum Disorders (Paylor et al., 2006). Transgenic Tbx1 mice are selectively impaired in social interaction, ultrasonic vocalization, repetitive behaviors and working memory (Hiramoto et al., 2011).

Cntnap2.

Two-thirds of patients with mutations of the contactin associated protein-like 2 (CNTNAP2) gene are diagnosed with an Autism Spectrum Disorder (Alarcon et al., 2008; Arking et al., 2008; Bakkaloglu et al., 2008; Strauss et al., 2006; Vernes et al., 2008). Cntnap2 knockout (KO) mice exhibit ASD-related phenotypes in social behavior, ultrasonic vocalization and repetitive behaviors (Penagarikano et al., 2011).

Slc9a6.

This gene has been implicated in syndromic ASD and encodes the sodim-hydrigen exchanger 6 (NHE6). Mutations in SLC9A6 are associated with intellectual disability (Gilfillan et al., 2008) and autistic behavior (Garbern et al., 2010). On Slc9a6 KO mice exhibit motor hyper-activity and cerebellar dysfunction (Stromme et al., 2011).

Fmr1.

Silencing of the FMR1 gene produces Fragile X Syndrome, the phenotype of which includes autism; two thirds of patients with Fragile X Syndrome meet screening criteria for an Autism Spectrum Disorder (Harris et al., 2008). Pediatric patients with Fragile X Syndrome also show lowered seizure threshold. The fmr1 knockout mouse replicates much of the phenotype of Fragile X Syndrome, including juvenile seizure susceptibility (Yan at al., 2004).

Methods

Animals in each of the above models are generated in accordance with the methodology described in the cited literature. Wild type equivalents are also obtained for each genetic model. Animals in each model are divided into three groups (n=10 to n=20): placebo treated wild type mice, mutant G-2-MePE-treated group and mutant placebo-treated control group.

The treatments are administered intraperitoneally: placebo (saline) or 20 mg/kg/day of G-2-MePE.

Measures of key features of ASD as displayed in each model are taken in accordance with the cited literature.

Results

G-2-MePE treatment significantly improves all measures associated with the ASD phenotype.

REFERENCES

The following references and all patents, patent applications and other publications cited herein are incorporated fully by reference.

Alarcon, M., Abrahams, B. S., Stone, J. L., Duvall, J, A., Perederiy, J. V., Bomar, J. M., Sebat, J., Wigler, M., Martin, C. L., Ledbetter, D. H., Nelson, S. F., Cantor, R. M., and Geschwind, D. H. (2008). Linkage, association, and gene-expression analyses identify CNTNAP2 as an autism-susceptibility gene. Am. J. Hum. Genet. 82, 150-159.

Amir R E, Van den Veyver I B, Wan M, Tran C Q, Francke U, Zoghbi H Y. Rett syndrome is caused by mutations in X-linked MECP2, encoding methyl-CpG-binding protein 2. Nat Genet. 1999 23:185-188

Andari E, Duhamel J R, Zalla T, Herbrecht E, Leboyer M, Sirigu A. (2010) Promoting social behavior with oxytocin in high-functioning autism spectrum disorders. PNAS 107: 4389-4394

Arking, D. E., Cutler, D. J., Brune, C. W., Teslovich, T. M., West, K., Ikeda, M., Rea, A., Guy, M., Lin, S., Cook, E. H., and Chakravarti, A. (2008). A common genetic variant in the neurexin superfamily member CNTNAP2 increases familial risk of autism. Am. J. Hum. Genet. 82, 160-164.

Bakkaloglu, B., O'Roak, B. J., Louvi, A., Gupta, A. R., Abelson, J. F., Morgan, T. M., Chawarska, K., Klin, A., Ercan-Sencicek, A. G., Stillman, A. A., Tanriover, G., Abrahams, B. S., Duvall, J. A., Robbins, E. M., Geschwind, D. H., Biederer, T., Gunel, M., Lifton, R. P., and State M W (2008). Molecular cytogenetic analysis and resequencing of contactin associated protein-like 2 in autism spectrum disorders.

Bakkaloglu, B., O'Roak, B. J., Louvi, A., Gupta, A. R., Abelson, J. F., Morgan, T. M., Chawarska, K., Klin, A., Ercan-Sencicek, A. G., Stillman, A. A., Tanriover, G., Abrahams, B. S., Duvall, J. A., Robbins, E. M., Geschwind, D. H., Biederer, T., Gunel, M., Lifton, R. P., and State M W (2008). Molecular cytogenetic analysis and resequencing of contactin associated protein-like 2 in autism spectrum disorders. Am. J. Hum. Genet. 82, 165-173.

Baron-Cohen S, Wheelwright S, Hill J, Raste Y, Plumb I (2001) The "Reading the Mind in the Eyes" test, revised version: A study with normal adults, and adults with Asperger's syndrome or high-functioning autism. J Child Psychol Psychiatry 42:241-251.

Belichenko P V, Oldfors A, Hagberg B, Dahlström A. Rett syndrome: 3-D confocal microscopy of cortical pyramidal dendrites and afferents. Neuroreport. 1994 5:1509-1513

Biederer T, Sara Y, Mozhayeva M, Atasoy D, Liu X, Kavalali E T, Súdhof T C. (2002) SynCAM, a synaptic adhesion molecule that drives synapse assembly. Science 297(5586): 1525-1531.

Chapleau C A, Larimore J L, Theibert A, Pozzo-Miller L. (2009) Modulation of dendritic spine development and plasticity by BDNF and vesicular trafficking: fundamental roles in neurodevelopmental disorders associated with mental retardation and autism. J. Neurodev. Disord. 1: 185-196.

Cheng C M, Mervis R F, Niu S L, Salem N Jr, Witters L A, Tseng V, Reinhardt R, Bondy C A. Insulin-like growth factor 1 is essential for normal dendritic growth. J Neurosci Res. 2003 73:1-9

Comery T A, Harris J B, Willems P J, Oostra B A, Irwin S A, Weiler I J, Greenough W T. (1997) Abnormal dendritic spines in fragile X knockout mice: maturation and pruning deficits. Proc. Natl Acad. Sci. USA 94: 5401-5404.

Durand C M, Betancur C, Boeckers T M, Bockmann J, Chaste P, Fauchereau F, Nygren G, Rastam M, Gillberg I C, Anckarsiter H, Sponheim E, Goubran-Botros H, Delorme R, Chabane N, Mouren-Simeoni M C, de Mas P, Bieth E, Rogé B, Héron D, Burglen L, Gillberg C, Leboyer M, Bourgeron T. (2007) Mutations in the gene encoding the synaptic scaffolding protein SHANK3 are associated with autism spectrum disorders. Nat Genet. 39: 25-27.

Etherton M R, Blaiss C A, Powell C M, Stüdhof T C. (2009) Mouse neurexin-1α deletion causes correlated electrophysiological and behavioural changes consistent with cognitive impairments. Proc. Nat. Acad. Sci. 106: 17998-18003.

Garbern, J. Y., Neumann, M., Trojanowski, J. Q., Lee, V. M., Feldman, G., Norris, J. W., Friez, M. J., Schwartz, C. E., Stevenson, R., and Sima, A. A. (2010). A mutation affecting the sodium/proton exchanger, SLC9A6, causes mental retardation with tau deposition. Brain 133, 1391-1402.

Gauthier J, Bonnel A, St-Onge J, Karemera L, Laurent S, Mottron L, Fombonne B, Joober R, Rouleau G A. (2005) NLGN3/NLGN4 gene mutations are not responsible for autism in the Quebec population. Am. J. Med. Genet. B. Neuropsychiatr. Genet. 1328(1): 74-75.

Gilfillan, G. D., Selmer, K. K., Roxrud, I., Smith, R., Kyllerman, M., Eiklid, K., Kroken, M., Mattingsdal, M., Egeland, T., Stenmark, H., Sjoholm, H., Server, A., Samuelsson, L., Christianson, A., Tarpey, P., Whibley, A., Stratton, M. R., Futreal, P. A., Teague, J., Edkins, S., Gecz, J., Turner, G., Raymond, F. L., Schwartz, C., Stevenson, R. E., Undlien, D. E., and Stromme, P. (2008). SLC9A6 mutations cause X-linked mental retardation, microcephaly, epilepsy, and ataxia, a phenotype mimicking Angelman syndrome. Am. J. Hum. Genet. 82, 1003-1010.

Gilman S R, Iossifov I, Levy D, Ronemus M, Wigler M, Vitkup D. Rare de novo variants associated with autism implicate a large functional network of genes involved in formation and function of synapses. Neuron. 2011 70:898-907

Giza J, Urbanski M J, Prestori F, Bandyopadhyay B, Yam A, Friedrich V, Kelley K, D'Angelo E, Goldfarb M. (2010) Behavioural and cerebellar transmission deficits in mice lacking autism-linked gene Islet Brain-2. J. Neurosci. 30: 14805-14816.

Guastella A J, Einfeld S L, Gray K M, Rinehart N J, Tonge B J, Lambert T J, Hickie I B. (2010) Intranasal oxytocin improves emotion recognition for youth with autism spectrum disorders. Biol Psychiatry. 67:692-694

Hagerman R, Hoem G, Hagerman P. (2010) Fragile X and autism: Intertwined at the molecular level leading to targeted treatments. Mol. Autism 1: 12-24.

Harris S W, Hessl D, Goodlin-Jones B, Ferranti J, Bacalman S, Barbato I, Tassone F, Hagerman P J, Herman H, Hagerman R J. (2008) Autism profiles of males with fragile X syndrome. Am J Ment Retard. 113:427-438.

Hiramoto T, Kang G, Suzuki G, Satoh Y, Kucherlapati R, Watanabe Y, Hiroi N. (2011) Tbx1: identification of a 22q11.2 gene as a risk factor for autism spectrum disorder in a mouse model. Hum Mol Genet. 2011 20:4775-4785.

Hutsler J J, Zhang H. Increased dendritic spine densities on cortical projection neurons in autism spectrum disorders. Brain Res. 2010 1309:83-94

Irwin S A, Galvez R, Greenough W T. Dendritic spine structural anomalies in fragile-X mental retardation syndrome. Cereb Cortex. 2000 10:1038-1044

Jamain S, Quach H, Betancur C, Røstam M, Colineaux C, Gillberg I C, Soderstrom H, Giros B, Leboyer M, Gillberg C, Bourgeron T; Paris Autism Research International Sibpair Study. (2003) Mutations of the X-linked genes encoding neuroligins NLGN3 and NLGN4 are associated with autism. Nat. Genet. 34: 27-29.

Jamain S, Radyushkin K, Hammerschmidt K, Granon S, Boretius S, Varoqueaux F, Ramanantsoa N, Gallego J, Ronnenberg A, Winter D, Frahm J, Fischer J, Bourgeron T, Ehrenreich H, Brose N. (2008) Reduced social interaction and ultrasonic communication in a mouse model of monogenic heritable autism. Proc. Nat. Acad. Sci. 105: 1710-1715.

Kim H G, Kishikawa S, Higgins A W, Seong I S, Donovan D J, Shen Y, Lally E, Weiss L A, Najm J, Kutsche K, Descartes M, Holt L, Braddock S, Troxell R, Kaplan L, Volkmar F, Klin A, Tsatsanis K, Harris D J, Noens I, Pauls D L, Daly M J, MacDonald M E, Morton C C, Quade B J, Gusella J F. (2008) Disruption of neurexin I associated with autism spectrum disorder. Am. J. Hum. Genet. 82: 199-207.

Klemmer P, Meredith R M, Holmgren C D, Klychnikov O I, Stahi-Zeng J, Loos M, van der Schors R C, Wortel J, de Wit H, Spijker S, Rotaru D C, Mansvelder H D, Smit A B, Li K W. Proteomics, ultrastructure, and physiology of hippocampal synapses in a fragile X syndrome mouse model reveal presynaptic phenotype. J Biol Chem, 2011 286: 25495-25504

Krueger D D, Osterweil E K, Chen S P, Tye L D, Bear M F. (2011) Cognitive dysfunction and prefrontal synaptic abnormalities in a mouse model of fragile X syndrome. Proc. Natl Acad. Sci. USA 108: 2587-2592.

Lauterborn J C, Rex C S, Kramár E, Chen L Y, Pandyarajan V, Lynch G, Gall C M. (2007) Brain-derived neurotrophic factor rescues synaptic plasticity in a mouse model of fragile X syndrome. J. Neurosci. 27: 10685-10694.

Lintas C, Persico A M. (2009) Autistic phenotypes and genetic testing: state-of-the-art for the clinical geneticist. J. Med. Genet. 46: 1-8.

Makkonen I, Kokki H, Kuikka J, Turpeinen U, Riikonen R. Effects of fluoxetine treatment on striatal dopamine transporter binding and cerebrospinal fluid insulin-like growth factor-1 in children with autism. Neuropediatrics. 2011 42:207-209

Marchetto et al. (2010) A model for neural development and treatment of Rett syndrome using human induced pluripotent stem cells. Cell 143:527-539 (incl. supplemental information)

Marshall C R, Noor A, Vincent J B, Lionel A C, Feuk L, Skaug J, Shago M, Moessner R, Pinto D, Ren Y, Thiruvahindrapduram B, Fiebig A, Schreiber S, Friedman J, Ketelaars C E, Vos Y J, Ficicioglu C, Kirkpatrick S, Nicolson R, Sloman L, Summers A, Gibbons C A, Teebi A, Chitayat D, Weksberg R, Thompson A, Vardy C, Crosbie V, Luscombe S, Baatjes R, Zwaigenbaum L, Roberts W, Fernandez B, Szatmari P, Scherer S W. (2008) Structural variation of chromosomes in autism spectrum disorder. Am J Hum Genet. 82: 477-488.

Minshew N J, Williams D L. The new neurobiology of autism: cortex, connectivity, and neuronal organization. Arch Neurol. 2007 64:945-950

Moessner R, Marshall C R, Sutcliffe J S, Skaug J, Pinto D, Vincent J, Zwaigenbaum L, Fenandez B, Roberts W, Szatmari P, Scherer S W. (2007) Contribution of SHANK3 mutations to autism spectrum disorder. Am. J. Hum. Genetics 81: 1289-1297.

Moretti P, Levenson J M, Battaglia F, Atkinson R, Teague R, Antalffy B, Armstrong D, Arancio O, Sweatt J D, Zoghbi H Y. (2006) Learning and memory and synaptic plasticity are impaired in a mouse model of Rett syndrome. J. Neurosci. 26: 319-327.

Paylor, R., Glaser, B., Mupo, A., Ataliotis, P., Spencer, C., Sobotka, A., Sparks, C., Choi, C. H., Oghalai, J., Curran, S., Murphy, K. C., Monks, S., Williams, N., O'Donovan, M. C., Owen, M. J., Scambler, P. J., and Lindsay, E. (2006). PNAS 103, 7729-7734.

Penagarikano, O., Abrahams, B. S., Herman, E. I., Winden, K. D., Gdalyahu, A., Dong, H., Sonnenblick, L. I., Gruver, R., Almajano, J., Bragin, A., Golshani, P., Trachtenberg, J. T., Peles, E., and Geschwind, D. H. (2011). Absence of CNTNAP2 Leads to Epilepsy, Neuronal Migration Abnormalities, and Core Autism-Related Deficits. Cell 147, 235-246.

Riikonen R, Makkonen I, Vanhala R, Turpeinen U, Kuikka J, Kokki H. (2006) Cerebrospinal fluid insulin-like growth factors IGF-1 and IGF-2 in infantile autism. Dev. Med. Child Neurol. 48: 751-755.

Sebat J, Lakshmi B, Malhotra D, Troge J, Lese-Martin C, Walsh T, Yamrom B, Yoon S, Krasnitz A, Kendall J, Leotta A, Pai D, Zhang R, Lee Y H, Hicks J, Spence S J, Lee A T, Puura K, Lehtimiki T, Ledbetter D, Gregersen P K, Bregman J, Sutcliffe J S, Jobanputra V, Chung W, Warburton D, King M C, Skuse D, Geschwind D H, Gilliam T C, Ye K, Wigler M. (2007) Strong association of de novo copy number variation mutations with autism. Science 316(5823): 445-449.

Schaevitz L R, Moriuchi J M, Nag N, Mellot Ti, Berger-Sweeney J. (2010) Cognitive and social functions and growth factors in a mouse model of Rett syndrome. Physiol. Behav. 100: 255-263.

Schütt J, Falley K, Richter D, Kreienkamp H J, Kindler S. (2009) Fragile X mental retardation protein regulates the levels of scaffold proteins and glutamate receptors in postsynaptic densities. J. Biol. Chem. 284: 25479-25487.

Silverman J L, Turner S M, Barkan C L, Tolu S S, Saxena R, Hung A Y, Sheng M, Crawley J N: Sociability and motor functions in Shank1 mutant mice. Brain Res 2010.

Silverman J L, Yang M, Lord C, Crawley J N: Behavioural phenotyping assays for mouse models of autism. Nat Rev Neurosci 2010, 11:490-502.

Spence S J, Schneider M T. The role of epilepsy and epileptiform EEGs in autism spectrum disorders. Pediatr Res. 2009 65:599-606.

Spencer C M, Alekseyenko O, Serysheva E, Yuva-Paylor L A, Paylor R. (2005) Altered anxiety-related and social behaviors in the Fmr1 knockout mouse model of fragile X syndrome. Genes Brain Behav. 4: 420-430.

Strauss, K. A., Puffenberger, E. G., Huentelman, M. J., Gottlieb, S., Dobrin, S. E., Parod, J. M., Stephan, D. A., and Morton, D. H. (2006). Recessive symptomatic focal epilepsy and mutant contactin-associated protein-like 2. N. Engl. J. Med. 354, 1370-1377.

Stromme, P., Dobrenis, K., Sillitoe, R. V., Gulinello, M., Ali, N. F., Davidson, C., Micsenyi, M. C., Stephney, G., Ellevog, L., Klungland, A., and Walkley, S. U. (2011). X-linked Angelman-like syndrome caused by Sic9a6 knockout in mice exhibits evidence of endosomal-lysosomal dysfunction. Brain. 134:3369-3383.

Sykes N H, Toma C, Wilson N, Volpi E V, Sousa I, Pagnamenta A T, Tancredi R, Battaglia A, Maestrini E, Bailey A J, Monaco A P; International Molecular Genetic Study of Autism Consortium (IMGSAC). (2009) Copy number variation and association analysis of SHANK3 as a candidate gene for autism in the IMGSAC collection. Eur. J. Hum. Genet. 17: 1347-1353.

Tabuchi K, Blundell J, Etherton M R, Hammer R E, Liu X, Powell C M, Sidhof T C, (2007) A neuroligin-3 mutation implicated in autism increases inhibitory synaptic transmission in mice. Science 318(5847): 71-76.

Takayanagi Y, Fujita E, Yu Z, Yamagata T, Momoi M Y, Momoi T, Onaka T. (2010) Impairment of social and emotional behaviors in Cadm1-knockout mice. Biochem, Biophys. Res. Commun. 396: 703-708.

Tropea D, Giacometti E, Wilson N R, Beard C, McCurry C, Fu D D, Flannery R, Jaenisch R, Sur M. (2009) Partial reversal of Rett Syndrome-like symptoms in MeCP2 mutant mice. Proc. Natl Acad. Sci. USA 106: 2029-2034.

Vernes, S. C., Newbury, D. F., Abrahams, B. S., Winchester, L., Nicod, J., Groszer, M., Alarcon, M., Oliver, P. L., Davies, K. E., Geschwind, D. H., Monaco, A. P., and Fisher, S. E. (2008). A functional genetic link between distinct developmental language disorders. N. Engl. J. Med. 359, 2337-2345.

Yan J, Noltner K, Feng J, Li W, Schroer R, Skinner C, Zeng W, Schwartz C E, Sommer S S. (2008) Neurexin 1 alpha structural variants associated with autism. Neurosci Lett. 438: 368-370.

Yan Q J, Asafo-Adjei P K, Arnold H M, Brown R E, Bauchwitz R P. (2004) A phenotypic and molecular characterization of the fmr1-tm1Cgr fragile X mouse, Genes Brain Behav. 3:337-359.

Yang M, Crawley J N: Simple behavioural assessment of mouse olfaction. Curr Protoc Neurosci 2009, Chapter 8(Unit 8):24, Zhiling Y, Fujita E, Tanabe Y, Yamagata T, Momoi T, Momoi M Y. (2008) Mutations in the gene encoding CADM1 are associated with autism spectrum disorder. Biochem. Biophys. Res. Commun. 377: 926-929.

Zhao M G, Toyoda H, Ko S W, Ding H K, Wu L J, Zhuo M. (2005) Deficits in trace fear memory and long-term potentiation in a mouse model for fragile X syndrome. J. Neurosci. 25: 7385-7392. (Erratum in: J Neurosci. 2005, 25: 8112)

Zoghbi H Y. (2005) MeCP2 dysfunction in humans and mice. J Child Neurol. 20: 736-740.

We claim:

1. A method for treating a human being suffering from a symptom of Rett Syndrome, comprising oral administration to said human being an effective amount of an aqueous solution of Glycyl-2-Methyl-L-prolyl-L-glutamate (G-2-MePE).

2. The method of claim 1, said effective amount of G-2-MePE being in the range of about 1 mg/Kg to about 100 mg/Kg.

3. The method of claim 1, where said G-2-MePE is administered in a dose of about 60 mg/kg twice per day ("b.i.d.").

4. The method of claim 1, where said G-2-MePE is administered to a mucosa of said human being.

5. The method of claim 1, further comprising administering to the human being a second therapeutic agent selected from a group consisting of: insulin-like growth factor-I (IGF-I), insulin-like growth factor-II (IGF-II), glycyl-prolyl-glutamate (GPE), transforming growth factor-$\beta$1, activin, growth hormone, nerve growth factor, brain-derived neurotrophic factor (BDNF), growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor, int-2, fibroblast growth factor homologous factor-1 (FHF-1), FHF-2, FHF-3, FHF-4, keratinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-interferon, $\beta$-interferon, $\gamma$-, consensus interferon, TNF-$\alpha$, clomethiazole; kynurenic acid, Semax, tacrolimus, L-threo-1-phenyl-2-decanoylamino-3-morpholino-1-propanol, andrenocorticotropin-(4-9), analog [ORG 2766], dizolcipine (MK-801), selegiline; mematine, NPS1506, GV1505260, MK-801, GV150526; 2,3-dihydroxy-6-nitro-7-sulfamoylbenzo(f)quinoxaline (NBQX), LY303070, LY300164; anti-MAdCAM-1mAb, MECA-367 (ATCC accession no. HB-9478), fenobam, fluoxetine, and risperidone.

6. The method of claim 1, where said dose of said compound is 10 mg/kg three times per day or 30 mg/kg three times per day.

7. The method of claim 1, said treatment producing an improvement in said symptom as assessed by one or more behavioral test selected from the group consisting of The Rett Syndrome Natural History/Clinical Severity Scale, Aberrant Behavior Checklist Community Edition (ABC), Vinelands, Clinical Global Impression of Severity (CGI-S) and their carers completed the Caregiver Strain Questionnaire (CSQ), or one or more physiological test selected from the group consisting of electroencephalogram (EEG) spike frequency, overall power in frequency bands of an EEG, hand movement, QTc and heart rate variability (HRV), and respiratory irregularities compared to control animals not suffering from said symptom.

* * * * *